(12) United States Patent
Qian et al.

(10) Patent No.: US 11,970,523 B2
(45) Date of Patent: Apr. 30, 2024

(54) LONG-ACTING OXYNTOMODULIN HYBRID PEPTIDE, PREPARATION METHOD THEREFOR, AND APPLICATION THEREOF

(71) Applicant: CHINA PHARMACEUTICAL UNIVERSITY, Nanjing (CN)

(72) Inventors: Hai Qian, Nanjing (CN); Wenlong Huang, Nanjing (CN); Xingguang Cai, Nanjing (CN); Chengye Li, Nanjing (CN); Chunxia Liu, Nanjing (CN); Yuxuan Dai, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 454 days.

(21) Appl. No.: 17/262,489

(22) PCT Filed: May 6, 2019

(86) PCT No.: PCT/CN2019/085593
§ 371 (c)(1),
(2) Date: Jan. 22, 2021

(87) PCT Pub. No.: WO2020/019813
PCT Pub. Date: Jan. 30, 2020

(65) Prior Publication Data
US 2022/0177537 A1    Jun. 9, 2022

(30) Foreign Application Priority Data

| Jul. 25, 2018 | (CN) | 201810851064.0 |
| Jul. 25, 2018 | (CN) | 201810851507.6 |
| Jul. 25, 2018 | (CN) | 201810851509.5 |
| Jul. 25, 2018 | (CN) | 201810851571.4 |

(51) Int. Cl.
| A61K 38/00 | (2006.01) |
| A61P 1/16 | (2006.01) |
| A61P 3/04 | (2006.01) |
| A61P 3/06 | (2006.01) |
| A61P 3/10 | (2006.01) |
| C07K 14/575 | (2006.01) |

(52) U.S. Cl.
CPC ............. *C07K 14/575* (2013.01); *A61P 1/16* (2018.01); *A61P 3/04* (2018.01); *A61P 3/06* (2018.01); *A61P 3/10* (2018.01); *A61K 38/00* (2013.01)

(58) Field of Classification Search
CPC ......... C07K 14/575; A61K 38/00; A61P 3/04; A61P 3/06; A61P 3/10
See application file for complete search history.

(56) References Cited

U.S. PATENT DOCUMENTS

| 9,527,898 | B2* | 12/2016 | Jung | A61K 38/26 |
| 9,944,687 | B2* | 4/2018 | Bloom | A61P 3/10 |
| 2006/0094652 | A1* | 5/2006 | Levy | A61P 3/06 |
| | | | | 514/12.6 |
| 2011/0281797 | A1* | 11/2011 | Tonon | A61K 47/60 |
| | | | | 435/68.1 |

OTHER PUBLICATIONS

Perfetti et al. (Eur. J. Endocr. 143, 717-725, 2000).*
Gutniak et al. ( New England J. Med. 30 326:1316-1322, 1992).*
Lehninger, Principles of Biochemistry, 4th Edition, chapter 3, pub. year 2004.*

* cited by examiner

*Primary Examiner* — Gyan Chandra
(74) *Attorney, Agent, or Firm* — CBM PATENT CONSULTING, LLC

(57) ABSTRACT

The present invention discloses a polypeptide and application thereof. By modifying oxyntomodulin (OXM), hybridizing OXM with a peptide sequence of Exenatide, including enabling the polypeptide to be resistant to DPP-4 enzyme degradation through amino acid modification, and conjugating fatty acid chains at the same time, an OXM hybrid peptide having longer pharmacologic action time and better weight losing effects is obtained. Synthesis of a target polypeptide is fast realized by an orthogonal protection strategy solid-phase synthesis method, and a crude product is purified and freeze-dried to obtain the OXM hybrid peptide.

8 Claims, 20 Drawing Sheets
Specification includes a Sequence Listing.

SEQUENCE LISTING

<160> NUMBER OF SEQ ID NOS: 8

<210> SEQ ID NO 1
<211> LENGTH: 37
<212> TYPE: PRT
<213> ORGANISM: Artificial Sequence
<220> FEATURE:
<223> OTHER INFORMATION: It is synthesized.

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 13
<212> TYPE: PRT
<213> ORGANISM: Artificial Sequence
<220> FEATURE:
<223> OTHER INFORMATION: It is synthesized.

<400> SEQUENCE: 2

Gln Gly Thr Phe Thr Ser Asp Tyr Ser Lys Tyr Met Asp
1               5                   10

<210> SEQ ID NO 3
<211> LENGTH: 22
<212> TYPE: PRT
<213> ORGANISM: Artificial Sequence
<220> FEATURE:
<223> OTHER INFORMATION: It is synthesized.

<400> SEQUENCE: 3

Arg Arg Ala Gln Asp Phe Val Gln Trp Leu Lys Asn Gly Gly Pro Ser
1               5                   10                  15

Ser Gly Ala Pro Pro Pro
            20

<210> SEQ ID NO 4
<211> LENGTH: 13
<212> TYPE: PRT
<213> ORGANISM: Artificial Sequence
<220> FEATURE:
<223> OTHER INFORMATION: It is synthesized.

<400> SEQUENCE: 4

Gln Gly Thr Phe Thr Ser Asp Tyr Ser Lys Tyr Leu Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: It is synthesized.

<400> SEQUENCE: 5

Gln Gly Thr Phe Thr Ser Asp Tyr Ser Lys Tyr Leu Asp
1               5                   10

<210> SEQ ID NO 6
<211> LENGTH: 22

```
<212> TYPE: PRT
<213> ORGANISM: Artificial Sequence
<220> FEATURE:
<223> OTHER INFORMATION: It is synthesized.

<400> SEQUENCE: 6

Glu Arg Ala Gln Asp Phe Val Gln Trp Leu Lys Asn Gly Gly Pro Ser
1               5                   10                  15

Ser Gly Ala Pro Pro Pro
            20

<210> SEQ ID NO 7
<211> LENGTH: 22
<212> TYPE: PRT
<213> ORGANISM: Artificial Sequence
<220> FEATURE:
<223> OTHER INFORMATION: It is synthesized.

<400> SEQUENCE: 7

Arg Arg Val Gln Asp Phe Val Gln Trp Leu Lys Asn Gly Gly Pro Ser
1               5                   10                  15

Ser Gly Ala Pro Pro Pro
            20

<210> SEQ ID NO 8
<211> LENGTH: 22
<212> TYPE: PRT
<213> ORGANISM: Artificial Sequence
<220> FEATURE:
<223> OTHER INFORMATION: It is synthesized.

<400> SEQUENCE: 8

Arg Arg Ala Gln Asp Phe Val Glu Trp Leu Lys Asn Gly Gly Pro Ser
1               5                   10                  15

Ser Gly Ala Pro Pro Pro
            20
```

LONG-ACTING OXYNTOMODULIN HYBRID PEPTIDE, PREPARATION METHOD THEREFOR, AND APPLICATION THEREOF

TECHNICAL FIELD

The present invention relates to the field of medicinal chemistry, and more particularly relates to a long-acting oxyntomodulin hybrid peptide, and a preparation method and application thereof.

BACKGROUND ART

The cause of the metabolic syndrome is abnormal metabolism of a variety of substances such as proteins, fats and carbohydrates. Excessive nutrition, physical activity reduction and the like may lead to obesity and obesity-related diseases, such as diabetes. In recent years, the incidence of type 2 diabetes and abnormal lipid metabolism has been increasing.

Oxyntomodulin (OXM) is a polypeptide consists of 37 amino acids secreted by L cells of the small intestine, contains entire 29 amino acid sequences of glucagon and 8 amino acid portions extending at a C-terminal, and has 50% homology with glucagon-like peptide-1 (GLP-1). A peptide sequence is: HSQGTFTSDYSKYLDSR-RAQDFVQWLMNTKRNRNNIA (SEQ ID NO.:01). OXM can activate a glucagon-like peptide-1 receptor (GLP-1R) and a glucagon receptor (GCGR) at the same time, and has a certain effect of slowing weight gain and lowering glucose. After OXM activates GCGR, liver glycogen decomposition and gluconeogenesis can be promoted, and lipolysis and fatty acid oxidation can be promoted; and amino acids are accelerated to enter into liver cells, a heat production effect is achieved, and better weight loss and appetite suppression effects are achieved. Compared with a simple GLP-1R agonist, OXM has a better effect of intervening body weight, regulating lipid metabolism and improving glucose tolerance, but has a relatively weak blood glucose lowering activity and a short half-life period.

GLP-1 is a glucose-dependent incretin hormone. It can stimulate GLP-1R to achieve the hypoglycemic effect. The most significant function is to promote the regeneration and repair of β cells, and to increase the quantity of islet β cells, at the same time, the risk of hypoglycemia often occurring in diabetes treatment can be avoided, and wide application prospects in the field of diabetes treatment are realized. Exenatide is a typical short-acting GLP-1 receptor agonist for reducing DPP-IV enzyme metabolism. By introducing a partial peptide sequence of Exenatide in OXM, the receptor agonistic activity of a compound on GLP-1R can be improved.

SUMMARY OF THE INVENTION

Objective of the present invention: The present invention synthesizes a class of peptide sequence-modified OXM analogs. Through a structure of hybridizing OXM with a partial peptide sequence of Exenatide, the affinity of a peptide chain to GLP-1R is enhanced, the agonistic activity on GLP-1R is enhanced, the moderate GCGR agonistic activity is maintained, and a class of peptide sequence-modified OXM analogs are synthesized. Small molecules of coumarin, different kinds of fatty acids and the like have a high serum albumin binding rate. By conjugating the small molecules with OXM analogs, the duration of the hypoglycemic effect is greatly prolonged, exceeding that of existing marketed medicines liraglutide and exenatide. A series of long-acting polypeptide medicines with excellent hypoglycemic activity and weight losing effects are obtained.

Technical solution: In a first aspect, the present invention relates to a class of hypoglycemic polypeptides or pharmaceutically acceptable salts thereof. The amino acid sequence of the polypeptide has a general formula His-Xaa1-PP1-Xaa2-PP2-Xaa3:

wherein

PP1 is a polypeptide selecting from the group of polypeptides having the amino acid sequences shown as SEQ ID NO.:02, SEQ ID NO.:04 and SEQ ID NO.:05; PP2 is a polypeptide selecting from the group of polypeptides having the amino acid sequences shown as SEQ ID NO.:03, SEQ ID NO.:06, SEQ ID NO.:07 and SEQ ID NO.:08; PP1 is the polypeptide selecting from the group of polypeptides having the amino acid sequences shown as SEQ ID NO.:02, SEQ ID NO.:04 and SEQ ID NO.:05 when PP2 is the polypeptide having the amino acid sequence shown as SEQ ID NO.:03; PP1 is the polypeptide having the amino acid sequence shown as SEQ ID NO.:05 when PP2 is the polypeptide selecting from the group of polypeptides having the amino acid sequences shown as SEQ ID NO.:06, SEQ ID NO.:07 and SEQ ID NO.:08;

Xaa1 is Gly, Aib, D-Ser, Ser, Arg, Asn, Asp, Cys, Gln, Glu, His, Ile, Leu, Lys, Met, Phe, Pro, Thr, Trp, Tyr or Val;

Xaa2 is selected from

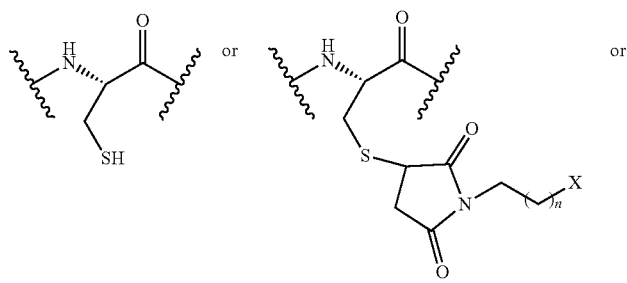

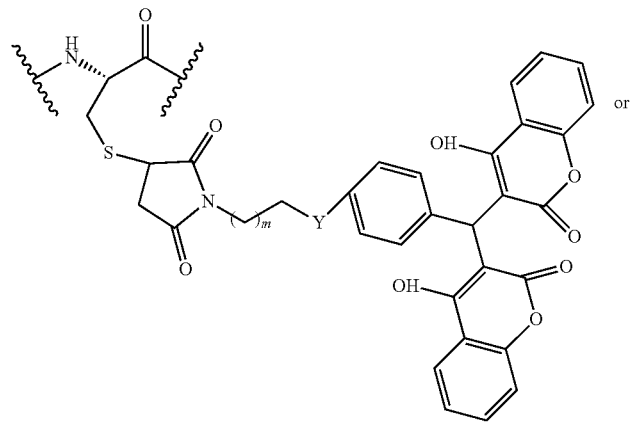
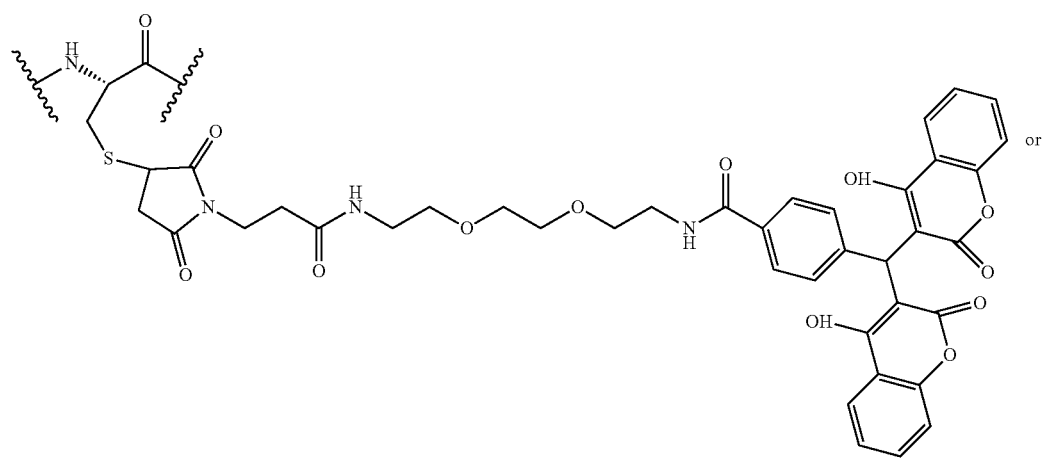
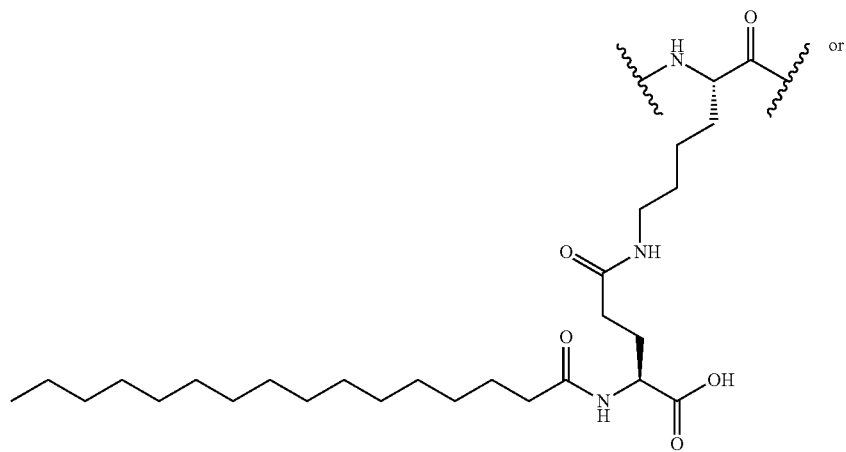

-continued

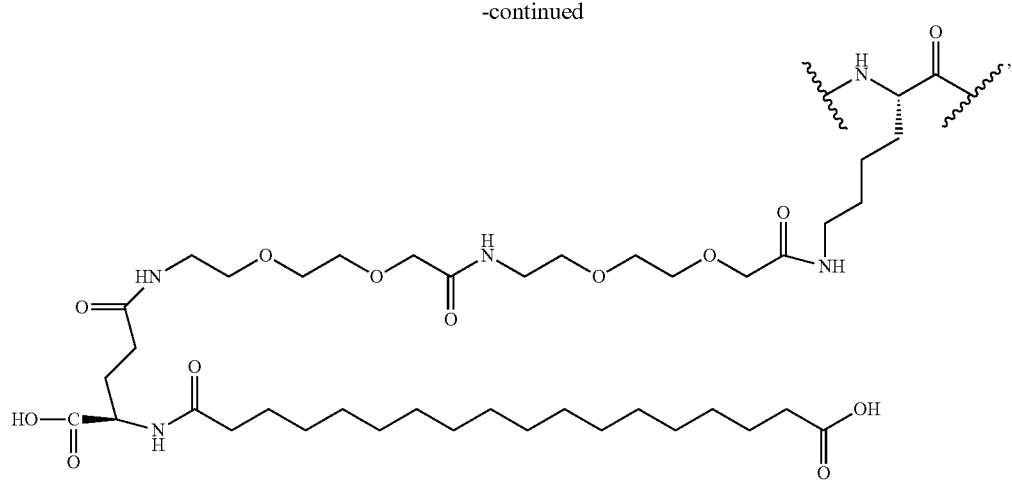

wherein X is —CH₃ or —COOH;
Y is —NH—CO— or —CO—NH—;
n is a natural number selected from 0 to 20;
m is a natural number selected from 1 to 20; and
Xaa3 is Ser-OH or Ser-NH₂.

According to a preferable solution, the present invention is characterized by:

His-Xaa1-PP1-Xaa2-PP2-Xaa3 has PP1 is a polypeptide selecting from the group of polypeptides having the amino acid sequences shown as SEQ ID NO.:02, SEQ ID NO.:04 and SEQ ID NO.:05; PP2 is a polypeptide selecting from the group of polypeptides having the amino acid sequences shown as SEQ ID NO.:03, SEQ ID NO.:06, SEQ ID NO.:07 and SEQ ID NO.:08; PP1 is the polypeptide selecting from the group of polypeptides having the amino acid sequences shown as SEQ ID NO.:02, SEQ ID NO.:04 and SEQ ID NO.:05 when PP2 is the polypeptide having the amino acid sequence shown as SEQ ID NO.:03; PP1 is the polypeptide having the amino acid sequence shown as SEQ ID NO.:05 when PP2 is the polypeptide selecting from the group of polypeptides having the amino acid sequences shown as SEQ ID NO.:06, SEQ ID NO.:07 and SEQ ID NO.:08;

wherein
Xaa1 is selected from Gly or Aib;
Xaa2 is selected from

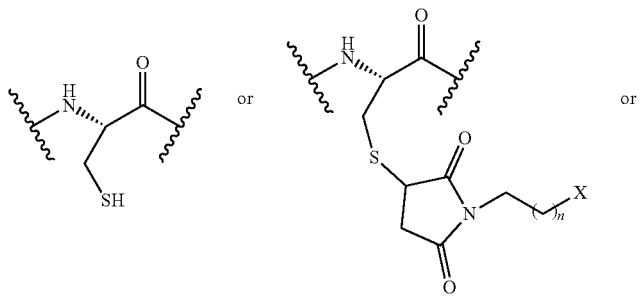

or

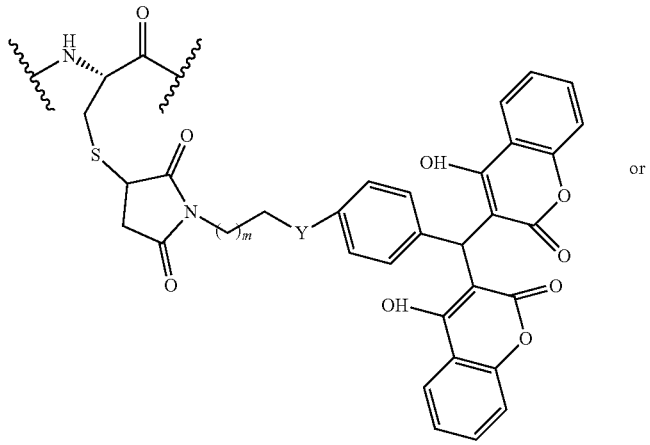

or

-continued

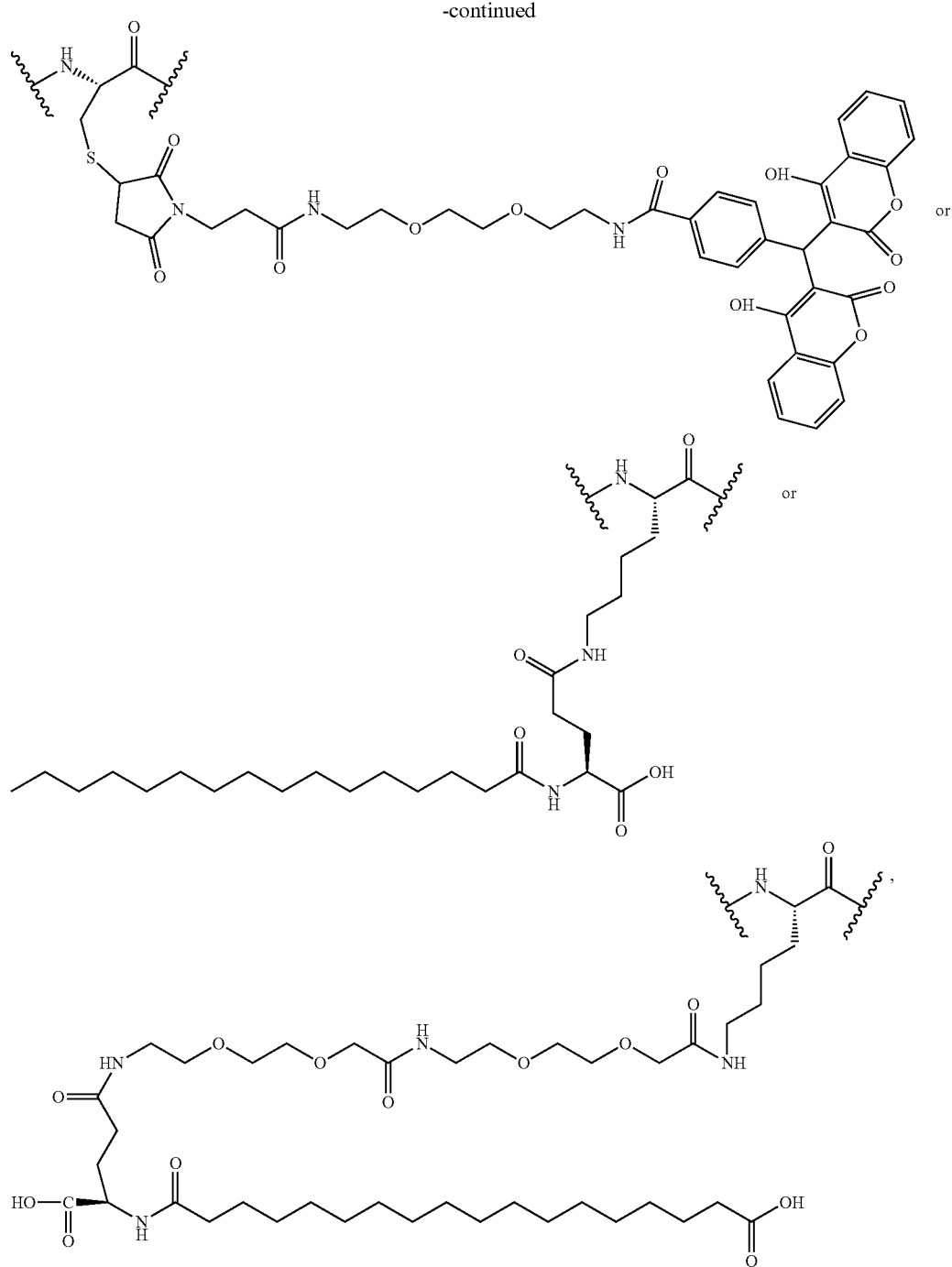

or or wherein X is —CH₃ or —COOH;
Y is —NH—CO— or —CO—NH—;
n is a natural number selected from 6, 10, 14, 11, or 15;
m is a natural number selected from 10 or 11;
Xaa3 is selected from Ser-OH or Ser-NH₂.

The hypoglycemic polypeptide or the pharmaceutically acceptable salt thereof in the present invention may also be expressed as:

compound 1: His-Gly-PP1-Cys-PP2-Ser-NH2 wherein PP1 is the polypeptide having the amino acid sequence shown as SEQ ID NO.:02 and PP2 is the polypeptide having the amino acid sequence shown as SEQ ID NO.:03, compound 2: His-Gly-PP1-Cys-PP2-Ser-NH2 wherein PP1 is the polypeptide having the amino acid sequence shown as SEQ ID NO.:04 and PP2 is the polypeptide having the amino acid sequence shown as SEQ ID NO.:03, compound 3: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:06, compound 4: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:07, compound 5: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:03, compound 6: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:08, compound 7:

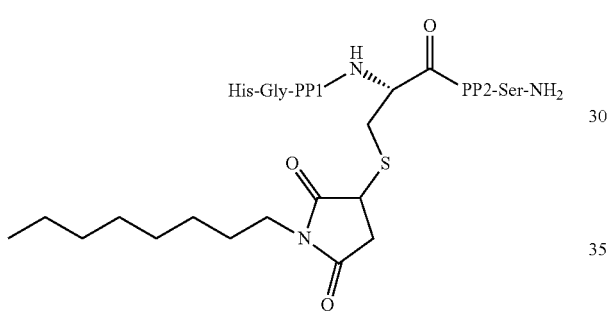

wherein PP1 is the polypeptide having the amino acid sequence shown as SEQ ID NO.:02 and PP2 is the polypeptide having the amino acid sequence shown as SEQ ID NO.:03, compound 8:

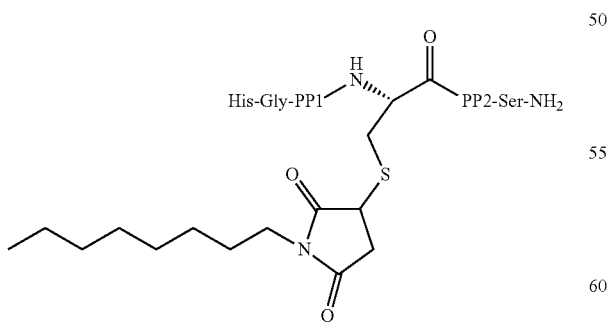

wherein PP1 is the polypeptide having the amino acid sequence shown as SEQ ID NO.:04 and PP2 is the polypeptide having the amino acid sequence shown as SEQ ID NO.:03, compound 9:

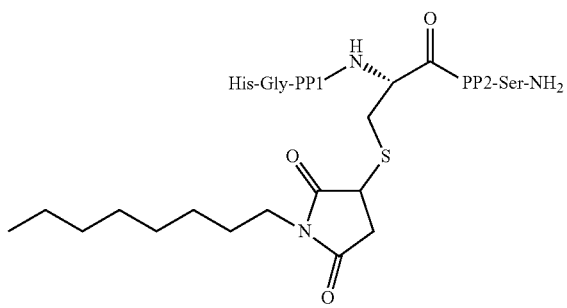

wherein PP1 is the polypeptide having the amino acid sequence shown as SEQ ID NO.:05 and PP2 is the polypeptide having the amino acid sequence shown as SEQ ID NO.:06, compound 10:

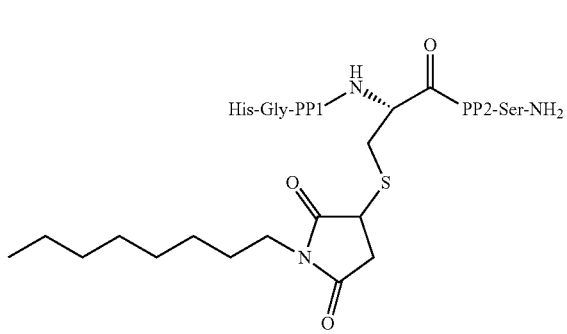

wherein PP1 is the polypeptide having the amino acid sequence shown as SEQ ID NO.:05 and PP2 is the polypeptide having the amino acid sequence shown as SEQ ID NO.:07, compound 11:

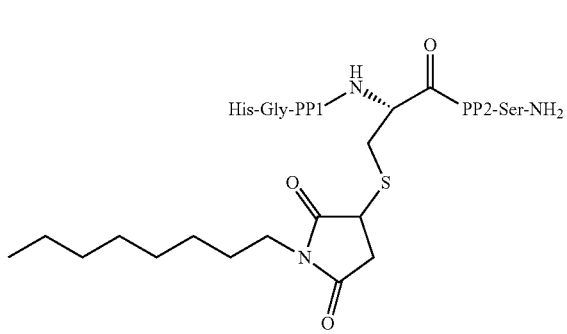

wherein PP1 is the polypeptide having the amino acid sequence shown as SEQ ID NO.:05 and PP2 is the polypeptide having the amino acid sequence shown as SEQ ID NO.:03, compound 12:

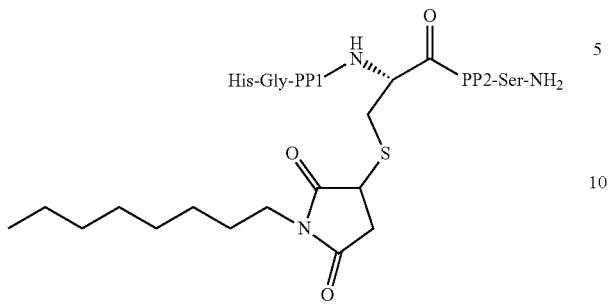

wherein PP1 is the polypeptide having the amino acid sequence shown as SEQ ID NO.:05 and PP2 is the polypeptide having the amino acid sequence shown as SEQ ID NO.:08, compound 13:

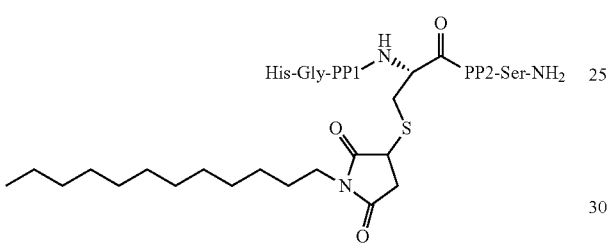

wherein PP1 is the polypeptide having the amino acid sequence shown as SEQ ID NO.:02 and PP2 is the polypeptide having the amino acid sequence shown as SEQ ID NO.:03, compound 14:

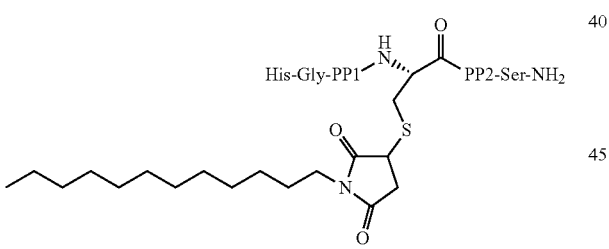

wherein PP1 is the polypeptide having the amino acid sequence shown as SEQ ID NO.:04 and PP2 is the polypeptide having the amino acid sequence shown as SEQ ID NO.:03, compound 15:

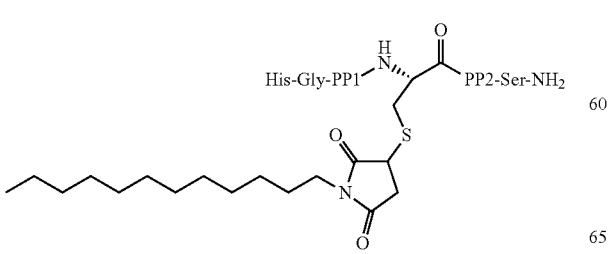

wherein PP1 is the polypeptide having the amino acid sequence shown as SEQ ID NO.:05 and PP2 is the polypeptide having the amino acid sequence shown as SEQ ID NO.:06, compound 16:

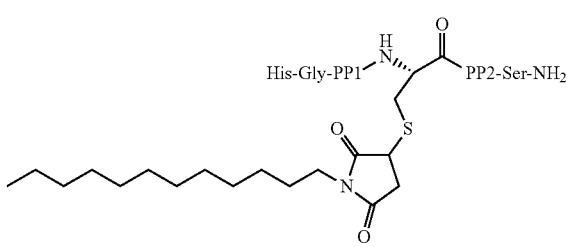

wherein PP1 is the polypeptide having the amino acid sequence shown as SEQ ID NO.:05 and PP2 is the polypeptide having the amino acid sequence shown as SEQ ID NO.:07, compound 17:

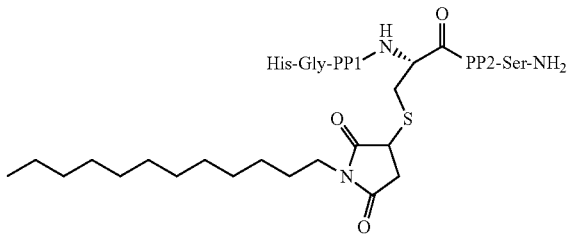

wherein PP1 is the polypeptide having the amino acid sequence shown as SEQ ID NO.:05 and PP2 is the polypeptide having the amino acid sequence shown as SEQ ID NO.:03, compound 18:

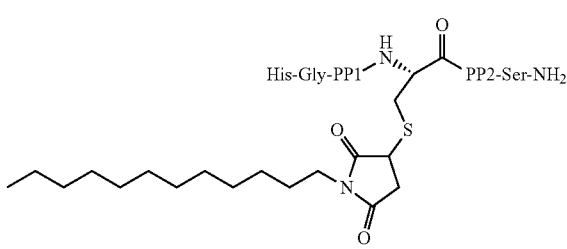

wherein PP1 is the polypeptide having the amino acid sequence shown as SEQ ID NO.:05 and PP2 is the polypeptide having the amino acid sequence shown as SEQ ID NO.:08, compound 19:

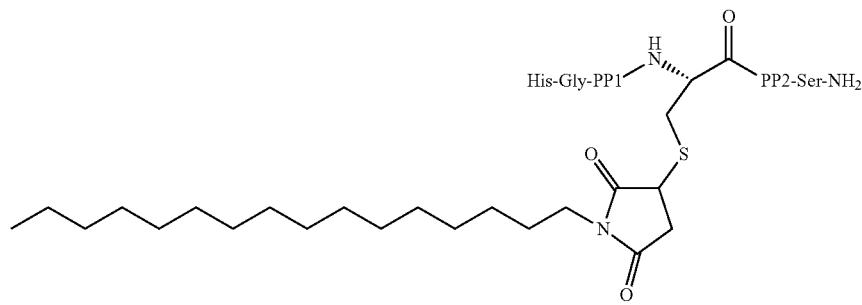

wherein PP1 is the polypeptide having the amino acid sequence shown as SEQ ID NO.:02 and PP2 is the polypeptide having the amino acid sequence shown as SEQ ID NO.:03, compound 20:

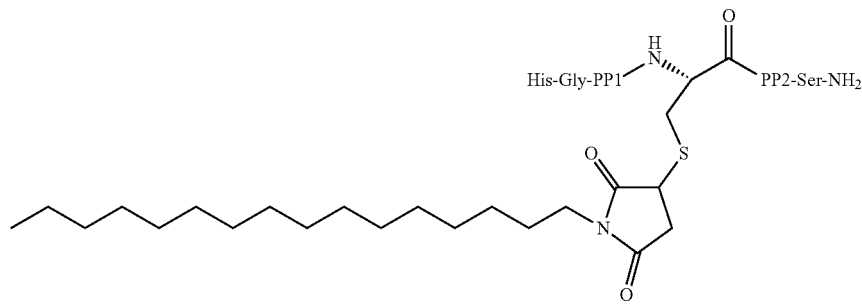

wherein PP1 is the polypeptide having the amino acid sequence shown as SEQ ID NO.:04 and PP2 is the polypeptide having the amino acid sequence shown as SEQ ID NO.:03, compound 21:

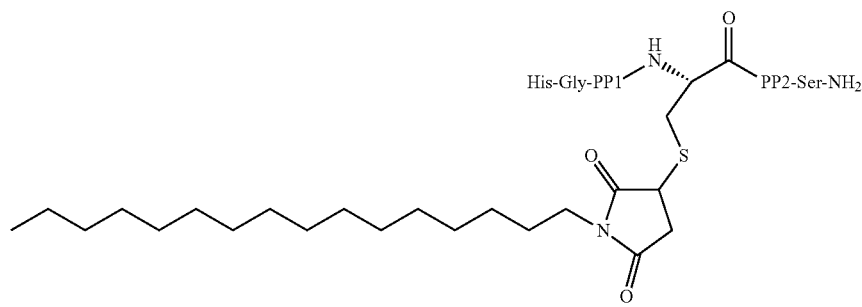

wherein PP1 is the polypeptide having the amino acid sequence shown as SEQ ID NO.:05 and PP2 is the polypeptide having the amino acid sequence shown as SEQ ID NO.:06, compound 22:

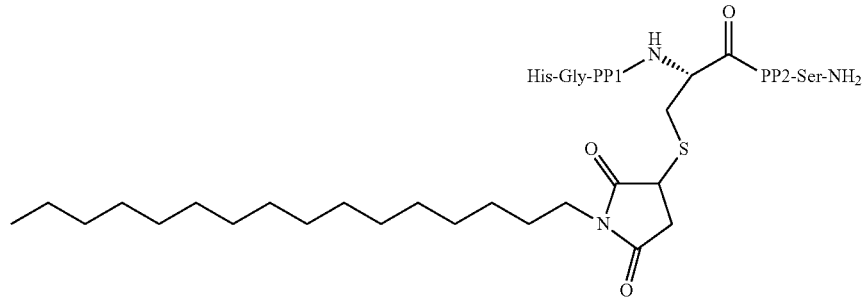

wherein PP1 is the polypeptide having the amino acid sequence shown as SEQ ID NO.:05 and PP2 is the polypeptide having the amino acid sequence shown as SEQ ID NO.:07, compound 23:

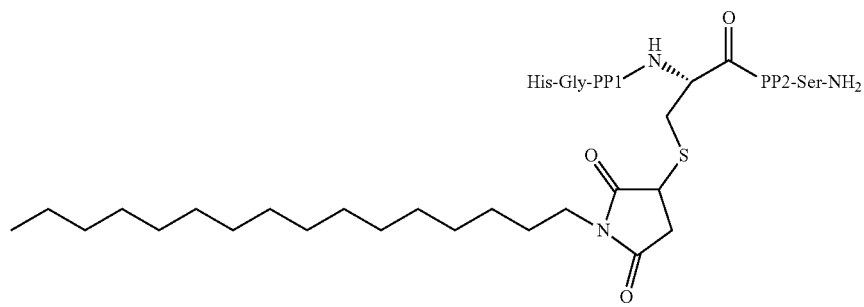

wherein PP1 is the polypeptide having the amino acid sequence shown as SEQ ID NO.:05 and PP2 is the polypeptide having the amino acid sequence shown as SEQ ID NO.:03, compound 24:

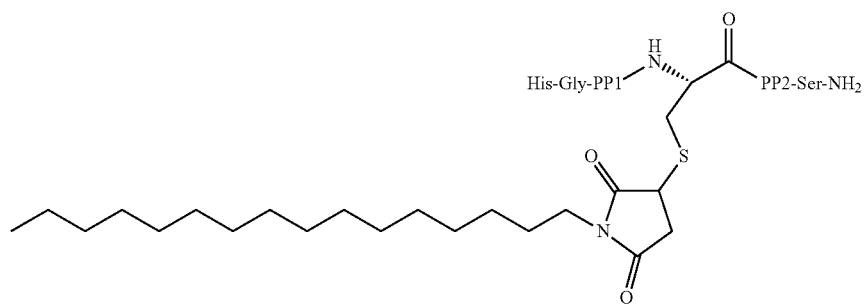

wherein PP1 is the polypeptide having the amino acid sequence shown as SEQ ID NO.:05 and PP2 is the polypeptide having the amino acid sequence shown as SEQ ID NO.:08, compound 25:

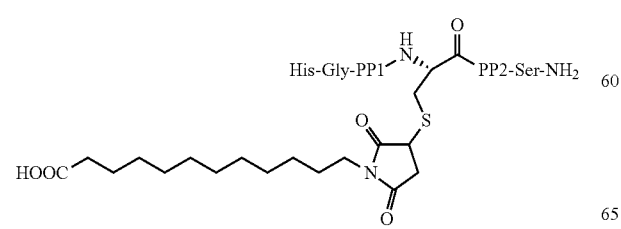

wherein PP1 is the polypeptide having the amino acid sequence shown as SEQ ID NO.:05 and PP2 is the polypeptide having the amino acid sequence shown as SEQ ID NO.:08, compound 26:

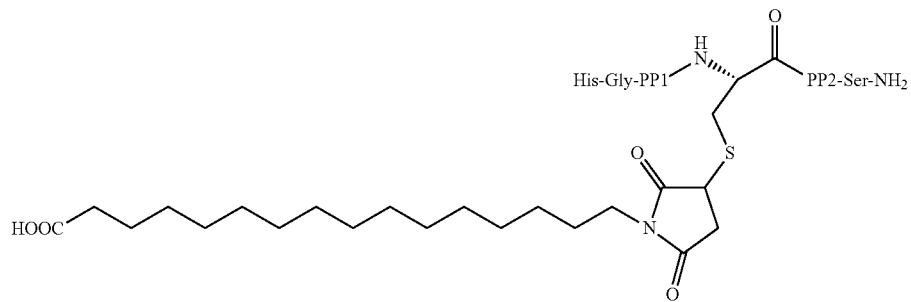

wherein PP1 is the polypeptide having the amino acid sequence shown as SEQ ID NO.:05 and PP2 is the polypeptide having the amino acid sequence shown as SEQ ID NO.:08, compound 27:

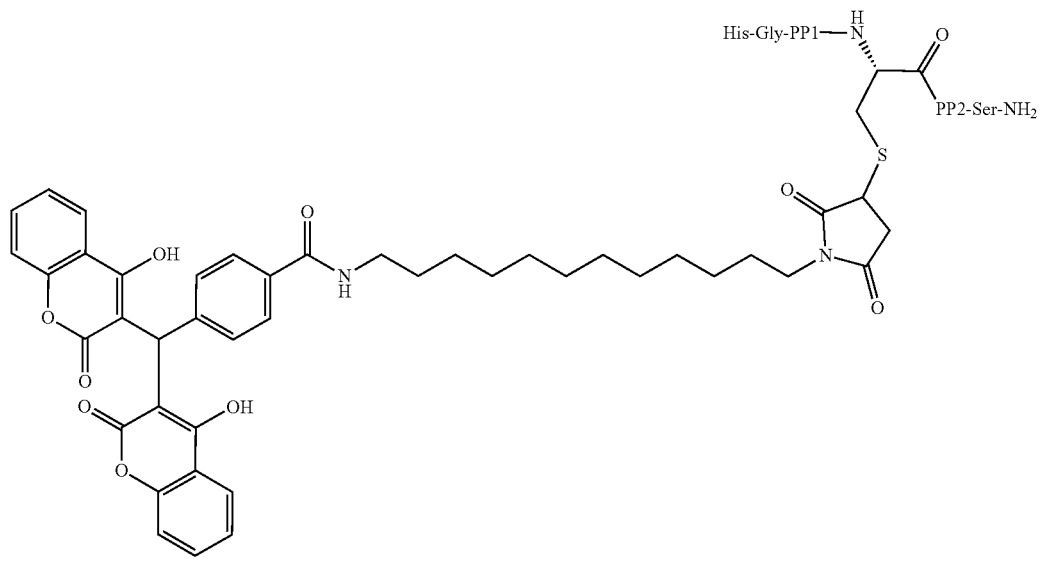

wherein PP1 is the polypeptide having the amino acid sequence shown as SEQ ID NO.:05 and PP2 is the polypeptide having the amino acid sequence shown as SEQ ID NO.:08, compound 28:
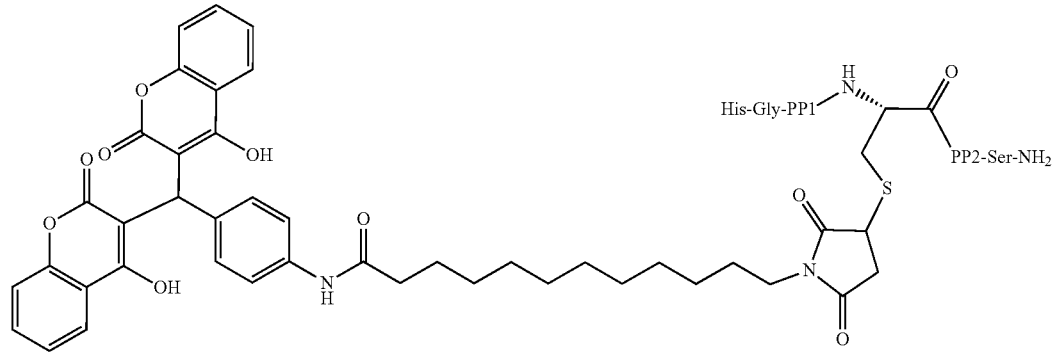
wherein PP1 is the polypeptide having the amino acid sequence shown as SEQ ID NO.:05 and PP2 is the polypeptide having the amino acid sequence shown as SEQ ID NO.:08,
compound 29:
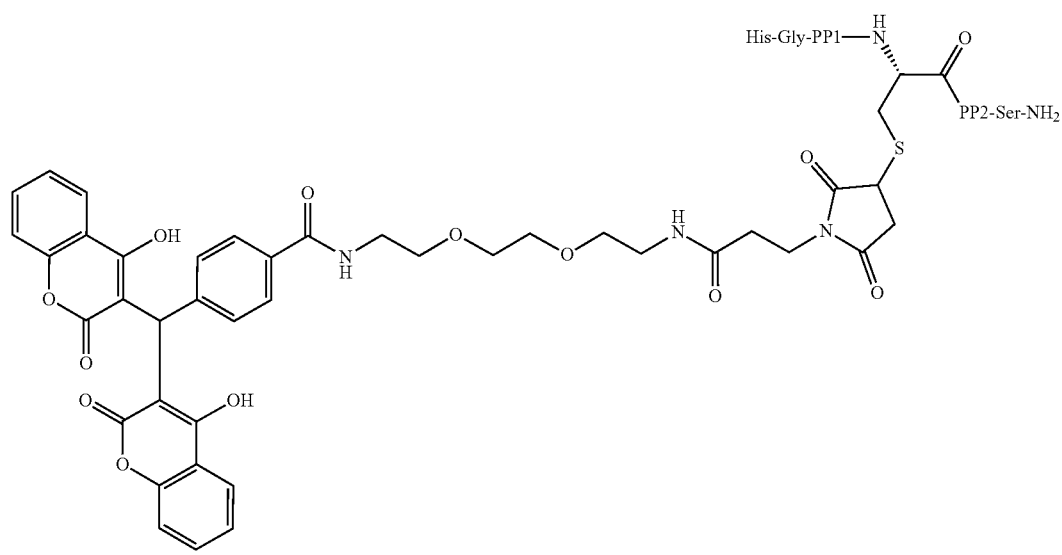
wherein PP1 is the polypeptide having the amino acid sequence shown as SEQ ID NO.:05 and PP2 is the polypeptide having the amino acid sequence shown as SEQ ID NO.:08, compound 30:
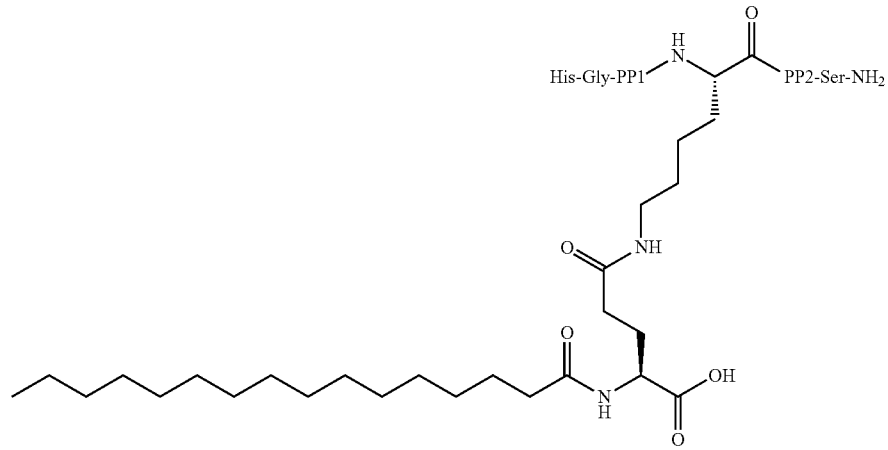
wherein PP1 is the polypeptide having the amino acid sequence shown as SEQ ID NO.:02 and PP2 is the polypeptide having the amino acid sequence shown as SEQ ID NO.:03,
compound 31:
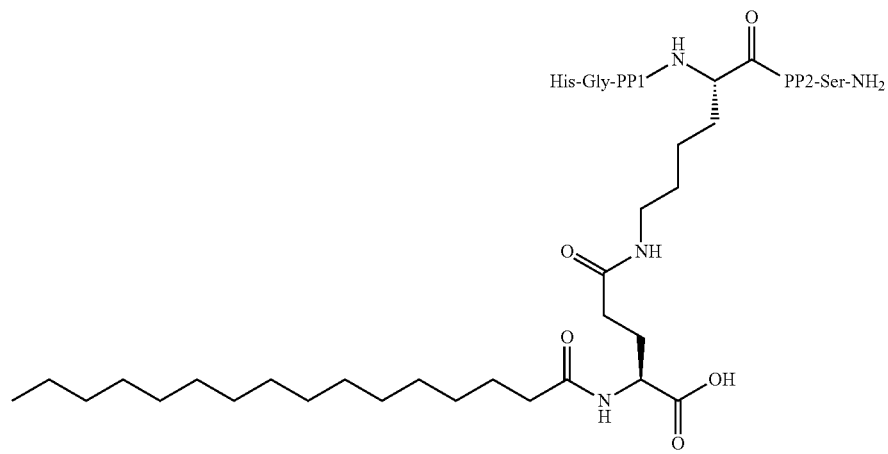
wherein PP1 is the polypeptide having the amino acid sequence shown as SEQ ID NO.:04 and PP2 is the polypeptide having the amino acid sequence shown as SEQ ID NO.:03, compound 32:
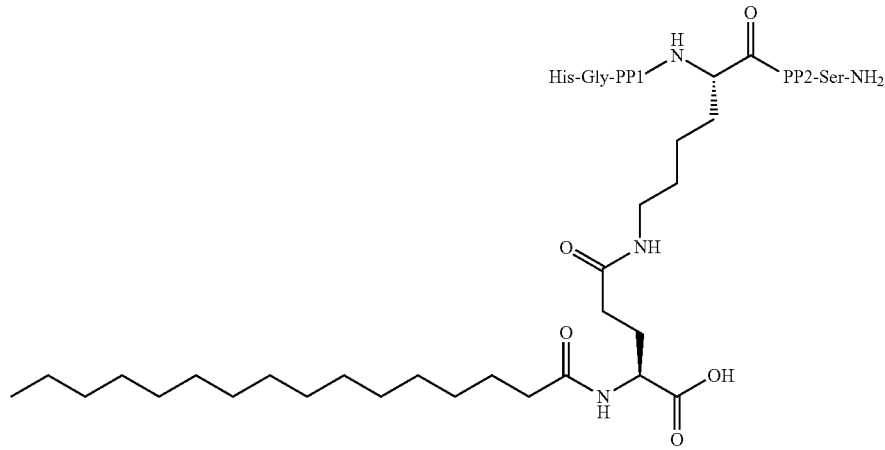
wherein PP1 is the polypeptide having the amino acid sequence shown as SEQ ID NO.:05 and PP2 is the polypeptide having the amino acid sequence shown as SEQ ID NO.:06,
compound 33:
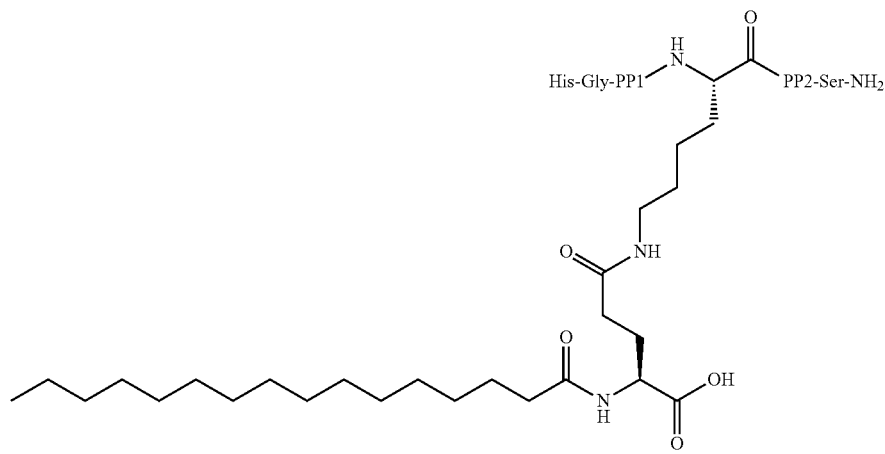
wherein PP1 is the polypeptide having the amino acid sequence shown as SEQ ID NO.:05 and PP2 is the polypeptide having the amino acid sequence shown as SEQ ID NO.:07, compound 34:
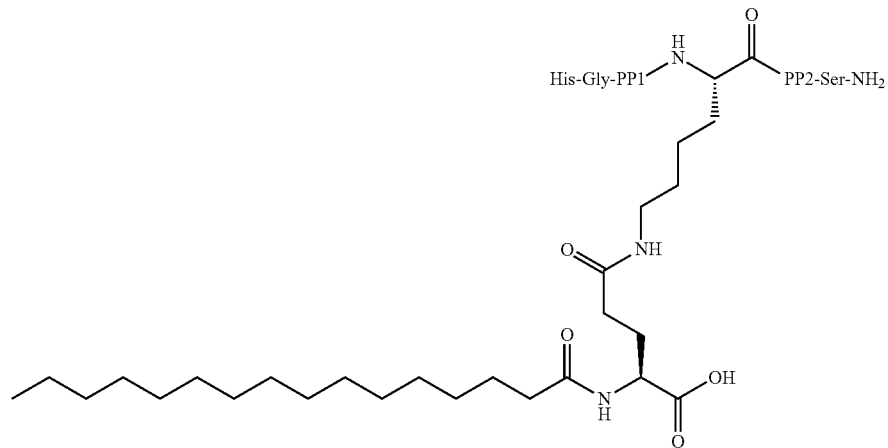
wherein PP1 is the polypeptide having the amino acid sequence shown as SEQ ID NO.:05 and PP2 is the polypeptide having the amino acid sequence shown as SEQ ID NO.:03,
compound 35:
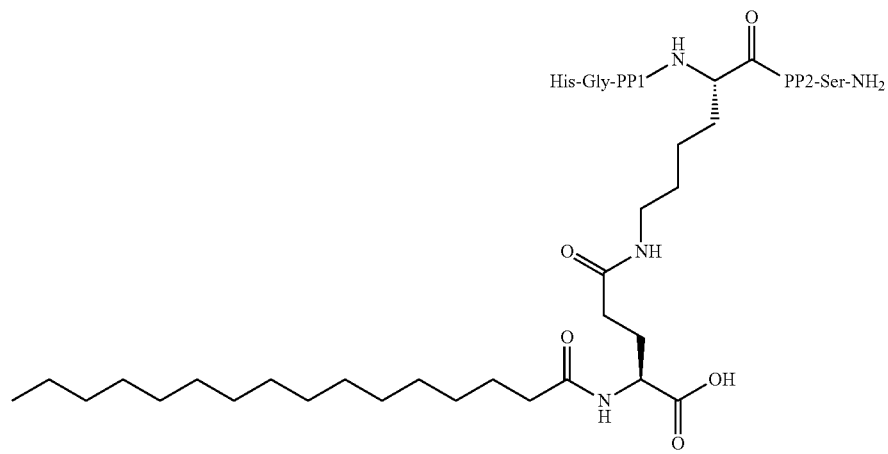
wherein PP1 is the polypeptide having the amino acid sequence shown as SEQ ID NO.:05 and PP2 is the polypeptide having the amino acid sequence shown as SEQ ID NO.:08, compound 36:
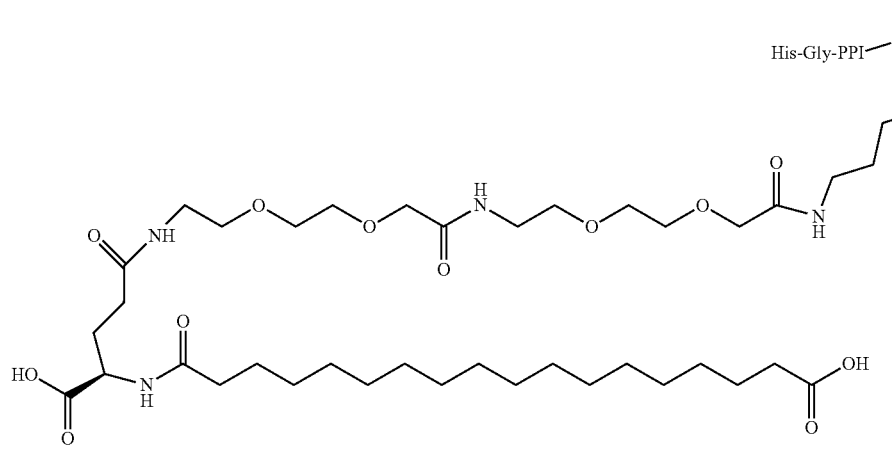
wherein PP1 is the polypeptide having the amino acid sequence shown as SEQ ID NO.:02 and PP2 is the polypeptide having the amino acid sequence shown as SEQ ID NO.:03,
compound 37:
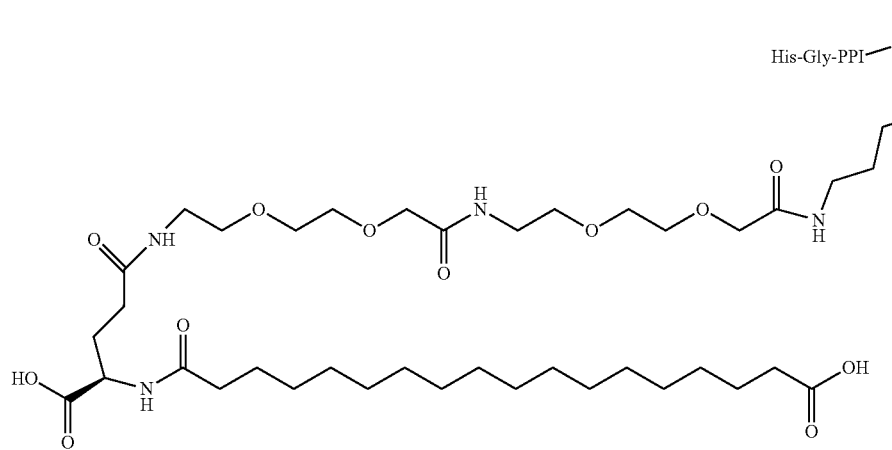
wherein PP1 is the polypeptide having the amino acid sequence shown as SEQ ID NO.:04 and PP2 is the polypeptide having the amino acid sequence shown as SEQ ID NO.:03,
compound 38:
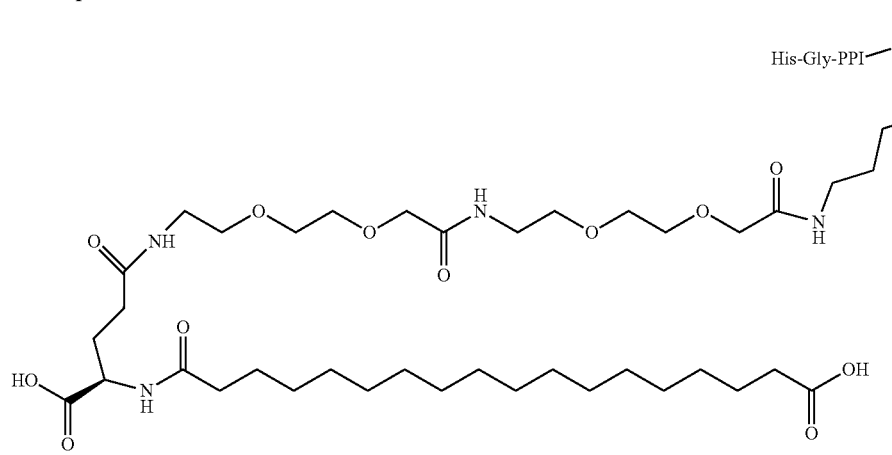

wherein PP1 is the polypeptide having the amino acid sequence shown as SEQ ID NO.:05 and PP2 is the polypeptide having the amino acid sequence shown as SEQ ID NO.:06, compound 39:

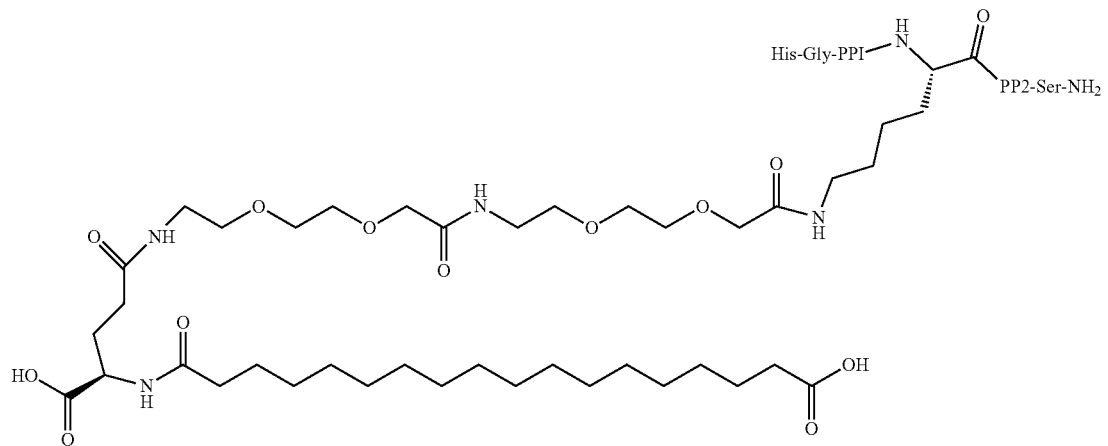

wherein PP1 is the polypeptide having the amino acid sequence shown as SEQ ID NO.:05 and PP2 is the polypeptide having the amino acid sequence shown as SEQ ID NO.:07, compound 40:

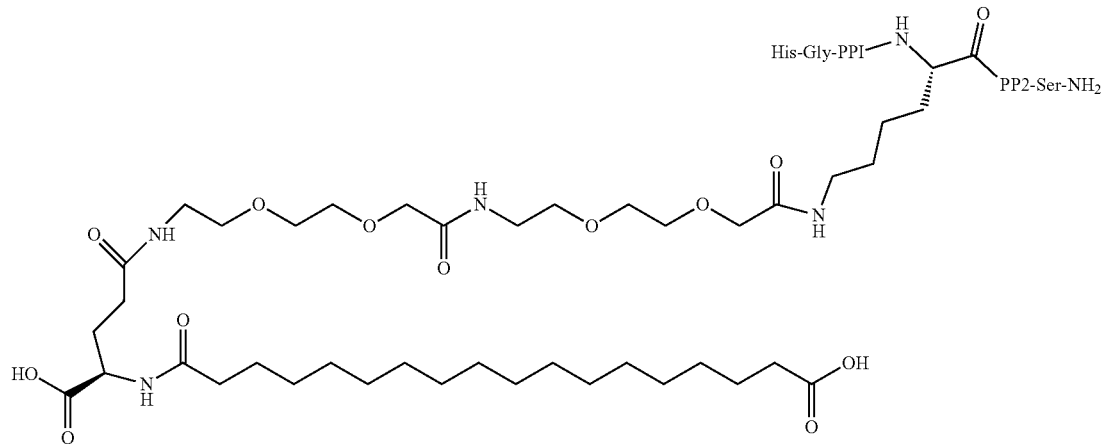

wherein PP1 is the polypeptide having the amino acid sequence shown as SEQ ID NO.:05 and PP2 is the polypeptide having the amino acid sequence shown as SEQ ID NO.:03, compound 41:

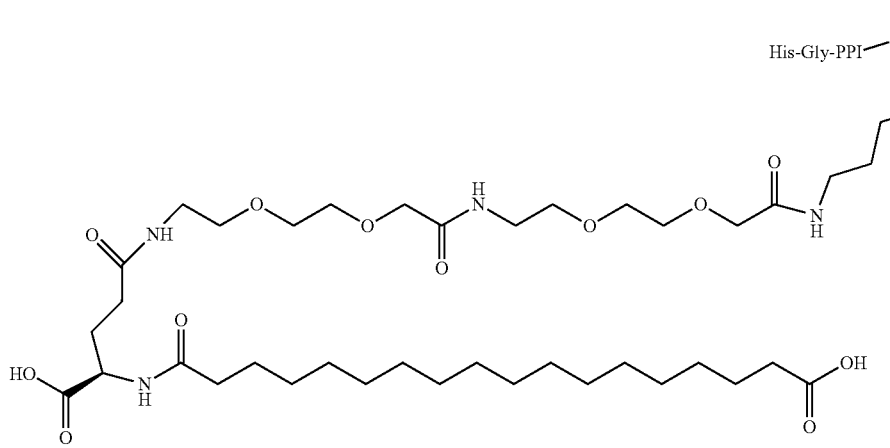

wherein PP1 is the polypeptide having the amino acid sequence shown as SEQ ID NO.:05 and PP2 is the polypeptide having the amino acid sequence shown as SEQ ID NO.:08, compound 42:

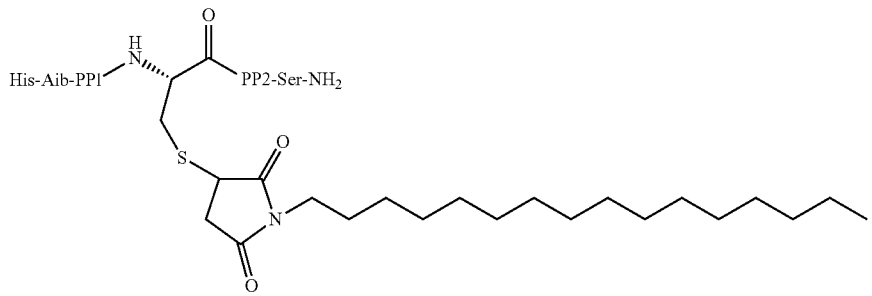

wherein PP1 is the polypeptide having the amino acid sequence shown as SEQ ID NO.:05 and PP2 is the polypeptide having the amino acid sequence shown as SEQ ID NO.:03, compound 43:

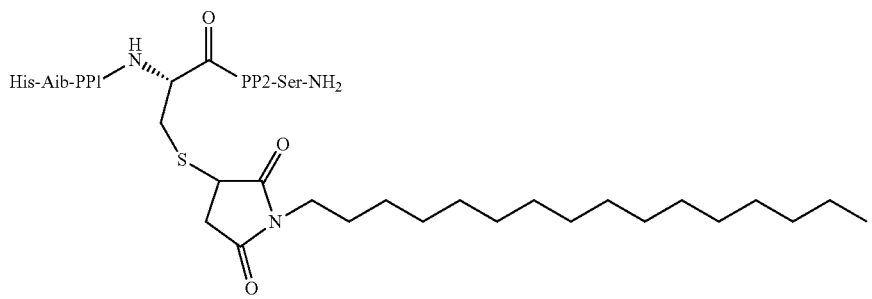

wherein PP1 is the polypeptide having the amino acid sequence shown as SEQ ID NO.:05 and PP2 is the polypeptide having the amino acid sequence shown as SEQ ID NO.:08, compound 44:
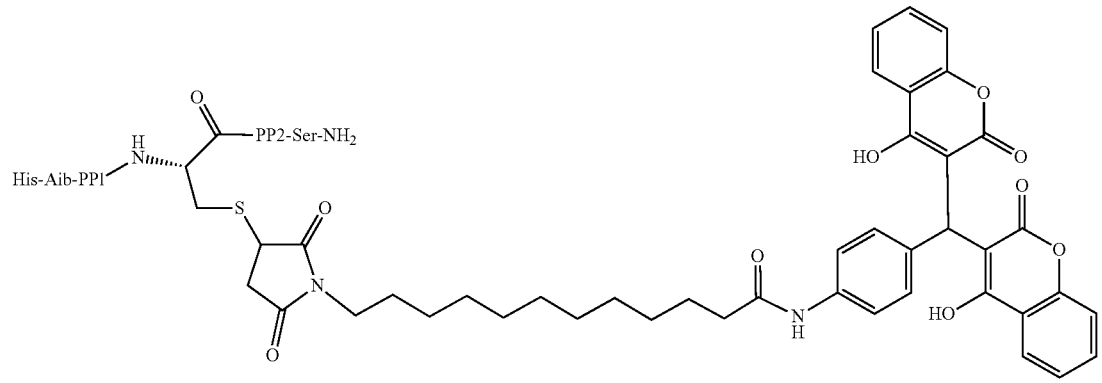
wherein PP1 is the polypeptide having the amino acid sequence shown as SEQ ID NO.:05 and PP2 is the polypeptide having the amino acid sequence shown as SEQ ID NO.:03,
compound 45:
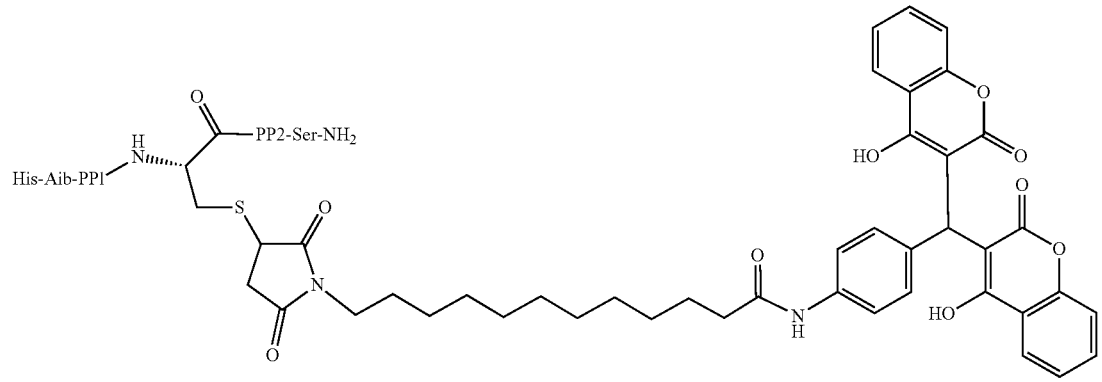
wherein PP1 is the polypeptide having the amino acid sequence shown as SEQ ID NO.:05 and PP2 is the polypeptide having the amino acid sequence shown as SEQ ID NO.:08,
compound 46:
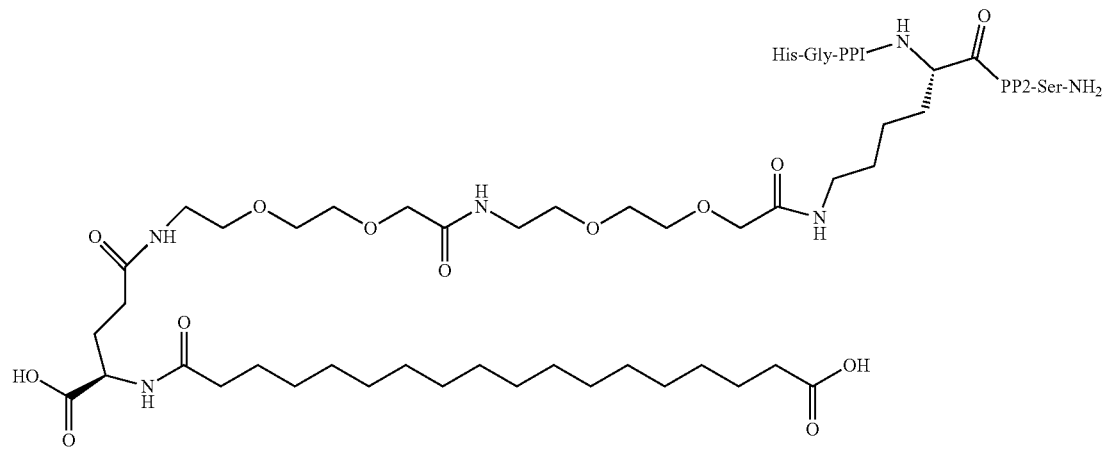

wherein PP1 is the polypeptide having the amino acid sequence shown as SEQ ID NO.:05 and PP2 is the polypeptide having the amino acid sequence shown as SEQ ID NO.:03, compound 47:

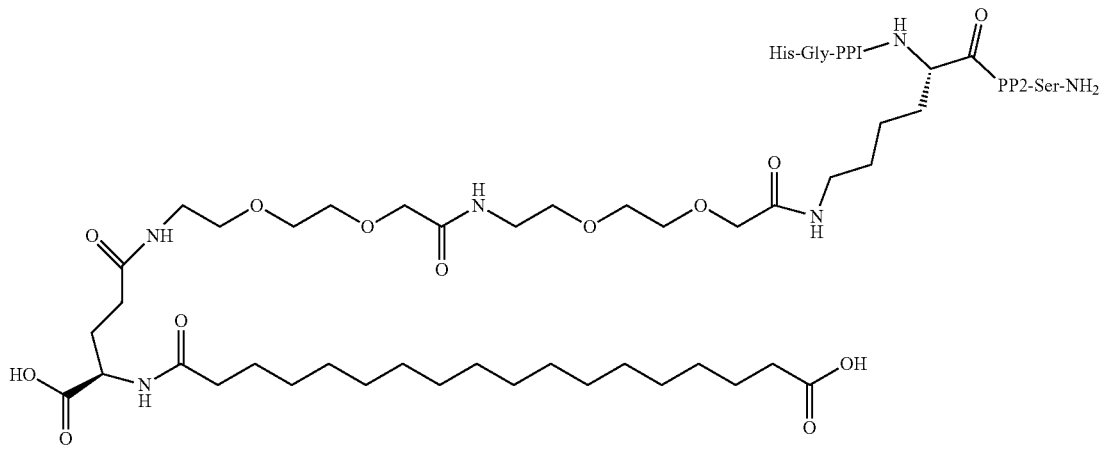

wherein PP1 is the polypeptide having the amino acid sequence shown as SEQ ID NO.:05 and PP2 is the polypeptide having the amino acid sequence shown as SEQ ID NO.:08, compound 48:

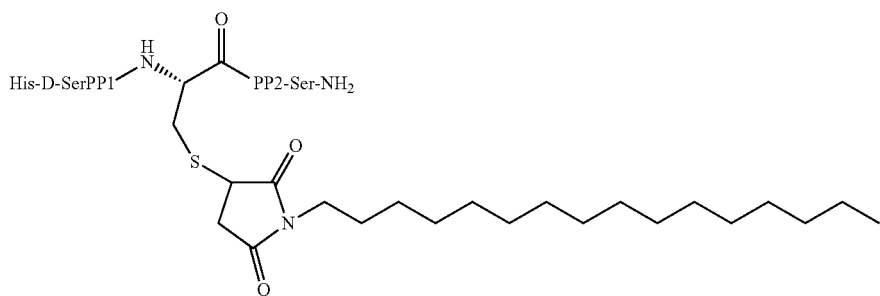

wherein PP1 is the polypeptide having the amino acid sequence shown as SEQ ID NO.:05 and PP2 is the polypeptide having the amino acid sequence shown as SEQ ID NO.:03, compound 49:

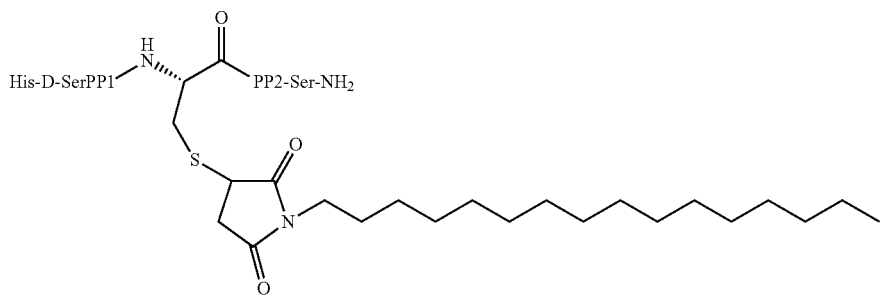

wherein PP1 is the polypeptide having the amino acid sequence shown as SEQ ID NO.:05 and PP2 is the polypeptide having the amino acid sequence shown as SEQ ID NO.:08, compound 50:

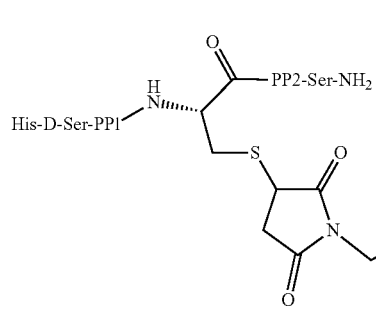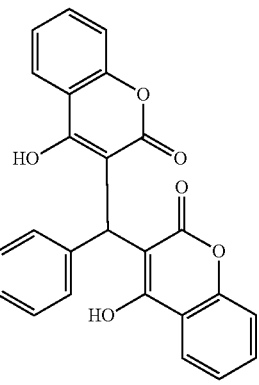

wherein PP1 is the polypeptide having the amino acid sequence shown as SEQ ID NO.:05 and PP2 is the polypeptide having the amino acid sequence shown as SEQ ID NO.:03, compound 51:

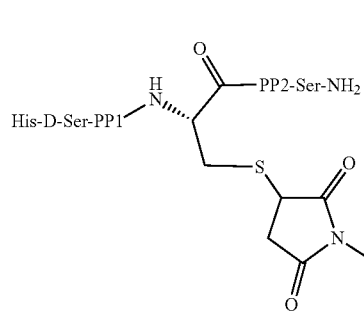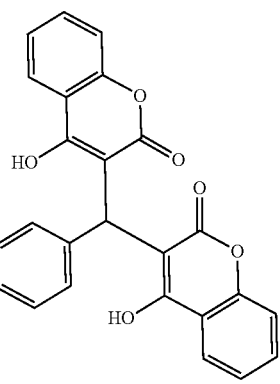

wherein PP1 is the polypeptide having the amino acid sequence shown as SEQ ID NO.:05 and PP2 is the polypeptide having the amino acid sequence shown as SEQ ID NO.:08, compound 52:
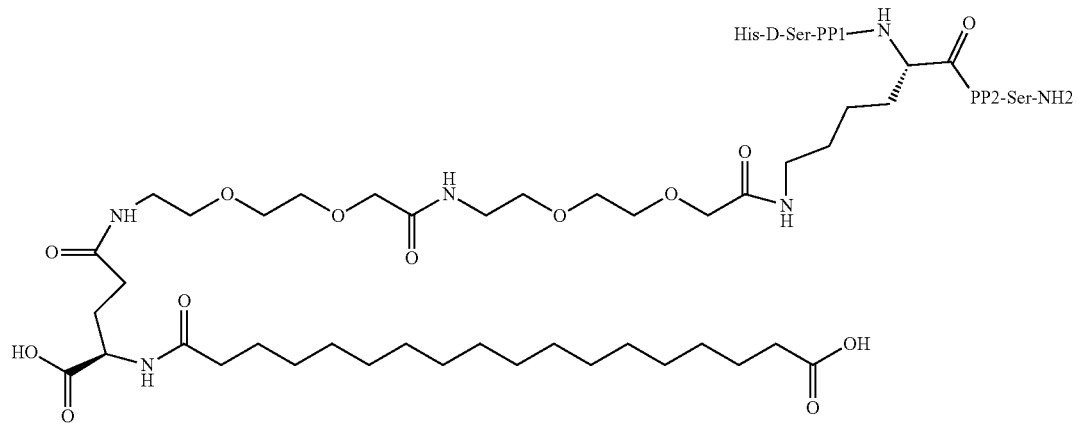
wherein PP1 is the polypeptide having the amino acid sequence shown as SEQ ID NO.:05 and PP2 is the polypeptide having the amino acid sequence shown as SEQ ID NO.:03,
compound 53:
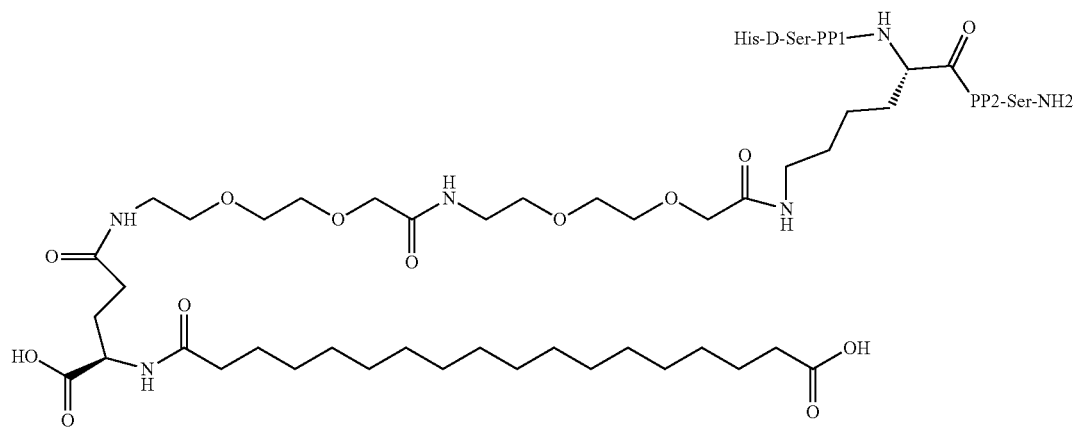
wherein PP1 is the polypeptide having the amino acid sequence shown as SEQ ID NO.:05 and PP2 is the polypeptide having the amino acid sequence shown as SEQ ID NO.:08,
compound 54:
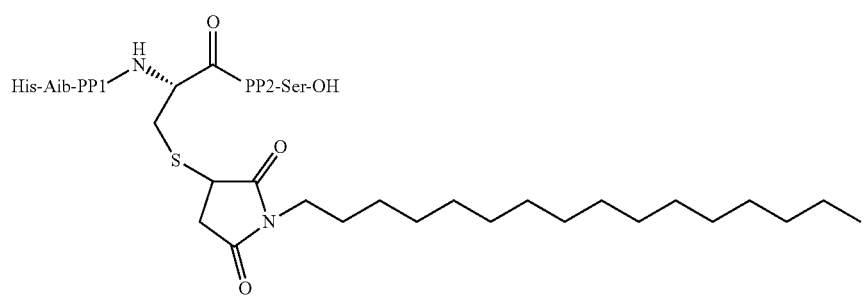

wherein PP1 is the polypeptide having the amino acid sequence shown as SEQ ID NO.:05 and PP2 is the polypeptide having the amino acid sequence shown as SEQ ID NO.:03, compound 55:

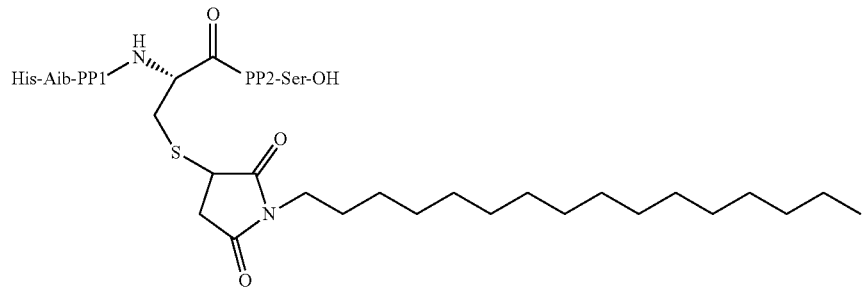

wherein PP1 is the polypeptide having the amino acid sequence shown as SEQ ID NO.:05 and PP2 is the polypeptide having the amino acid sequence shown as SEQ ID NO.:08, compound 56:

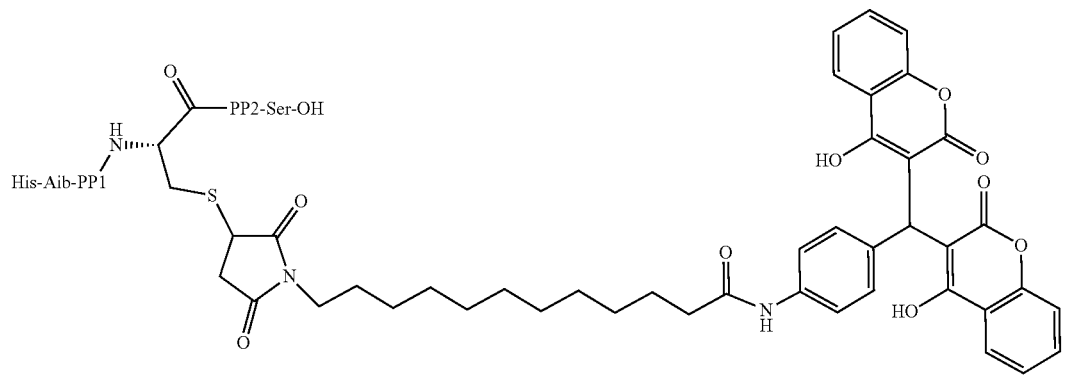

wherein PP1 is the polypeptide having the amino acid sequence shown as SEQ ID NO.:05 and PP2 is the polypeptide having the amino acid sequence shown as SEQ ID NO.:03, compound 57:

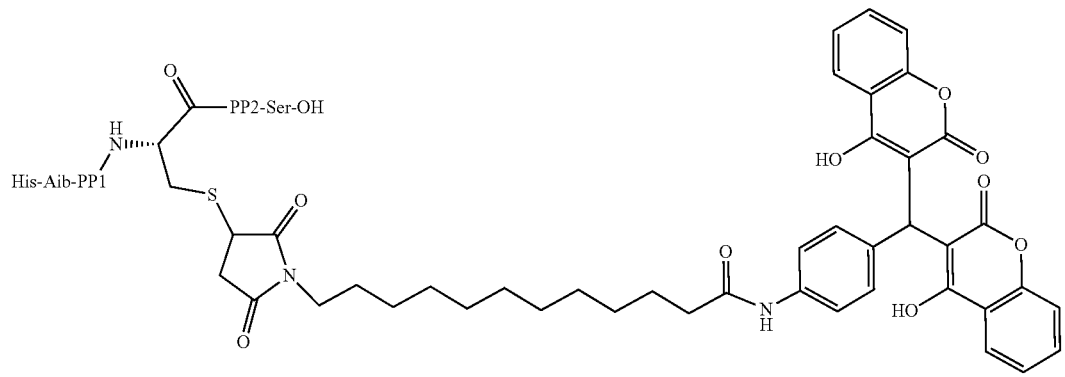

wherein PP1 is the polypeptide having the amino acid sequence shown as SEQ ID NO.:05 and PP2 is the polypeptide having the amino acid sequence shown as SEQ ID NO.:08, compound 58:

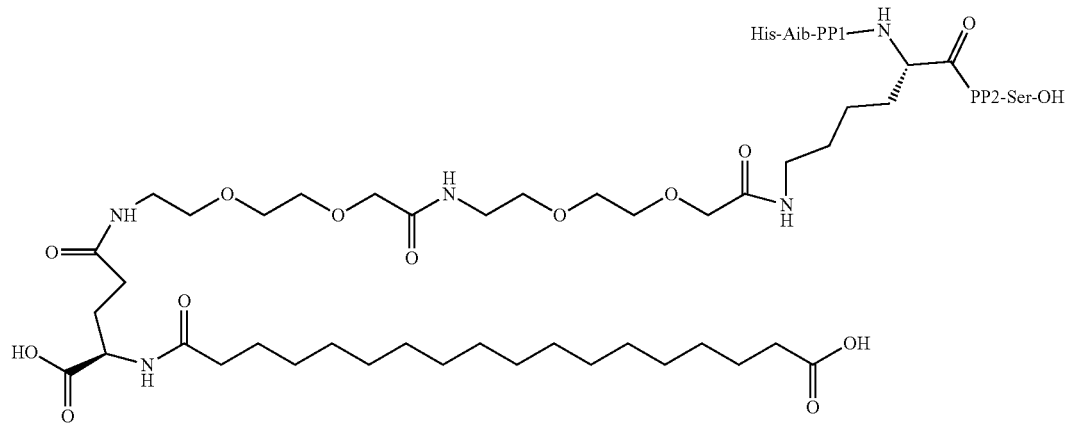

wherein PP1 is the polypeptide having the amino acid sequence shown as SEQ ID NO.:05 and PP2 is the polypeptide having the amino acid sequence shown as SEQ ID NO.:03, and compound 59:

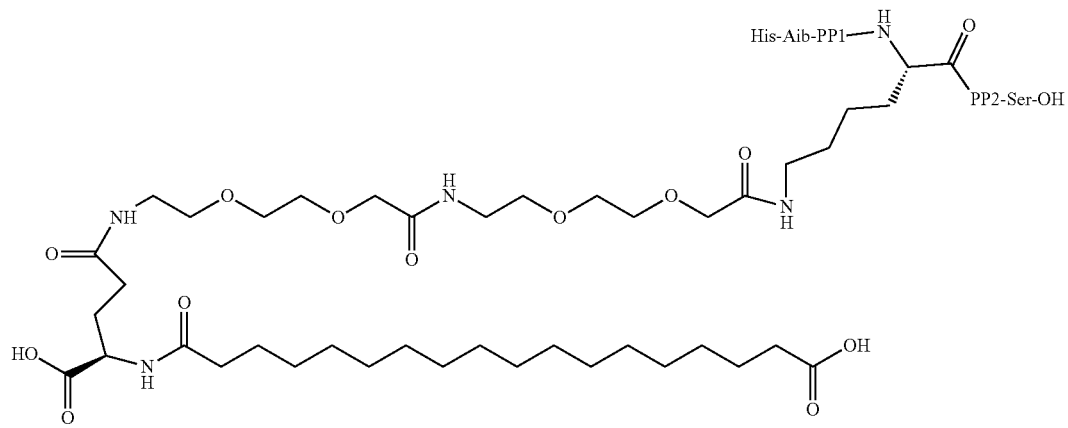

wherein PP1 is the polypeptide having the amino acid sequence shown as SEQ ID NO.:05 and PP2 is the polypeptide having the amino acid sequence shown as SEQ ID NO.:08.

A pharmaceutically acceptable salt. The salt is formed by the compound with hydrochloric acid, hydrobromic acid, hydroiodic acid, sulfuric acid, pyrosulfuric acid, phosphoric acid, nitric acid, methanesulfonic acid, ethanesulfonic acid, benzenesulfonic acid, P-toluenesulfonic acid, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid.

In a second aspect, the present invention provides a pharmaceutical composition, including a therapeutically effective amount of at least one of the above compounds and a pharmaceutically acceptable salt of the compound, or a pharmaceutically acceptable carrier or diluent of the compound. At the same time, the present invention further provides application of the above compound and the pharmaceutically acceptable salt of the compound, or the pharmaceutically acceptable carrier or diluent of the compound to preparation of a medicine for treating and preventing diabetes.

In certain implementations of the above second aspect, compared with an OXM prototype, the class of hypoglycemic polypeptides has an improved agonistic activity on GLP-1R, maintains a moderate GCGR agonistic activity, and achieves an excellent hypoglycemic effect. In the body of a diabetic model mouse, after once administration, the blood glucose stabilization time exceeds 40 h. At the same time, this class of hypoglycemic polypeptides further has a good weight gain slowing activity.

In certain implementations of the above second aspect, compared with an OXM prototype, the class of hypoglycemic polypeptides has an improved agonistic activity on GLP-1R, maintains a moderate GCGR agonistic activity, and achieves an excellent hypoglycemic effect. In the body of a diabetic model mouse, after once administration, the blood glucose stabilization time exceeds 60 h. At the same time, this class of hypoglycemic polypeptides further has a good weight gain slowing activity.

In a third aspect, the present invention further provides a preparation method of the above compound. The above target compound is efficiently and fast synthesized by using a solid-phase synthesis strategy.

The present invention further provides a preparation method and an intermediate of this class of hypoglycemic polypeptides. According to the preparation method of the class of hypoglycemic polypeptides provided by the present invention, each amino acid of a main chain of the class of hypoglycemic polypeptides is gradually coupled by a solid-phase synthesis method to obtain peptide resin linked to the main chain, and fatty acid small molecules are coupled to a side chain of L-Lysine at position 16 to obtain the hypoglycemic polypeptide. The method has the advantages of simple synthesis steps, high coupling efficiency and easy purification, and is favorable for the industrialized production of this class of hypoglycemic polypeptides.

In the above third aspect, the present invention adopts the following technical solution:

The present invention provides a preparation method of a hypoglycemic polypeptide, including the following two strategies:

strategy 1: mode of synthesizing a compound by linking Cys in a peptide chain with maleimide:

step 1: taking and activating resin, and then gradually coupling amino acids, so as to obtain first peptide resin;

step 2: taking the first peptide resin, and performing lysis and purification to obtain a pure peptide chain; and step 3: conjugating thiol of Cys in the pure peptide chain with a fatty acid chain or a coumarin small molecule linked with a maleimide linking arm to obtain the compound;

strategy 2: mode of synthesizing by linking Lys in the peptide chain with a small-molecular fatty acid chain:

step 1: taking and activating resin, and then gradually coupling amino acids, so as to obtain first peptide resin;

step 2: taking the first peptide resin, and coupling a fatty acid chain small molecule of Formula I or Formula II to a Lys side chain to obtain second peptide resin; and step 3: taking the second peptide resin, and performing lysis and purification to obtain the compound.

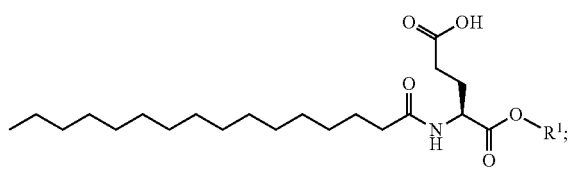
Formula I

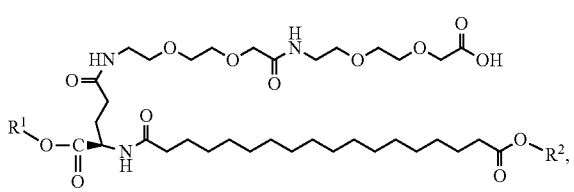
Formula II wherein $R^1$ is selected from tBu, Dmab, or Bzl; and
$R^2$ is selected from methyl, ethyl, tert-butyl, and benzhydryl.

A Lys side chain protecting group coupled to the fatty acid chain small molecule of Formula I or Formula II is selected from Fmoc, Boc, Dde, or ivDde.

Preferably, in the preparation method provided by the present invention, the resin in step 1 is Rink Amide AM Resin, Fmoc-Rink amide-MBHA or Wang Resin. In some embodiments of the present invention, in the preparation method provided by the present invention, the resin in step 1 is specifically Fmoc-Rink amide-MBHA or Wang Resin.

Preferably, in the preparation method provided by the present invention, a lysis reagent used for lysis is a mixture of TFA, thioanisole, anisole and EDT. In some embodiments of the present invention, in the preparation method provided by the present invention, a volume ratio of the TFA, thioanisole, anisole and EDT in the reagent used for lysis in step 3 is (85 to 92):(4 to 6):(2 to 3):(2 to 6). In some other embodiments of the present invention, in the preparation method provided by the present invention, a volume ratio of the TFA, thioanisole, anisole and EDT in the reagent used for lysis in step 3 is 90:5:3:2.

In some other embodiments of the present invention, in the preparation method provided by the present invention, a method used for purification is a chromatographic separation method. In some other embodiments of the present invention, in the preparation method provided by the present invention, a chromatographic column used for purification is a C18 column.

Beneficial Effects of the Present Invention:

1. The compound provided by the present invention has obvious hypoglycemic and weight losing effects and stable chemical properties, and the activity is obviously superior to that of prototype peptide OXM.

2. The hypoglycemic effect of the partial compound provided by the present invention can maintain 40 h or above, and the effect is obviously improved in comparison with that of endogenic GLP-1 (half-life period: 2-3 min) or a marketed medicine exenatide (half-life period: 2.4 h).

3. The purity of a peptide chain crude product of a solid-phase synthesis OXM hybrid peptide using an orthogonal protection strategy is higher than 85%, and is greatly improved in comparison with that of a conventional synthesis method, so that the subsequent purification work is convenient.

4. The method uses the solid-phase synthesis method, so that the synthesis cost of the OXM hybrid peptide is low.

The coupling efficiency is high, so that protection amino acids only averagely need twice over dose while 4 to 5 times of over dose of amino acids is needed in the conventional synthesis method, and the cost is greatly reduced.

5. The method for synthesizing the OXM hybrid peptide by using a Fmoc/tBu orthogonal protection solid-phase synthesis strategy is easy in automatic and large-scale production, so that the method is more suitable for industrialized production.

Therefore, the OXM hybrid peptide prepared by a solid-phase synthesis technology provided by the present invention has the advantages of good hypoglycemic and weight gain slowing activity, long medicine effect duration, high yield, short synthesis period, easy crude product purification and low production cost, and is easy in industrialized automatic production. The prepared OXM hybrid peptide is suitable to be used as an active ingredient of a medicine for treating diabetes and obesity.

DETAILED DESCRIPTION OF THE INVENTION

Figure 1:
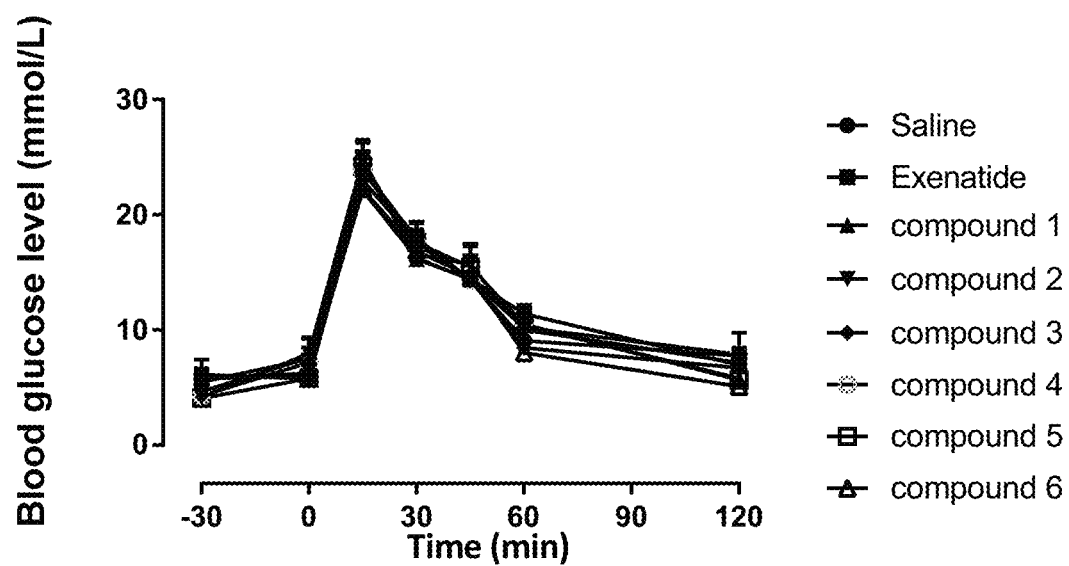
FIG. 1 is a result of a second day glucose tolerance test of OXM hybrid peptides compound 1-6.
Figure 2:
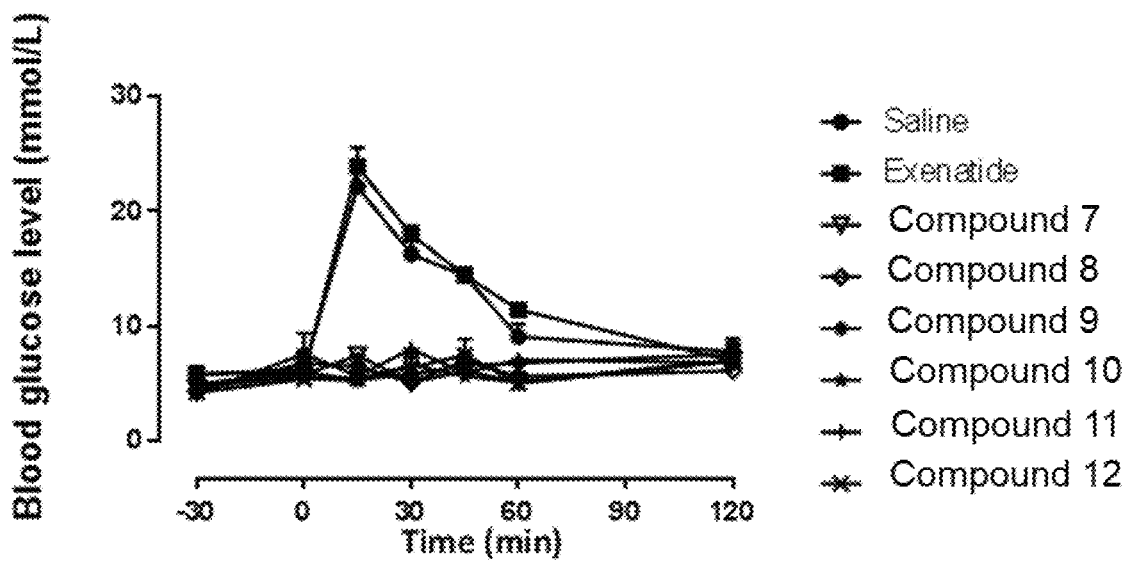
FIG. 2 is a result of a second day glucose tolerance test of OXM hybrid peptides compound 7-12.
Figure 3:
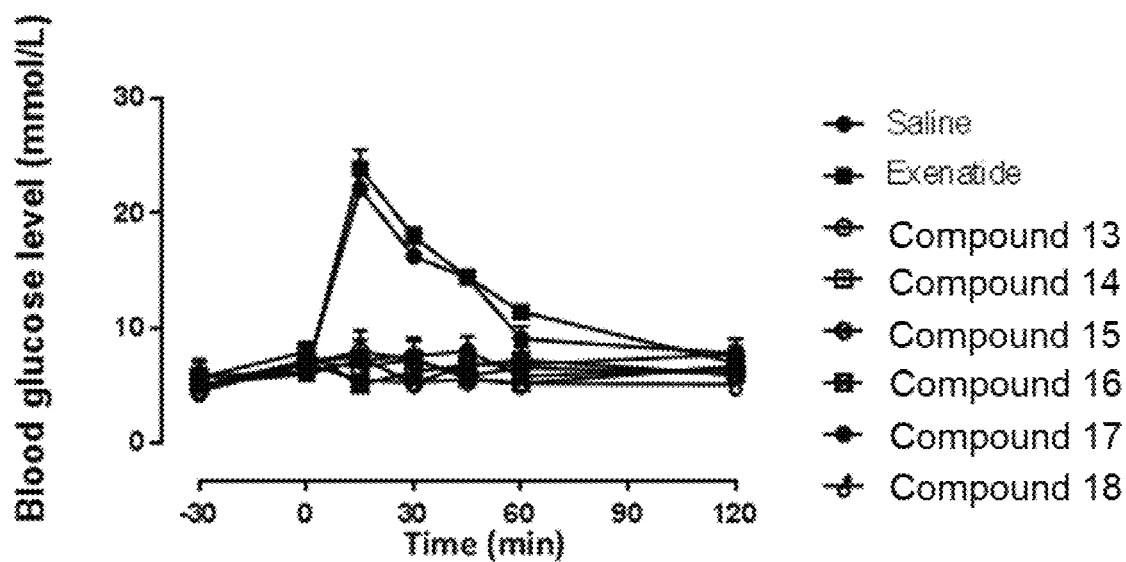
FIG. 3 is a result of a second day glucose tolerance test of OXM hybrid peptides compound 13-18.
Figure 4:
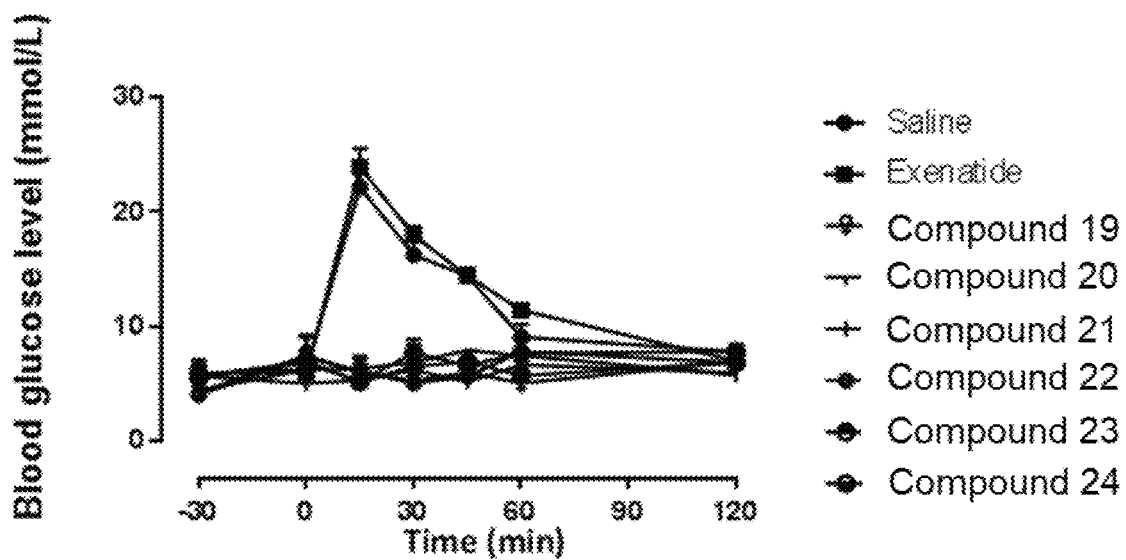
FIG. 4 is a result of a second day glucose tolerance test of OXM hybrid peptides compound 19-24.

The following abbreviations are used throughout this specification:

| Abbreviation | Full name |
| --- | --- |
| DCM | Dichloromethane |
| NMP | N-methyl pyrrolidone |
| HBTU | O-benzotriazol-1-yl-N,N,N',N'-tetramethyluronium hexafluorophosphate |
| HOBt | 1-hydroxybenzotriazole |
| DIEA/DIPEA | N,N'-ethyldiisopropylamine |
| Fmoc | N-9-fluorenylmethyloxycarbonyl |
| ESI-MS | Electrospray ionization mass spectrometry |
| EDT | Ethanedithiol |
| HPLC | High performance liquid chromatography |
| TFA | Trifluoroacetic acid |
| tBu | Tert-butyl |
| Boc | Tert-butoxycarbonyl |
| EDC•HCl | 1-(3-dimethylaminopropyl)-3-ethylcarbodiimide hydrochloride |
| DMAP | 4-dimethylaminopyridine |
| DIC | N,N-diisopropylcarbodiimide |
| $Na_2SO_4$ | Sodium sulphate |
| DMSO | Dimethyl sulfoxide |
| $K_2CO_3$ | Potassium carbonate |
| HCl | Hydrogen chloride |
| Pd/C | Palladium carbon |
| Dde | 1-(4,4-dimethyl-2,6-dioxacyclohexylidene methylene)-ethyl |
| Fmoc-AEEA | [2-[2-(Fmoc-amino)ethoxy]ethoxy]acetic acid |
| OtBu | Oxy-tert-butyl |
| Dmab | 4-{N-[1-(4,4-dimethyl-2,6-dioxocyclohexyl)-3-methyl butyl]amino}benzyl |
| Bzl | Benzyl |
| ivDde | 1-(4,4-dimethyl-2,6-dioxocyclohexylidene)-3-methyl butyl |

The present invention is illustrated through the following embodiments. However, these embodiments are not intended to limit the interpretation of the present invention in any way.

Embodiment 1

Solid-Phase Synthesis of
compound 1: His-Gly-PP11-Cys-PP2-Ser-NH2 wherein PP1 is the polypeptide having the amino acid sequence shown as SEQ ID NO.:02 and PP2 is the polypeptide having the amino acid sequence shown as SEQ ID NO.:03

(1) Swelling of Resin 50 mg of Fmoc-Rink amide-MBHA Resin (substitution degree: 0.4 mmol/g) was weighed, and was swelled with 7 mL of DCM for 30 min. DCM was removed through suction filtration. Then, the resin was swelled with 10 mL of NMP for 30 min, and was cleanly flushed respectively with 7 mL of NMP and 7 mL of DCM.

(2) Removal of Fmoc Protecting Group

The swelled resin was put into a reactor. A 25% piperidine/NMP (V/V) solution containing 0.1 M HOBt was added into the resin to remove Fmoc. After the reaction was completed, the resin was cleanly washed with NMP. Resin with initially linked Fmoc protecting groups removed was obtained.

(3) Synthesis of Fmoc-Ser(tBu)-Rink amide-MBHA Resin

Fmoc-Ser(tBu)-OH (15.4 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin obtained in the previous step to react for 2 h. After the reaction was completed, reaction liquid was filtered away, and the resin was washed with 7 mL of DCM and 7 mL of NMP 3 times.

(4) Elongation of Peptide Chain

According to a sequence of a peptide chain, corresponding amino acids were sequentially linked by repeating the above deprotection and coupling steps. The corresponding amino acids were sequentially linked until the synthesis of the peptide chain was completed. The resin linked with compound 1 was obtained.

(5) Lysis of Polypeptide on Resin

The obtained resin linked with compound 1 was put into a reaction bottle. 10 mL of a lysis agent Reagent K (TFA/thioanisole/water/phenol/EDT, 82.5:5:5:5:2.5, V/V) was respectively added. Firstly, shaking was performed at 0° C. for 30 min, and then, reaction was performed at a normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 77.1 mg of the crude product was finally obtained. The yield was 90.2%.

The reaction was monitored by using HPLC. The chromatographic conditions were as follows: C18 column (150 mm×4.6 mm, 5 μm); mobile phase A: 0.1% TFA/water (V/V), and mobile phase B: 0.1% TFA/acetonitrile (V/V); mobile phase gradient: mobile phase B 35%-85%, 20 min; flow rate: 1 mL/min; column temperature: 40° C.; and detection wavelength: 214 nm. After the reaction was completed, purification was performed by preparative liquid chromatography. The chromatographic conditions were as follows: C18 column (320 mm×28 mm, 5 μm); mobile phase A: 0.1% TFA/water (V/V), and mobile phase B: 0.1% TFA/acetonitrile (V/V); mobile phase gradient: mobile phase B 40%-90%, 20 min; flow rate: 6 mL/min; and detection wavelength: 214 nm. A collected solution was freeze-dried to obtain 28.5 mg of a pure product. A theoretical relative molecular mass was 4273.7. ESI-MS m/z: Calcd. $[M+3H]^{3+}$ 1425.6, $[M+4H]^{4+}$ 1069.4; Found $[M+3H]^{3+}$ 1425.1, $[M+4H]^{4+}$ 1069.0.

Embodiment 2 compound 2: His-Gly-PP1-Cys-PP2-Ser-NH2 wherein PP1 is the polypeptide having the amino acid sequence shown as SEQ ID NO.:04 and PP2 is the polypeptide having the amino acid sequence shown as SEQ ID NO.:03

A synthesis method was the same as that of Embodiment 1. The collected solution was freeze-dried to obtain 29.2 mg of a pure product. A theoretical relative molecular mass was 4269.7. ESI-MS m/z: Calcd. $[M+3H]^{3+}$ 1424.2, $[M+4H]^{4+}$ 1068.4; Found $[M+3H]^{3+}$ 1424.8, $[M+4H]^{4+}$ 1068.1.

Embodiment 3 compound 3: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:06

A synthesis method was the same as that of Embodiment 1. The collected solution was freeze-dried to obtain 27.6 mg of a pure product. A theoretical relative molecular mass was 4228.6. ESI-MS m/z: Calcd. $[M+3H]^{3+}$ 1410.5, $[M+4H]^{4+}$ 1058.2; Found $[M+3H]^{3+}$ 1410.0, $[M+4H]^{4+}$ 1058.2.

Embodiment 4 compound 4: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:07

A synthesis method was the same as that of Embodiment 1. The collected solution was freeze-dried to obtain 29.4 mg of a pure product. A theoretical relative molecular mass was 4283.7. ESI-MS m/z: Calcd. $[M+3H]^{3+}$ 1428.9, $[M+4H]^{4+}$ 1071.9; Found $[M+3H]^{3+}$ 1429.0, $[M+4H]^{4+}$ 1072.0.

Embodiment 5 compound 5: His-Gly-PP1-Cys-PP2-Ser-$NH_2$ wherein PP1 is the polypeptide having the amino acid sequence shown as SEQ ID NO.:05 and PP2 is the polypeptide having the amino acid sequence shown as SEQ ID NO.:03

A synthesis method was the same as that of Embodiment 1. The collected solution was freeze-dried to obtain 27.6 mg of a pure product. A theoretical relative molecular mass was 4253.7. ESI-MS m/z: Calcd. $[M+3H]^{3+}$ 1418.9, $[M+4H]^{4+}$ 1064.4; Found $[M+3H]^{3+}$ 1419.5, $[M+4H]^{4+}$ 1064.5.

Embodiment 6 compound 6: His-Gly-PP1-Cys-PP2-Ser-$NH_2$ wherein PP1 is the polypeptide having the amino acid sequence shown as SEQ ID NO.:05 and PP2 is the polypeptide having the amino acid sequence shown as SEQ ID NO.:08

A synthesis method was the same as that of Embodiment 1. The collected solution was freeze-dried to obtain 28.9 mg of a pure product. A theoretical relative molecular mass was 4256.6. ESI-MS m/z: Calcd. $[M+3H]^{3+}$ 1419.9, $[M+4H]^{4+}$ 1065.2; Found $[M+3H]^{3+}$ 1420.1, $[M+4H]^{4+}$ 1065.5.

Embodiment 7

Solid-phase synthesis of compound 7:

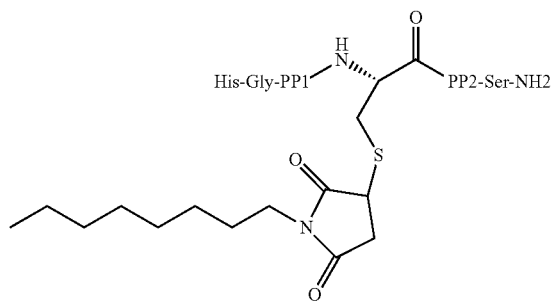

wherein PP1 is the polypeptide having the amino acid sequence shown as SEQ ID NO.:02 and PP2 is the polypeptide having the amino acid sequence shown as SEQ ID NO.:03

A polypeptide chain of compound 1 was dissolved with DMSO and prepared into a solution about 10 mg/mL. N-octane maleimide was also dissolved in DMSO. After mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 29.4 mg of a pure product. A theoretical relative molecular mass was 4483.0. ESI-MS m/z: Calcd. $[M+3H]^{3+}$ 1495.3, $[M+4H]^{4+}$ 1121.1; Found $[M+3H]^{3+}$ 1495.8, $[M+4H]^{4+}$ 1121.2.

Embodiment 8

Solid-phase synthesis of compound 8:

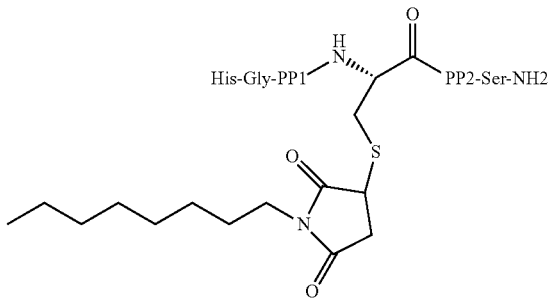

wherein PP1 is the polypeptide having the amino acid sequence shown as SEQ ID NO.:04 and PP2 is the polypeptide having the amino acid sequence shown as SEQ ID NO.:03, A polypeptide chain of compound 2 was dissolved with DMSO and prepared into a solution about 10 mg/mL. N-octane maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 27.6 mg of a pure product. A theoretical relative molecular mass was 4479.0. ESI-MS m/z: Calcd. $[M+3H]^{3+}$ 1494.0, $[M+4H]^{4+}$ 1120.7; Found $[M+3H]^{3+}$ 1494.0, $[M+4H]^{4+}$ 1120.9.

Embodiment 9

Solid-phase synthesis of compound 9:

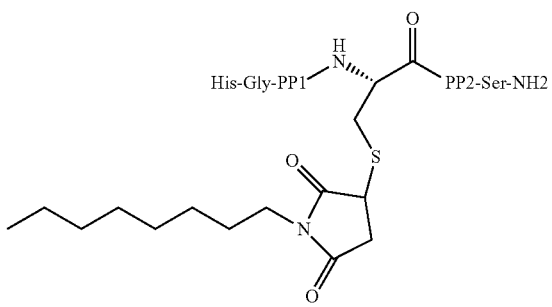

wherein PP1 is the polypeptide having the amino acid sequence shown as SEQ ID NO.:05 and PP2 is the polypeptide having the amino acid sequence shown as SEQ ID NO.:06

A polypeptide chain of compound 3 was dissolved with DMSO and prepared into a solution about 10 mg/mL. N-octane maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.1 mg of a pure product. A theoretical relative molecular mass was 4437.9. ESI-MS m/z: Calcd. $[M+3H]^{3+}$ 1480.3, $[M+4H]^{4+}$ 1110.5; Found $[M+3H]^{3+}$ 1480.0, $[M+4H]^{4+}$ 1110.3.

Embodiment 10

Solid-phase synthesis of compound 10:

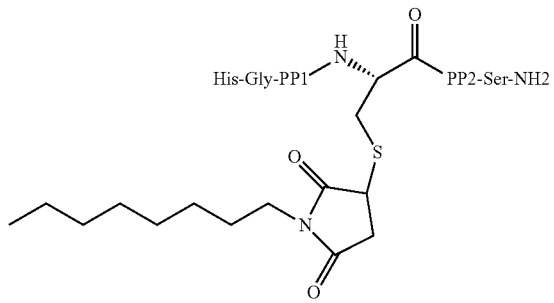

wherein PP1 is the polypeptide having the amino acid sequence shown as SEQ ID NO.:05 and PP2 is the polypeptide having the amino acid sequence shown as SEQ ID NO.:07

A polypeptide chain of compound 4 was dissolved with DMSO and prepared into a solution about 10 mg/mL. N-octane maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.9 mg of a pure product. A theoretical relative molecular mass was 4493.0. ESI-MS m/z: Calcd. $[M+3H]^{3+}$ 1498.7, $[M+4H]^{4+}$ 1124.2; Found $[M+3H]^{3+}$ 1498.9, $[M+4H]^{4+}$ 1124.3.

Embodiment 11

Solid-phase synthesis of compound 11:

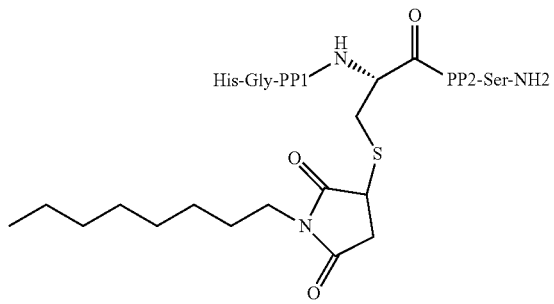

wherein PP1 is the polypeptide having the amino acid sequence shown as SEQ ID NO.:05 and PP2 is the polypeptide having the amino acid sequence shown as SEQ ID NO.:03

A polypeptide chain of compound 5 was dissolved with DMSO and prepared into a solution about 10 mg/mL. N-octane maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.3 mg of a pure product. A theoretical relative molecular mass was 4463.0. ESI-MS m/z: Calcd. $[M+3H]^{3+}$ 1488.7, $[M+4H]^{4+}$ 1116.7; Found $[M+3H]^{3+}$ 1488.0, $[M+4H]^{4+}$ 1116.0.

Embodiment 12 compound 12:

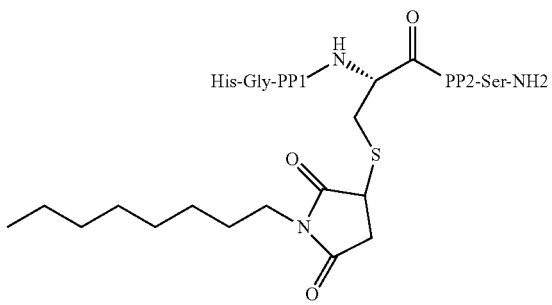

wherein PP1 is the polypeptide having the amino acid sequence shown as SEQ ID NO.:05 and PP2 is the polypeptide having the amino acid sequence shown as SEQ ID NO.:08

A polypeptide chain of compound 6 was dissolved with DMSO and prepared into a solution about 10 mg/mL. N-octane maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 29.4 mg of a pure product. A theoretical relative molecular mass was 4465.9. ESI-MS m/z: Calcd. $[M+3H]^{3+}$ 1489.6, $[M+4H]^{4+}$ 1117.5; Found $[M+3H]^{3+}$ 1489.6, $[M+4H]^{4+}$ 1117.7.

Embodiment 13

Solid-phase synthesis of compound 13:

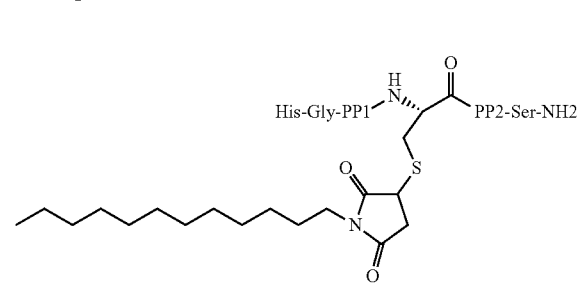

wherein PP1 is the polypeptide having the amino acid sequence shown as SEQ ID NO.:02 and PP2 is the polypeptide having the amino acid sequence shown as SEQ ID NO.:03

A polypeptide chain of compound 1 was dissolved with DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.7 mg of a pure product. A theoretical relative molecular mass was 4539.1. ESI-MS m/z: Calcd. [M+3H]$^{3+}$ 1514.0, [M+4H]$^{4+}$ 1135.8; Found [M+3H]$^{3+}$ 1514.5, [M+4H]$^{4+}$ 1135.5.

Embodiment 14

Solid-phase synthesis of compound 14:

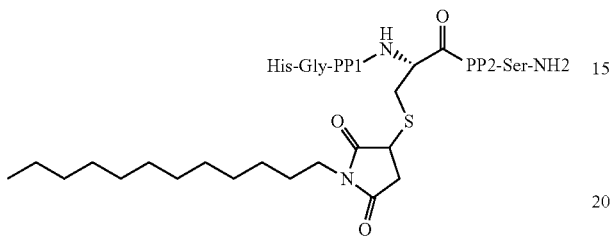

wherein PP1 is the polypeptide having the amino acid sequence shown as SEQ ID NO.:04 and PP2 is the polypeptide having the amino acid sequence shown as SEQ ID NO.:03

A polypeptide chain of compound 2 was dissolved with DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 27.1 mg of a pure product. A theoretical relative molecular mass was 4535.1. ESI-MS m/z: Calcd. [M+3H]$^{3+}$ 1512.7, [M+4H]$^{4+}$ 1134.8; Found [M+3H]$^{3+}$ 1512.5, [M+4H]$^{4+}$ 1134.2.

Embodiment 15

Solid-phase synthesis of compound 15:

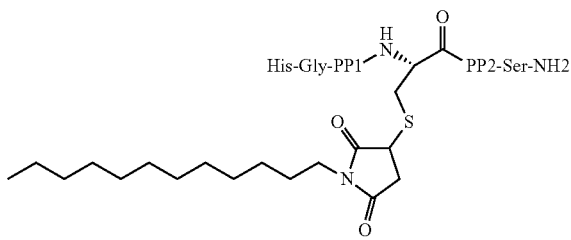

wherein PP1 is the polypeptide having the amino acid sequence shown as SEQ ID NO.:05 and PP2 is the polypeptide having the amino acid sequence shown as SEQ ID NO.:06

A polypeptide chain of compound 3 was dissolved by DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.5 mg of a pure product. A theoretical relative molecular mass was 4494.0. ESI-MS m/z: Calcd. [M+3H]$^{3+}$ 1499.0, [M+4H]$^{4+}$ 1124.5; Found [M+3H]$^{3+}$ 1499.0, [M+4H]$^{4+}$ 1124.0.

Embodiment 16

Solid-phase synthesis of compound 16:

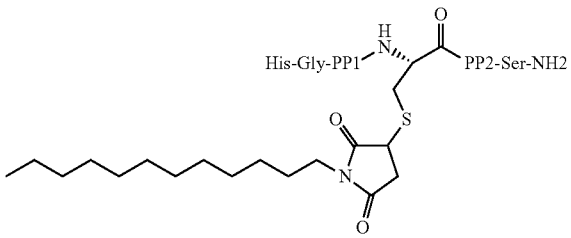

wherein PP1 is the polypeptide having the amino acid sequence shown as SEQ ID NO.:05 and PP2 is the polypeptide having the amino acid sequence shown as SEQ ID NO.:07

A polypeptide chain of compound 4 was dissolved with DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 28.1 mg of a pure product. A theoretical relative molecular mass was 4549.1. ESI-MS m/z: Calcd. [M+3H]$^{3+}$ 1517.4, [M+4H]$^{4+}$ 1138.3; Found [M+3H]$^{3+}$ 1517.2, [M+4H]$^{4+}$ 1138.8.

Embodiment 17

Solid-phase synthesis of compound 17:

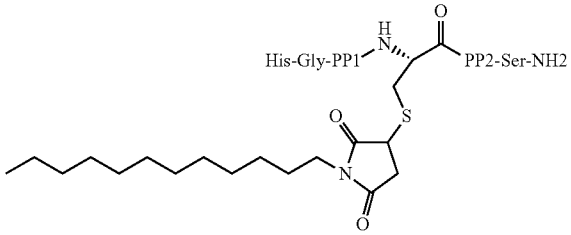

wherein PP1 is the polypeptide having the amino acid sequence shown as SEQ ID NO.:05 and PP2 is the polypeptide having the amino acid sequence shown as SEQ ID NO.:03

A polypeptide chain of compound 5 was dissolved with DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 27.8 mg of a pure product. A theoretical relative molecular mass was 4519.1. ESI-MS m/z: Calcd. [M+3H]$^{3+}$ 1507.4, [M+4H]$^{4+}$ 1130.8; Found [M+3H]$^{3+}$ 1507.0, [M+4H]$^{4+}$ 1130.2.

Embodiment 18

Solid-phase synthesis of compound 18:

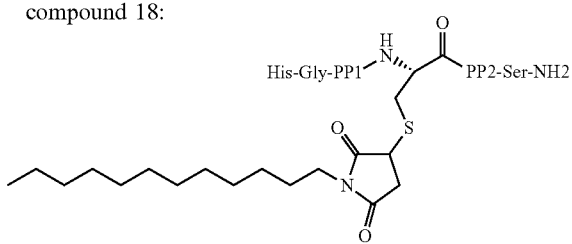

wherein PP1 is the polypeptide having the amino acid sequence shown as SEQ ID NO.:05 and PP2 is the polypeptide having the amino acid sequence shown as SEQ ID NO.:08

A polypeptide chain of compound 6 was dissolved with DMSO and prepared into a solution about 10 mg/mL. N-dodecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 29.1 mg of a pure product. A theoretical relative molecular mass was 4522.0. ESI-MS m/z: Calcd. $[M+3H]^{3+}$ 1508.3, $[M+4H]^{4+}$ 1131.5; Found $[M+3H]^{3+}$ 1508.6, $[M+4H]^{4+}$ 1131.4.

Embodiment 19

Solid-phase synthesis of compound 19:

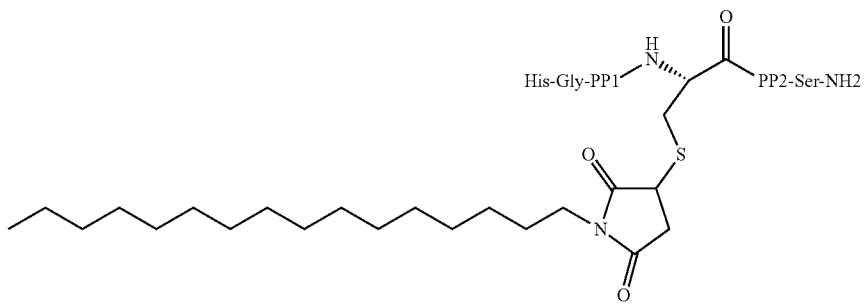

wherein PP1 is the polypeptide having the amino acid sequence shown as SEQ ID NO.:02 and PP2 is the polypeptide having the amino acid sequence shown as SEQ ID NO.:03

A polypeptide chain of compound 1 was dissolved by DMSO and prepared into a solution about 10 mg/mL. N-hexadecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 30.2 mg of a pure product. A theoretical relative molecular mass was 4595.2. ESI-MS m/z: Calcd. $[M+3H]^{3+}$ 1532.7, $[M+4H]^{4+}$ 1149.8; Found $[M+3H]^{3+}$ 1532.8, $[M+4H]^{4+}$ 1149.2.

Embodiment 20

Solid-phase synthesis of compound 20:

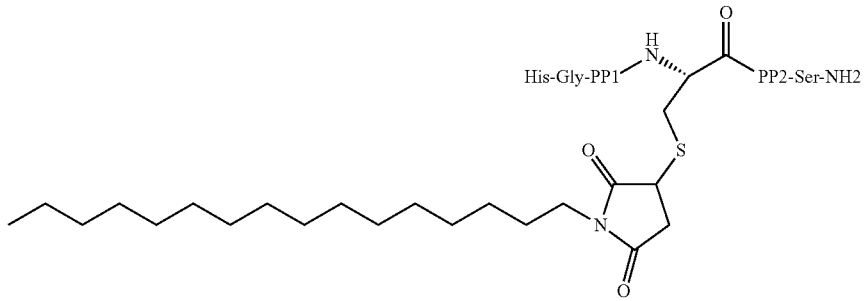

wherein PP1 is the polypeptide having the amino acid sequence shown as SEQ ID NO.:04 and PP2 is the polypeptide having the amino acid sequence shown as SEQ ID NO.:03

A polypeptide chain of compound 2 was dissolved by DMSO and prepared into a solution about 10 mg/mL. N-hexadecyl maleimide was also dissolved in DMSO. After mixing of the two solutions, 20 µl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 30.4 mg of a pure product. A theoretical relative molecular mass was 4591.2. ESI-MS m/z: Calcd. [M+3H]$^{3+}$ 1531.4, [M+4H]$^{4+}$ 1148.8; Found [M+3H]$^{3+}$ 1531.5, [M+4H]$^{4+}$ 1149.0.

Embodiment 21

Solid-phase synthesis of compound 21:

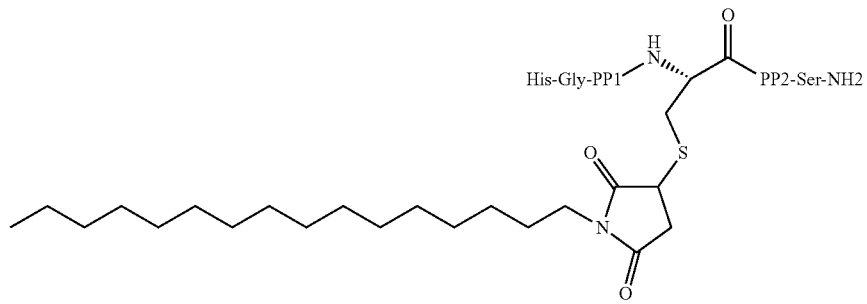

wherein PP1 is the polypeptide having the amino acid sequence shown as SEQ ID NO.:05 and PP2 is the polypeptide having the amino acid sequence shown as SEQ ID NO.:06

A polypeptide chain of compound 3 was dissolved with DMSO and prepared into a solution about 10 mg/mL. N-hexadecyl maleimide was also dissolved in DMSO. After mixing of the two solutions, 20 µl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 29.4 mg of a pure product. A theoretical relative molecular mass was 4550.1. ESI-MS m/z: Calcd. [M+3H]$^{3+}$ 1517.7, [M+4H]$^{4+}$ 1138.5; Found [M+3H]$^{3+}$ 1517.0, [M+4H]$^{4+}$ 1138.7.

Embodiment 22

Solid-phase synthesis of compound 22:

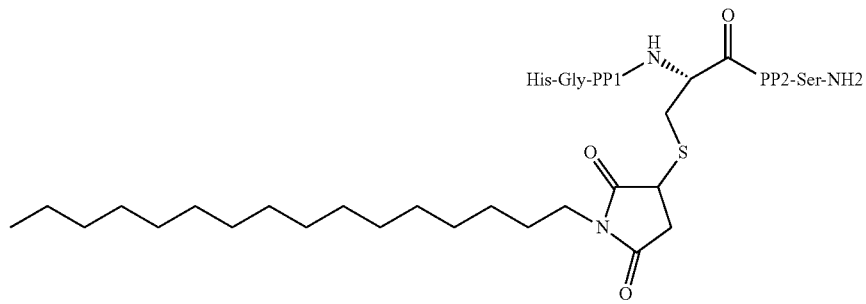

wherein PP1 is the polypeptide having the amino acid sequence shown as SEQ ID NO.:05 and PP2 is the polypeptide having the amino acid sequence shown as SEQ ID NO.:07

A polypeptide chain of compound 4 was dissolved with DMSO and prepared into a solution about 10 mg/mL. N-hexadecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 30.2 mg of a pure product. A theoretical relative molecular mass was 4605.2. ESI-MS m/z: Calcd. $[M+3H]^{3+}$ 1536.1, $[M+4H]^{4+}$ 1152.3; Found $[M+3H]^{3+}$ 1536.6, $[M+4H]^{4+}$ 1152.2.

Embodiment 23

Solid-phase synthesis of compound 23:

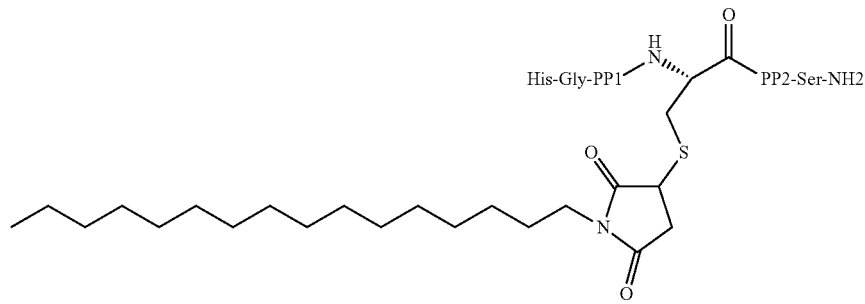

wherein PP1 is the polypeptide having the amino acid sequence shown as SEQ ID NO.:05 and PP2 is the polypeptide having the amino acid sequence shown as SEQ ID NO.:03

A polypeptide chain of compound 5 was dissolved with DMSO and prepared into a solution about 10 mg/mL. N-hexadecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 31.2 mg of a pure product. A theoretical relative molecular mass was 4575.2. ESI-MS m/z: Calcd. $[M+3H]^{3+}$ 1526.1, $[M+4H]^{4+}$ 1144.8; Found $[M+3H]^{3+}$ 1526.0, $[M+4H]^{4+}$ 1145.6.

Embodiment 24

Solid-phase synthesis of compound 24:

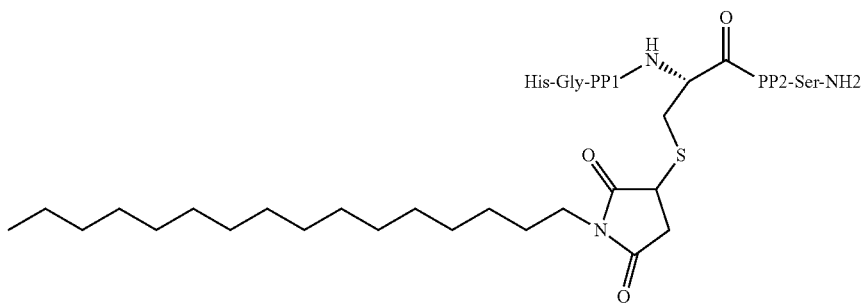

wherein PP1 is the polypeptide having the amino acid sequence shown as SEQ ID NO.:05 and PP2 is the polypeptide having the amino acid sequence shown as SEQ ID NO.:08

A polypeptide chain of compound 6 was dissolved with DMSO and prepared into a solution about 10 mg/mL. N-hexadecyl maleimide was also dissolved in DMSO. After mixing of the two solutions, 20 μl of DIEPA was added and stirred for reaction at room temperature. The reaction detection and purification methods were the same as those of Embodiment 7. A collected solution was subjected to reduced pressure concentration to remove acetonitrile. Freeze-drying was performed to obtain 30.8 mg of a pure product. A theoretical relative molecular mass was 4578.1. ESI-MS m/z: Calcd. $[M+3H]^{3+}$ 1527.0, $[M+4H]^{4+}$ 1145.5; Found $[M+3H]^{3+}$ 1527.2, $[M+4H]^{4+}$ 1145.9.

Embodiment 25

Solid-phase synthesis of compound 25:

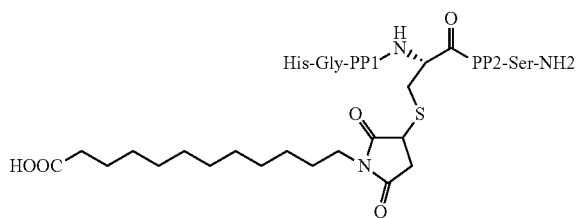

wherein PP1 is the polypeptide having the amino acid sequence shown as SEQ ID NO.:05 and PP2 is the polypeptide having the amino acid sequence shown as SEQ ID NO.:08

1. Synthesis of Peptide Chain 1.1 Swelling of Resin 50 mg of Fmoc-Rink amide-MBHA Resin (substitution degree: 0.4 mmol/g) was weighed, and was swelled with 7 mL of DCM for 30 min. DCM was removed through suction filtration. Then, the resin was swelled with 10 mL of NMP for 30 min, and was cleanly flushed respectively with 7 mL of NMP and 7 mL of DCM.

1.2 Removal of Fmoc Protecting Group

The swelled resin was put into a reactor. A 25% piperidine/NMP (V/V) solution containing 0.1 M HOBt was added into the resin to remove Fmoc. After the reaction was completed, the resin was cleanly washed with NMP. Resin with initially linked Fmoc protecting groups removed was obtained.

1.3 Synthesis of Fmoc-Ser(tBu)-Rink Amide-MBHA Resin

Fmoc-Ser(tBu)-OH (15.4 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin obtained in the previous step to react for 2 h. After the reaction was completed, reaction liquid was filtered away, and the resin was flushed with 7 mL of DCM and 7 mL of NMP 3 times.

1.4 Elongation of Peptide Chain

According to the sequence of the peptide chain, corresponding amino acids were sequentially linked by repeating the above deprotection and coupling steps. The corresponding amino acids were sequentially linked until the synthesis of the peptide chain was completed. The resin linked with a main chain peptide with a sequence of compound 1 was obtained.

1.6 Lysis of Polypeptide on Resin

The obtained resin linked with a main chain peptide with a sequence of compound 25 was put into a reaction bottle. 10 mL of a lysis agent Reagent K (TFA/thioanisole/water/phenol/EDT, 82.5:5:5:5:2.5, V/V) was respectively added. Firstly, shaking was performed at 0° C. for 30 min, and then, reaction was performed at a normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 77.1 mg of the crude product was finally obtained. The yield was 90.2%. The reaction was monitored by using HPLC. The chromatographic conditions were as follows: C18 column (150 mm×4.6 mm, 5 μm); mobile phase A: 0.1% TFA/water (V/V), and mobile phase B: 0.1% TFA/acetonitrile (V/V); mobile phase gradient: mobile phase B 35%-85%, 20 min; flow rate: 1 mL/min; column temperature: 40° C.; and detection wavelength: 214 nm. After the reaction was completed, purification was performed by preparative liquid chromatography. The chromatographic conditions were as follows: C18 column (320 mm×28 mm, 5 μm); mobile phase A: 0.1% TFA/water (V/V), and mobile phase B: 0.1% TFA/acetonitrile (V/V); mobile phase gradient: mobile phase B 40%-90%, 20 min; flow rate: 6 mL/min; and detection wavelength: 214 nm. A collected solution was freeze-dried to obtain 28.5 mg of a pure product. A theoretical relative molecular mass was 4256.6. ESI-MS m/z: Calcd. $[M+3H]^{3+}$ 1419.9, $[M+4H]^{4+}$ 1065.2; Found $[M+3H]^{3+}$ 1420.1, $[M+4H]^{4+}$ 1065.5.

2. Synthesis of 12-(2,5-dihydro-2,5-dioxo-1H-pyrrol-1-yl) dodecanoic acid 12-aminododecanoic acid (0.86 g, 4 mmol) and maleic anhydride (0.47 g, 4.8 mmol) were dissolved in glacial acetic acid. After ultrasonic dissolution, reflux reaction was performed at 120° C. for 6 h. After the result detected by using a thin-layer plate showed that the reaction was complete, reaction liquid was cooled to room temperature. Extraction (3×20 mL) was performed by ethyl acetate three times. Upper layer extraction liquid was merged. The extraction liquid was washed with a saturated salt solution 3 times, and was dried over the night by anhydrous $Na_2SO_4$. The extraction liquid was subjected to vacuum spin drying to obtain a crude product. The crude product was subjected to column chromatography (ethyl acetate/petroleum ether) separation to obtain 0.89 g of a faint yellow pure product. The yield was 80%, and mp was 91-92° C.

$^1$H-NMR (DMSO-$d_6$, 300 MHz): δ ppm: 12.45 (s, 1H, —COO<u>H</u>), 7.50 (s, 2H, —COC<u>H</u>=C<u>H</u>CO—), 3.88 (t, 2H, J=7.0 Hz, —NC<u>H$_2$</u>—), 2.68 (t, J=7.3 Hz, 2H, —C<u>H$_2$</u>COOH), 2.00-1.96 (m, 4H, —NCH$_2$C<u>H$_2$</u>(CH$_2$)$_7$C<u>H$_2$</u>), 1.73 (s, 14H, —NCH$_2$CH$_2$(C<u>H$_2$</u>)$_7$CH$_2$). ESI-MS m/z: 294.1 $[M+H]^+$.

3. Synthesis and Purification of Chemically Modified OXM Conjugate

The 12-(2,5-dihydro-2,5-dioxo-1H-pyrrol-1-yl) dodecanoic acid obtained in the previous step was dissolved with DMSO and prepared into a solution about 10 mg/mL. The obtained main chain peptide with the sequence of compound 1 was also dissolved in DMSO. After ultrasonic mixing of the two solutions, 20 μl of DIEPA was added and stirred for reaction at room temperature. Reaction conditions were monitored with LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 8.1 mg of a pure product. A theoretical relative molecular mass was 4551.7. ESI-MS m/z: Calcd. $[M+3H]^{3+}$ 1518.3, $[M+4H]^{4+}$ 1138.9; Found $[M+3H]^{3+}$ 1517.4, $[M+4H]^{4+}$ 1138.8.

Embodiment 26

Synthesis of compound 26:

plete, reaction liquid was cooled to room temperature. Extraction (3×20 mL) was performed with ethyl acetate three times. Upper layer extraction liquid was merged. The extraction liquid was washed with a saturated salt solution 3 times, and was dried over the night by anhydrous $Na_2SO_4$. The extraction liquid was subjected to vacuum spin drying to obtain a crude product. The crude product was subjected to column chromatography (ethyl acetate/petroleum ether) separation to obtain 1.02 g of a faint yellow pure product. The yield was 72%.

$^1$H-NMR (DMSO-$d_6$, 300 MHz): δ ppm: 12.45 (s, 1H, —COO$\underline{H}$), 7.50 (s, 2H, —COC$\underline{H}$=C$\underline{H}$CO—), 3.88 (t, 2H, J=7.0 Hz, —NC$\underline{H}_2$—), 2.68 (t, J=7.3 Hz, 2H, —C$\underline{H}_2$COOH), 2.00-1.96 (m, 4H, —NCH$_2$C$\underline{H}_2$(C$\underline{H}_2$)$_7$C$\underline{H}_2$), 1.76 (s, 22H, —NCH$_2$CH$_2$(C$\underline{H}_2$)$_{11}$CH$_2$). ESI-MS m/z: 352.4 $[M+H]^+$.

2. Synthesis and Purification of Chemically Modified OXM Conjugate

The 16-(2,5-dihydro-2,5-dioxo-1H-pyrrol-1-yl) hexadecanoic acid obtained in the previous step was dissolved with DMSO and prepared into a solution about 10 mg/mL. The obtained main chain peptide with the sequence of compound 1 was also dissolved in DMSO. After ultrasonic mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic

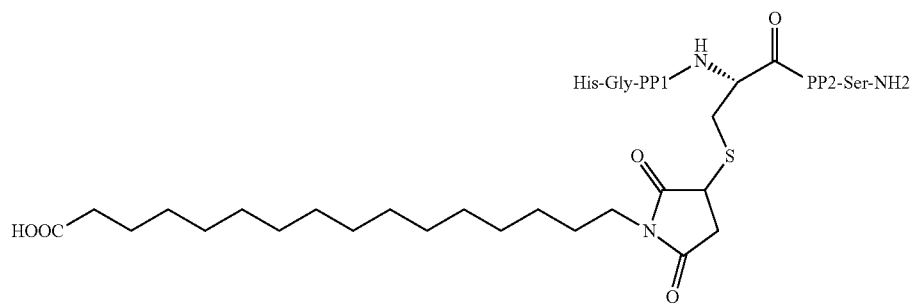

wherein PP1 is the polypeptide having the amino acid sequence shown as SEQ ID NO.:05 and PP2 is the polypeptide having the amino acid sequence shown as SEQ ID NO.:08

1. Synthesis of 16-(2,5-dihydro-2,5-dioxo-1H-pyrrol-1-yl)hexadecanoic acid 16-aminohexadecanoic acid (1.09 g, 4 mmol) and maleic anhydride (0.47 g, 4.8 mmol) were dissolved in glacial acetic acid. After ultrasonic dissolution, reflux reaction was performed at 120° C. for 6 h. After the result detected by using a thin-layer plate showed that the reaction was comconditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 8.7 mg of a pure product. A theoretical relative molecular mass was 4607.8. ESI-MS m/z: Calcd. $[M+3H]^{3+}$ 1536.9, $[M+4H]^{4+}$ 1152.9; Found $[M+3H]^{3+}$ 1537.6, $[M+4H]^{4+}$ 1153.5.

Embodiment 27 compound 27:

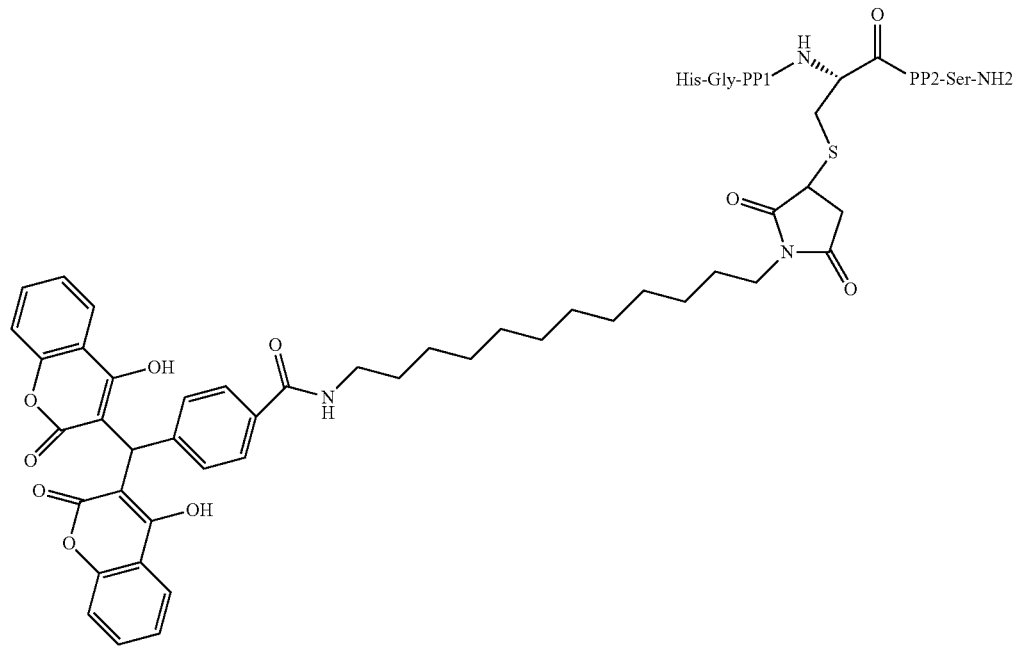

wherein PP1 is the polypeptide having the amino acid sequence shown as SEQ ID NO.:05 and PP2 is the polypeptide having the amino acid sequence shown as SEQ ID NO.:08

1. Synthesis of Chemically Modified Group

Synthesis of 3,3'-(4-carboxyphenylmethylene)-di-4-hydroxycoumarin

P-carboxybenzaldehyde (0.45 g, 3 mmol) was dissolved in 20 mL of absolute ethyl alcohol. Then, 4-hydroxycoumarin (0.98 g, 6 mmol) was added. After heating reflux for 12 h, reaction liquid was cooled to room temperature, and was then filtered. Filter cake was washed with 10 mL of ethyl alcohol 3 times. 1.12 g of a product was obtained, and the yield was 82.1%. ESI-MS m/z: 456.4 [M+H]$^+$.

Synthesis of (12-(2,5-dioxo-2,5-dihydro-1H-pyrrol-1-yl) dodecyl) tert-butyl carbamate N-Boc-dodecyl diamine (1.2 g, 4 mmol) and maleic anhydride (0.49 g, 4.8 mmol) were dissolved in glacial acetic acid. Heating reaction was performed at 120° C. for 6 h. After the result detected by using a thin-layer plate showed that the reaction was complete, reaction liquid was cooled to room temperature. Extraction (3×20 mL) was performed with ethyl acetate. Upper layer extraction liquid was merged. The extraction liquid was washed with a saturated salt solution 3 times, and was dried over the night by anhydrous Na$_2$SO$_4$. The extraction liquid was subjected to reduced pressure concentration to obtain a crude product. The obtained crude product was subjected to column chromatography purification to obtain 1.10 g of a faint yellow pure product. The yield was 72%. MS(ESI, m/z): 380.5 [M+H]$^+$.

Synthesis of 4-(bis(4-hydroxy-2-oxo-2H-chromen-3-yl)methyl)-N-(12-(2,5-dioxo-2,5-dihydro-1H-pyrrol-1-yl) dodecyl) benzamide (12-(2,5-dioxo-2,5-dihydro-1H-pyrrol-1-yl) dodecyl) tert-butyl carbamate (0.76 g, 2 mmol) was dissolved with HCl-saturated ethyl acetate. After stirring for 3 h, reduced pressure distillation was performed to remove a solvent. DCM redissolution was performed. 3,3'-(4-carboxyphenylmethylene)-di-4-hydroxycoumarin (0.91 g, 2 mmol), DIC (0.30 g, 2.4 mmol) and HOBt (0.32 g, 2.4 mmol) were added and stirred over the night at room temperature. After the result detected by using a thin-layer plate showed that the reaction was completed, reaction liquid was poured into water and was extracted with ethyl acetate three times. The extraction liquid was merged, and was respectively washed with a saturated K$_2$CO$_3$ solution, 1 M HCl and a saturated salt solution three times. The extraction liquid was added into anhydrous Na$_2$SO$_4$ and dried over the night. Reduced pressure concentration was performed to obtain a crude product. Column chromatography purification was performed to obtain 0.93 g of a pure product. The yield was 65%. ESI-MS m/z: 719.4 [M+H]$^+$.

2. Synthesis and Purification of Chemically Modified OXM Conjugate

The 4-(bis(4-hydroxy-2-oxo-2H-chromen-3-yl)methyl)-N-(12-(2,5-dioxo-2,5-dihydro-1H-pyrrol-1-yl) dodecyl) benzamide obtained in the previous step was dissolved with DMSO and prepared into a solution about 10 mg/mL. The main chain peptide with the sequence of compound 1 was also dissolved in DMSO. After ultrasonic mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 7.9 mg of a pure product. A theoretical relative molecular mass was 4974.9. ESI-MS m/z: Calcd. $[M+3H]^{3+}$ 1659.3, $[M+4H]^{4+}$ 1244.7; Found $[M+3H]^{3+}$ 1659.3, $[M+4H]^{4+}$ 1245.8.

Embodiment 28 compound 28:

lution could be complete. Reaction was performed at 80° C. for 4 h. Filtration was performed when the solution was still hot. Filter cake was washed with 10 mL of hot ethyl alcohol 3 times. 8.2 g of a product was obtained, the yield was 90.0%, and mp was 227° C.

$^1$H-NMR (CDCl$_3$, 300 MHz) δ ppm: 6.13 (s, H, —CH—), 7.43 (m, 8H, Ar—H), 7.68 (m, 2H, Ar—H), 8.18 (m, 2H, Ar—H). ESI-MS m/z: 456.0 $[M+H]^+$.

Synthesis of 3,3'-(4-aminophenylmethylene)-di-4-hydroxycoumarin 3,3'-(4-nitrophenylmethylene)-di-4-hydroxycoumarin (1.14 g, 0.0025 mol) was weighed, and was suspended with 30 mL of acetic acid. 0.3 g of 5% Pd/C was added and stirred. Gas extraction was performed by using a hydrogen tee-junction 3 times. Vaseline was coated on a bottle opening. Hydrogenation was performed at room temperature. Reaction was performed over the night. Suction filtration was performed. A part of solvent was removed from filter liquid through distillation. Recrystallization was performed by acetone. 0.8 g of a product was obtained, the yield was 75.1%, and mp was 220° C.

$^1$H-NMR (DMSO-d$_6$, 300 MHz) δ ppm: 6.27 (s, H, —CH—), 7.23 (m, 8H, Ar—H), 7.49 (m, 2H, Ar—H), 7.81 (m, 2H, Ar—H). ESI-MS m/z: 426.0 $[M+H]^+$.

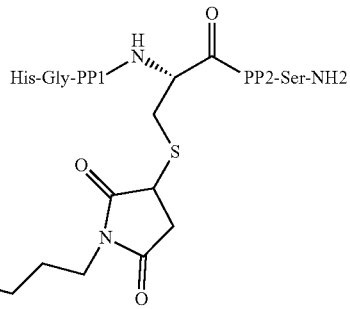

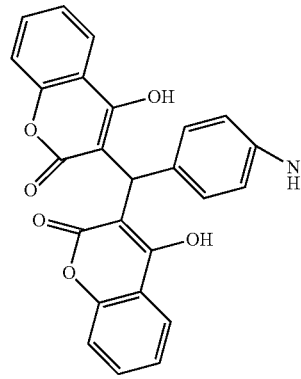

wherein PP1 is the polypeptide having the amino acid sequence shown as SEQ ID NO.:05 and PP2 is the polypeptide having the amino acid sequence shown as SEQ ID NO.:08

1. Synthesis of Chemically Modified Group

Synthesis of 3,3'-(4-nitrophenylmethylene)-di-4-hydroxycoumarin

P-nitrobenzaldehyde (3.02 g, 0.02 mol) was weighed and dissolved in 35 mL of absolute ethyl alcohol. Then, 4-hydroxycoumarin (6.6 g, 0.041 mol) was added. 15 mL of absolute ethyl alcohol was supplemented so that the disso- Synthesis of 3,3'-(4-(12-maleimidododecanamido)phenylmethylene)-di-4-hydroxycoumarin 12-maleimidododecanoic acid (294.1 mg, 1 mmol) was dissolved in tetrahydrofuran. DIC (17 μL, 1.1 mmol) and HOBt (148.5 mg, 1.1 mmol) were added and stirred at room temperature for 30 min. Then, the above solution was slowly dripped into a tetrahydrofuran solution of 3,3'-(4-aminophenylmethylene)-di-4-hydroxycoumarin and DIPEA (17.4 μL, 0.1 mmol) and stirred at room temperature over the night. After the result detected by using a thin-layer plate showed that the reaction was completed, reaction liquid was poured into water and was extracted with ethyl acetate three times. The extraction liquid was merged, and was respectively washed with a K₂CO₃ solution, 1 M HCl and a saturated salt solution three times. The extraction liquid was added into anhydrous Na₂SO₄ and dried over the night. Reduced pressure concentration was performed to obtain a crude product. Column chromatography purification was performed to obtain a pure product. The yield was 69%, and mp was 204-206° C.

¹H-NMR (DMSO-d₆, 300 MHz): δ ppm: 10.17 (s, 1H, —CONH—), 8.31 (d, J=7.8 Hz, 2H, Ar—H), 8.00 (t, J=7.2 Hz, 2H, Ar—H), 7.84 (d, J=8.0 Hz, 2H, Ar—H), 7.76-7.72 (m, 6H, Ar—H), 7.49 (s, 2H, —COCH=CHCO—), 6.70 (s, 1H, —CH—), 3.87 (t, J=7.0 Hz, 2H, —NCH₂—), 2.74 (t, J=7.2 Hz, 2H, —COCH₂—), 2.05-1.97 (m, 4H, —NCH₂CH₂(CH₂)₇CH₂—), 1.70 (s, 14H, —NCH₂CH₂(CH₂)₇CH₂—). ESI-MS m/z: 703.1 [M+H]⁺.

2. Synthesis and Purification of Chemically Modified OXM Conjugate

The 3,3'-(4-(12-maleimidododecanamido)phenylmethylene)-di-4-hydroxycoumarin obtained in the previous step was dissolved with DMSO and prepared into a solution about 10 mg/mL. The main chain peptide with the sequence of compound 1 was also dissolved in DMSO. After ultrasonic mixing of the two solutions, 20 μl of DIEPA was added and stirred for reaction at room temperature. Reaction conditions were monitored by using LC-MS monitoring. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 8.6 mg of a pure product. A theoretical relative molecular mass was 4960.9. ESI-MS m/z: Calcd. [M+3H]³⁺ 1654.6, [M+4H]⁴⁺ 1241.2; Found [M+3H]³⁺ 1654.2, [M+4H]⁴⁺ 1240.2.

Embodiment 29 compound 29:

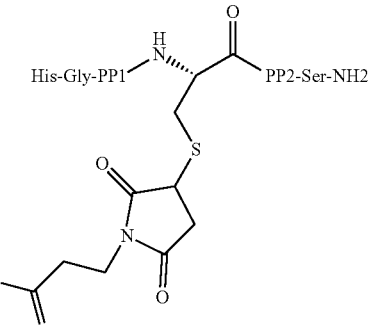

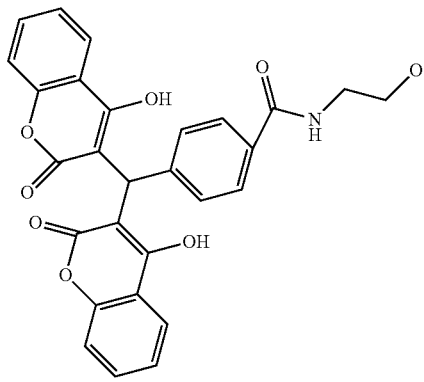

wherein PP1 is the polypeptide having the amino acid sequence shown as SEQ ID NO.:05 and PP2 is the polypeptide having the amino acid sequence shown as SEQ ID NO.:08

1. Synthesis of Chemically Modified Group

Synthesis of 3,3'-(4-carboxyphenylmethylene)-di-4-hydroxycoumarin

P-carboxybenzaldehyde (0.45 g, 3 mmol) was dissolved in 20 mL of absolute ethyl alcohol. Then, 4-hydroxycoumarin (0.98 g, 6 mmol) was added. After heating reflux for 12 h, reaction liquid was cooled to room temperature, and was then filtered. Filter cake was washed with 10 mL of ethyl alcohol 3 times. 1.12 g of a product was obtained, and the yield was 82.1%.

¹H-NMR (DMSO-d₆, 300 MHz): δ ppm: 8.37 (d, J=7.8 Hz, 2H, Ar—H), 8.29 (d, J=8.0 Hz, 2H, Ar—H), 8.06 (t, J=7.2 Hz, 2H, Ar—H), 7.84-7.74 (m, 6H, Ar—H), 6.86 (s, 1H, —CH—). ESI-MS m/z: 456.4 [M+H]

Synthesis of tert-butyl 2-(2-(2-aminoethoxy)ethoxy)ethylcarbamate 1,8-diamino-3,6-dioxaoctane (10.7 g, 72.3 mmol) was dissolved in 70 mL of DCM. Boc anhydride (2.2 g, 10.1 mmol) was dissolved in 50 mL of DCM. Under the condition of 0° C., Boc anhydride was slowly dripped into the 1,8-diamino-3,6-dioxaoctane solution. After the dripping was completed, and reaction liquid recovered to room temperature, the reaction was continuously performed for 4 h. After the reaction was completed, column chromatography was performed by basic aluminum oxide. Through separation and purification, 1.8 g of a colorless transparent oily substance could be obtained, and the yield was 72.0%.

¹H NMR (DMSO-d₆, 300 MHz): δ 4.96 (s, 1H, —NH—), 3.54 (s, 4H, —OCH₂—), 3.42 (dt, J=5.1, 5.1 Hz, 4H, —OCH₂CH₂O—), 3.10 (dt, J=5.1, 5.1 Hz, 2H, —CH₂NH(Boc)), 2.55 (s, 2H, —CH₂NH₂), 1.45 (s, 2H, —NH₂), 1.42 (s, 9H, -t-Bu). ESI-MS m/z: 249.0 [M+H]⁺.

Synthesis of tert-butyl (2-(2-(2-(3-(2,5-dioxo-2,5-dihydro-1H-pyrrol-1-yl)propionamido)ethoxy)ethoxy)ethyl carbamate 3-(2,5-dihydro-2,5-dioxo-1H-pyrrol-1-yl) propionic acid (523.mg, 3.1 mmol) and tert-butyl 2-(2-(2-aminoethoxy)ethoxy)ethylcarbamate (843 mg, 3.4 mmol) described in 2.2.1.2 were weighed and were dissolved in 15 mL of dichloromethane. After ice bath cooling, EDC-HCl (680 mg, 3.6 mmoL) and DMAP (75 mg, 0.6 mmoL) were added. A temperature of reaction liquid was slowly raised from 0° C. to room temperature. Reaction was performed for 6 h. Through column chromatography purification, 0.99 g of a white ointment type pure product was obtained, and the yield was 80.5%.

¹H NMR (DMSO-d₆, 300 MHz): δ 8.03 (s, 1H, —CH₂CONH—), 7.00 (s, 2H, —COCH=CHCO—), 6.76 (s, 1H, =OCONH—), 5.75 (t, J=7.2 Hz, 2H, —NCH₂CH₂—), 3.59 (t, J=4.4 Hz, 4H, —OCH₂CH₂NH—), 3.48 (s, 4H, —CH₂O CH₂ CH₂OCH₂—), 3.15 (t, 2H, J=5.6 Hz, —CH₂CONH CH₂—), 3.06 (t, 2H, J=5.8 Hz, —OCONHCH₂—), 2.33 (t, J=6.8 Hz, 2H, —CH₂CONH—), 1.36 (s, 9H, —CH₃). ESI-MS m/z: 399.5 [M+H]⁺.

Synthesis of 4-(bis(4-hydroxy-2-oxo-2H-benzopyran-3-yl)methyl)-N-(2-(2-(2-(3-(2,5-dioxo-2,5-dihydro-1H-pyrrol-1-yl)propionamido)ethoxy)ethoxy)ethyl)benzamide Tert-butyl (2-(2-(2-(3-(2,5-dioxo-2,5-dihydro-1H-pyrrol-1-yl)propionamido)ethoxy)ethoxy)ethyl) carbamate (159.8 mg, 0.4 mmol) was dissolved in 3 ml of acetonitrile. After the solution was cooled to room temperature, 1 mL of trifluoroacetic acid was added. After the reaction was complete, reduced pressure distillation was performed to remove a solvent, a faint yellow oily substance was obtained, and was redissolved in 3 mL of tetrahydrofuran. 3,3'-(4-carboxyphenylmethylene)-di-4-hydroxycoumarin (182.6 mg, 0.4 mmol) was dissolved in 5 mL of tetrahydrofuran, DIC (68 μL, 0.44 mmol) and HOBt (59.4 mg, 0.44 mmol) were added and stirred at room temperature for 30 min to activate carboxyl. The above solution was slowly dripped into a tetrahydrofuran solution of a product obtained after the above Boc removal and stirred at room temperature for overnight reaction. After the reaction was completed, reaction liquid was poured into ice water. Extraction was performed with 20 mL of dichloromethane three times. Extraction liquid was merged, and was respectively washed with a saturated K₂CO₃ solution, 1 M HCl and a saturated salt solution three times. The extraction liquid was added into anhydrous Na₂SO₄ and dried over the night. Then, reduced pressure concentration was performed to obtain a crude product. Column chromatography purification was performed to obtain 132.8 mg of a white paste type pure product. The yield was 45%.

¹H-NMR (DMSO-d₆, 300 MHz): δ ppm: 8.94 (s, 1H, —NHCO—Ar), 8.38 (s, 1H, —NHCOCH₂—), 8.37 (d, J=7.8 Hz, 2H, Ar—H), 8.29 (d, J=8.25 Hz, 2H, Ar—H), 8.06 (t, J=7.2 Hz, 2H, Ar—H), 7.84-7.74 (m, 6H, Ar—H), 6.98 (s, 2H, —COCH=CHCO—), 6.86 (s, 1H, —CH—). 5.75 (t, J=7.2 Hz, 2H, —NCH₂CH₂—), 3.59 (t, J=6.0 Hz, 4H, —OCH₂CH₂NH—), 3.35 (s, 4H, —OCH₂CH₂O—), 3.15 (t, 4H, J=6.0 Hz, —CONH CH₂—), 2.33 (t, J=7.2 Hz, 2H, —CH₂CONH—). ESI-MS m/z: 738.4 [M+H]⁺.

2. Synthesis and Purification of Chemically Modified OXM Conjugate

The 4-(bis(4-hydroxy-2-oxo-2H-benzopyran-3-yl)methyl)-N-(2-(2-(2-(3-(2,5-dioxo-2,5-dihydro-1H-pyrrol-1-yl)propionamido)ethoxy)ethoxy)ethyl)benzamide obtained in the previous step was dissolved with DMSO and prepared into a solution about 10 mg/mL. The main chain peptide with the sequence of COMPOUND1 was also dissolved in DMSO. After ultrasonic mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 m); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 8.3 mg of a pure product. A theoretical relative molecular mass was 4993.8. ESI-MS m/z: Calcd. [M+3H]³⁺ 1665.6, [M+4H]⁴⁺ 1249.5; Found [M+3H]³⁺ 1665.8, [M+4H]⁴⁺ 1249.1.

Embodiment 30

Solid-phase synthesis of compound 30:

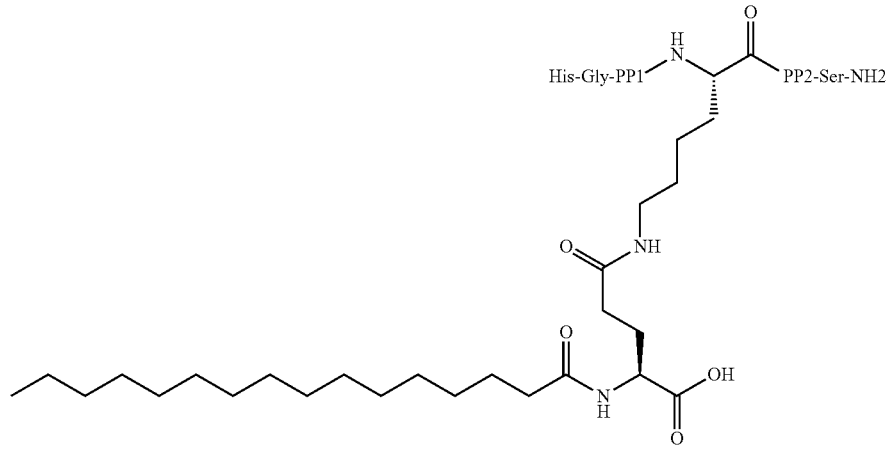

wherein PP1 is the polypeptide having the amino acid sequence shown as SEQ ID NO.:02 and PP2 is the polypeptide having the amino acid sequence shown as SEQ ID NO.:03

1. Synthesis of Polypeptide Main Chain

1.1 Swelling of Resin 50 mg of Fmoc-Rink amide-MBHA Resin (substitution degree: 0.4 mmol/g) was weighed, and was swelled with 7 mL of DCM for 30 min. DCM was removed through suction filtration. Then, the resin was swelled with 10 mL of NMP for 30 min, and was cleanly flushed respectively with 7 mL of NMP and 7 mL of DCM.

1.2 Removal of Fmoc Protecting Group

The swelled resin was put into a reactor. A 25% piperidine/NMP (V/V) solution containing 0.1 M HOBt was added into the resin to remove Fmoc. After the reaction was completed, the resin was cleanly washed with NMP. Resin with initially linked Fmoc protecting groups removed was obtained.

1.3 Synthesis of Fmoc-Ser(tBu)-Rink Amide-MBHA Resin

Fmoc-Ser(tBu)-OH (15.4 mg, 0.04 mmol), HBTU (15.1 mg, 0.04 mmol), HOBt (5.4 mg, 0.04 mmol) and DIPEA (13.9 µL, 0.08 mmol) were dissolved in 10 mL of NMP. Then, this solution was added into the resin obtained in the previous step to react for 2 h. After the reaction was completed, reaction liquid was filtered away, and the resin was flushed with 7 mL of DCM and 7 mL of NMP 3 times.

1.4 Elongation of Peptide Chain

According to the sequence of the peptide chain, corresponding amino acids were sequentially linked by repeating the above deprotection and coupling steps. The corresponding amino acids were sequentially linked until the synthesis of the peptide chain was completed. The resin linked with the main chain amino acid with the sequence of compound 1 was obtained.

2. Linking of Formula I to Peptide Resin

The resin linked with the compound 1 main chain was put into a reactor. A 2% hydrazine hydrate solution was added to remove a side chain protecting group Dde of Lys at position 16. After the reaction was completed, the resin was cleanly washed with NMP. Fmoc-Glu-OtBu (17.0 mg, 0.04 mmol), HBTU (15.1 mg, 0.04 mmol), HOBt (5.4 mg, 0.04 mmol) and DIPEA (13.9 µL, 0.08 mmol) were dissolved in 10 mL of NMP. Then, this solution was added into the resin to react for 2 h. After the reaction was completed, reaction liquid was filtered away. The resin was washed with 7 mL of DCM and 7 mL of NMP 3 times. A 25% piperidine/NMP (V/V) solution containing 0.1 M HOBt was added into the resin to remove Fmoc. After the reaction was completed, the resin was cleanly washed with NMP. Hexadecanoic acid (10.3 mg, 0.04 mmol), HBTU (15.1 mg, 0.04 mmol), HOBt (5.4 mg, 0.04 mmol) and DIPEA (13.9 L, 0.08 mmol) were dissolved in 10 mL of NMP. Then, this solution was added into the resin to react for 2 h. After the reaction was completed, reaction liquid was filtered away. The resin was washed with 7 mL of DCM and 7 mL of NMP 3 times. Resin linked with a complete structure of compound 1 was obtained.

3. Lysis of Polypeptide on Resin

The obtained resin linked with the complete structure of compound 1 was put into a reaction bottle. 10 mL of a lysis agent Reagent K (TFA/thioanisole/water/phenol/EDT, 82.5:5:5:5:2.5, V/V) was added. Firstly, shaking was performed at 0° C. for 30 min, and then, reaction was performed at normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 86.3 mg of the crude product was finally obtained. The yield was 92.4%. The reaction was monitored by using HPLC. The chromatographic conditions were as follows: C18 column (150 mm×4.6 mm, 5 μm); mobile phase A: 0.1% TFA/water (V/V), and mobile phase B: 0.1% TFA/acetonitrile (V/V); mobile phase gradient: mobile phase B 35%-85%, 20 min; flow rate: 1 mL/min; column temperature: 40° C.; and detection wavelength: 214 nm. After the reaction was completed, purification was performed by preparative liquid chromatography. The chromatographic conditions were as follows: C18 column (320 mm×28 mm, 5 μm); mobile phase A: 0.1% TFA/water (V/V), and mobile phase B: 0.1% TFA/acetonitrile (V/V); mobile phase gradient: mobile phase B 40%-90%, 20 min; flow rate: δ mL/min; and detection wavelength: 214 nm. A collected solution was freeze-dried to obtain 31.2 mg of a pure product. A theoretical relative molecular mass was 4666.6. ESI-MS m/z: Calcd. $[M+3H]^{3+}$ 1556.5, $[M+4H]^{4+}$ 1167.7; Found $[M+3H]^{3+}$ 1556.9, $[M+4H]^{4+}$ 1166.9.

Embodiment 31 compound 31:

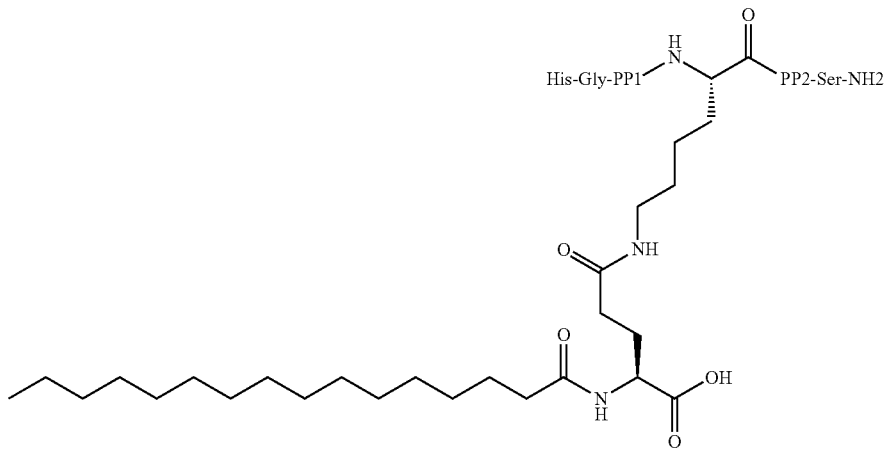

wherein PP1 is the polypeptide having the amino acid sequence shown as SEQ ID NO.:04 and PP2 is the polypeptide having the amino acid sequence shown as SEQ ID NO.:03

A synthesis method was the same as that of Embodiment 30. The collected solution was freeze-dried to obtain 29.9 mg of a pure product. A theoretical relative molecular mass was 4662.3. ESI-MS m/z: Calcd. $[M+3H]^{3+}$ 1555.1, $[M+4H]^{4+}$ 1166.6; Found $[M+3H]^{3+}$ 1555.7, $[M+4H]^{4+}$ 1166.1.

Embodiment 32 compound 32:

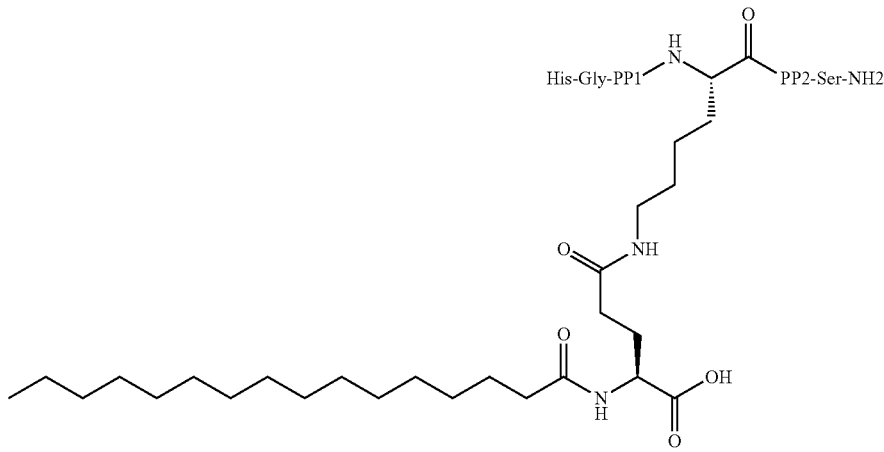

wherein PP1 is the polypeptide having the amino acid sequence shown as SEQ ID NO.:05 and PP2 is the polypeptide having the amino acid sequence shown as SEQ ID NO.:06

A synthesis method was the same as that of Embodiment 30. The collected solution was freeze-dried to obtain 30.4 mg of a pure product. A theoretical relative molecular mass was 4621.2. ESI-MS m/z: Calcd. [M+3H]$^{3+}$ 1541.4, [M+4H]$^{4+}$ 1156.3; Found [M+3H]$^{3+}$ 1541.9, [M+4H]$^{4+}$ 1156.7.

Embodiment 33 compound 33:

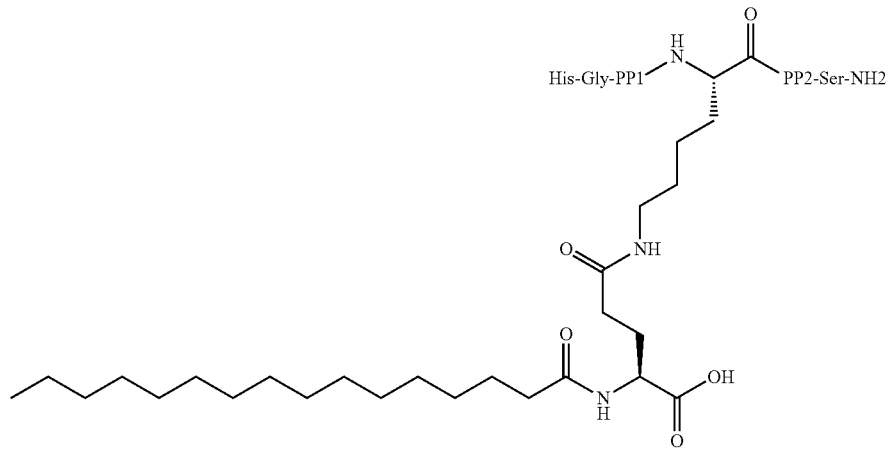

wherein PP1 is the polypeptide having the amino acid sequence shown as SEQ ID NO.:05 and PP2 is the polypeptide having the amino acid sequence shown as SEQ ID NO.:07

A synthesis method was the same as that of Embodiment 30. The collected solution was freeze-dried to obtain 32.2 mg of a pure product. A theoretical relative molecular mass was 4676.3. ESI-MS m/z: Calcd. [M+3H]$^{3+}$ 1559.8, [M+4H]$^{4+}$ 1170.1; Found [M+3H]$^{3+}$ 1560.4, [M+4H]$^{4+}$ 1170.5.

Embodiment 34 compound 34:

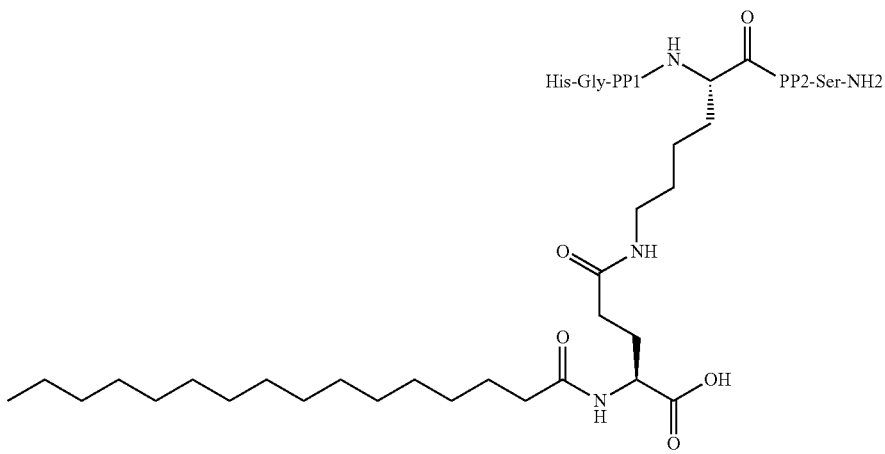

wherein PP1 is the polypeptide having the amino acid sequence shown as SEQ ID NO.:05 and PP2 is the polypeptide having the amino acid sequence shown as SEQ ID NO.:03

A synthesis method was the same as that of Embodiment 30. The collected solution was freeze-dried to obtain 30.7 mg of a pure product. A theoretical relative molecular mass was 4646.3. ESI-MS m/z: Calcd. $[M+3H]^{3+}$ 1549.8, $[M+4H]^{4+}$ 1162.6; Found $[M+3H]^{3+}$ 1550.4, $[M+4H]^{4+}$ 162.

Embodiment 35 compound 35:

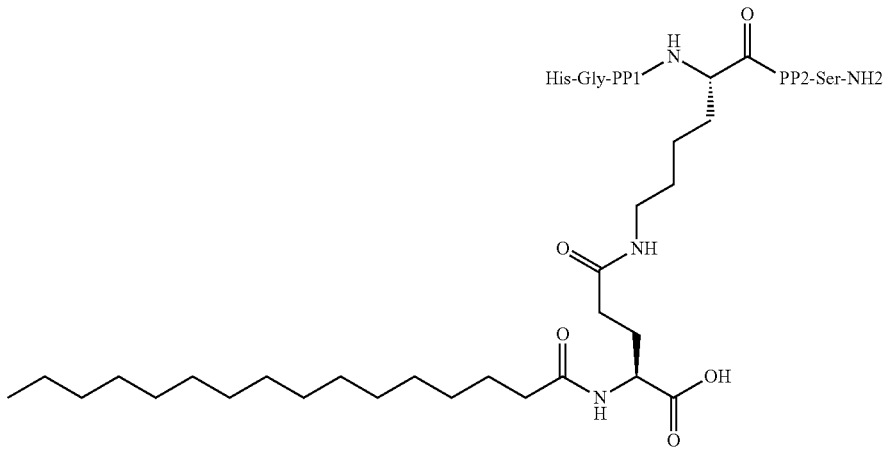

wherein PP1 is the polypeptide having the amino acid sequence shown as SEQ ID NO.:05 and PP2 is the polypeptide having the amino acid sequence shown as SEQ ID NO.:08

A synthesis method was the same as that of Embodiment 30. The collected solution was freeze-dried to obtain 29.4 mg of a pure product. A theoretical relative molecular mass was 4649.2 ESI-MS m/z: Calcd. $[M+3H]^{3+}$ 1550.7, $[M+4H]^{4+}$ 1163.3; Found $[M+3H]^{3+}$ 1550.8, $[M+4H]^{4+}$ 1163.7.

Embodiment 36

Solid-phase synthesis of compound 36:

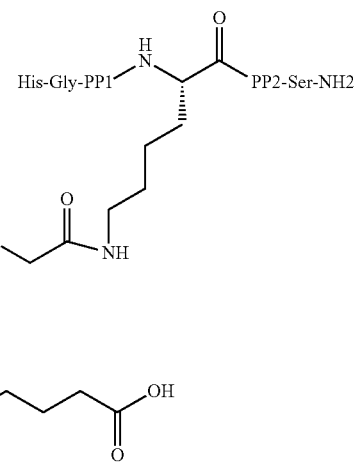

wherein PP1 is the polypeptide having the amino acid sequence shown as SEQ ID NO.:02 and PP2 is the polypeptide having the amino acid sequence shown as SEQ ID NO.:03

1. Synthesis of Formula I 100 mg 2-CTC resin (substitution degree: 0.8 mmol/g) was weighed, swelled with DCM for 30 min, then swelled with 10 mL of NMP for 30 min, and cleanly flushed respectively with 7 mL of NMP and 7 mL of DCM. Fmoc-AEEA (61.6 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into the resin to react for 2 h. After the reaction was completed, reaction liquid was filtered away. 10 mL of solution containing DCM, methanol and DIEA according to a ratio of 5:4:1 was added into resin for blocking reaction for 1 h. Reaction liquid was filtered way. The resin was washed with 7 mL of DCM and 7 mL of NMP 3 times.

A 25% piperidine/NMP (V/V) solution containing 0.1 M HOBt was added into the resin to remove Fmoc. After the reaction was completed, the resin was cleanly washed with NMP. Fmoc-AEEA was coupled again by the same method. After reaction was completed, the resin was washed with 7 mL of DCM and 7 mL of NMP 3 times. A 25% piperidine/NMP (V/V) solution containing 0.1 M HOBt was added into the resin to remove Fmoc. After the reaction was completed, the resin was cleanly washed with NMP. Fmoc-Glu-OtBu (68.0 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into the resin to react for 2 h. After the reaction was completed, reaction liquid was filtered away. The resin was washed with 7 mL of DCM and 7 mL of NMP 3 times. A 25% piperidine/NMP (V/V) solution containing 0.1 M HOBt was added into the resin to remove Fmoc. After the reaction was completed, the resin was cleanly washed with NMP. Octadecanedioic acid mono-tert-butyl ester (59.2 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into resin to react for 2 h. After the reaction was completed, reaction liquid was filtered away. The resin was washed with 7 mL of DCM and 7 mL of NMP 3 times.

The above obtained resin linked with Formula I was put into a reaction bottle. 10 mL of a lysis agent 20% trifluoroethanol/DCM was added. Shaking was performed for 30 min at normal temperature. After the reaction was completed, suction filtration was performed. A solvent was dried through distillation to obtain 42.4 mg of a crude product of Formula I. A theoretical relative molecular mass was 846.1. ESI-MS m/z: 845.4[M−H$^+$].

2. Synthesis of Polypeptide Main Chain 2.1 Swelling of Resin 50 mg of Fmoc-Rink amide-MBHA Resin (substitution degree: 0.4 mmol/g) was weighed, and was swelled with 7 mL of DCM for 30 min. DCM was removed through suction filtration. Then, the resin was swelled with 10 mL of NMP for 30 min, and was finally and cleanly flushed respectively with 7 mL of NMP and 7 mL of DCM.

2.2 Removal of Fmoc Protecting Group

The swelled resin was put into a reactor. A 25% piperidine/NMP (V/V) solution containing 0.1 M HOBt was added into the resin to remove Fmoc. After the reaction was completed, the resin was cleanly washed with NMP. Resin with initially linked Fmoc protecting groups removed was obtained.

2.3 Synthesis of Fmoc-Ser(tBu)-Rink Amide-MBHA Resin

Fmoc-Ser(tBu)-OH (15.4 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin obtained in the previous step to react for 2 h. After the reaction was completed, reaction liquid was filtered away, and the resin was washed with 7 mL of DCM and 7 mL of NMP 3 times.

2.4 Elongation of Peptide Chain

According to the sequence of the peptide chain, corresponding amino acids were sequentially linked by repeating the above deprotection and coupling steps. The corresponding amino acids were sequentially linked until the synthesis of the peptide chain was completed. The resin linked with the main chain peptide sequence was obtained.

3. Conjugation of Formula I and Polypeptide Main Chain

A 2% hydrazine hydrate solution was added into the resin linked with the main chain peptide sequence to remove a side chain protecting group Dde of Lys at position 16. After the reaction was completed, the resin was cleanly washed with NMP. Formula I (33.8 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin to react for 2 h. After the reaction was completed, reaction liquid was filtered away. The resin was washed with 7 mL of DCM and 7 mL of NMP 3 times. The peptide resin linked with compound 1 was obtained.

4. Lysis of Polypeptide on Resin

The above resin linked with compound 1 was put into a reaction bottle. 10 mL of a lysis agent Reagent K (TFA/thioanisole/water/phenol/EDT, 82.5:5:5:5:2.5, V/V) was respectively added. Firstly, shaking was performed at 0° C. for 30 min, and then, reaction was performed at normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 92.5 mg of the crude product was finally obtained. The yield was 92.1%. The reaction was monitored by using HPLC. The chromatographic conditions were as follows: C18 column (150 mm×4.6 mm, 5 μm); mobile phase A: 0.1% TFA/water (V/V), and mobile phase B: 0.1% TFA/acetonitrile (V/V); mobile phase gradient: mobile phase B 35%-85%, 20 min; flow rate: 1 mL/min; column temperature: 40° C.; and detection wavelength: 214 nm. After the reaction was completed, purification was performed by preparative liquid chromatography. The chromatographic conditions were as follows: C18 column (320 mm×28 mm, 5 μm); mobile phase A: 0.1% TFA/water (V/V), and mobile phase B: 0.1% TFA/acetonitrile (V/V); mobile phase gradient: mobile phase B 40%-90%, 20 min; flow rate: δ mL/min; and detection wavelength: 214 nm. A collected solution was freeze-dried to obtain 24.1 mg of a pure product. A theoretical relative molecular mass was 5014.6. ESI-MS m/z: Calcd. [M+3H]$^{3+}$ 1672.5, [M+4H]$^{4+}$ 1254.7; Found [M+3H]$^{3+}$ 1672.9, [M+4H]$^{4+}$ 1254.1.

Embodiment 37

Solid-phase synthesis of compound 37:

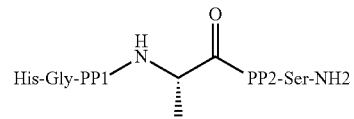
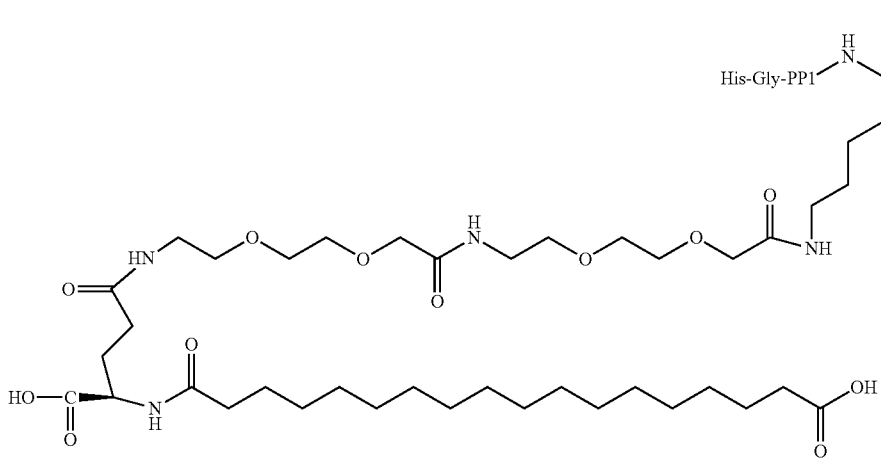

wherein PP1 is the polypeptide having the amino acid sequence shown as SEQ ID NO.:04 and PP2 is the polypeptide having the amino acid sequence shown as SEQ ID NO.:03

A synthesis method was the same as that of Embodiment 36. The collected solution was freeze-dried to obtain 26.4 mg of a pure product. A theoretical relative molecular mass was 5010.6. ESI-MS m/z: Calcd. [M+3H]$^{3+}$ 1671.2, [M+4H]$^{4+}$ 1253.7; Found [M+3H]$^{3+}$ 1671.8, [M+4H]$^{4+}$ 1253.1.

Embodiment 38 compound 38:

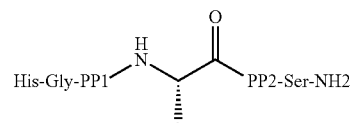
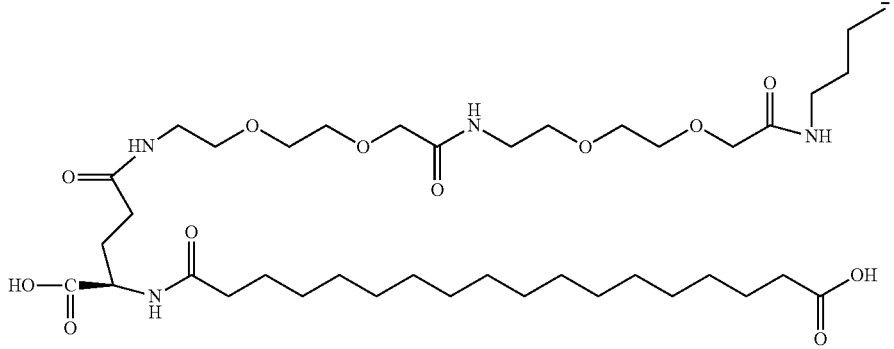

wherein PP1 is the polypeptide having the amino acid sequence shown as SEQ ID NO.:05 and PP2 is the polypeptide having the amino acid sequence shown as SEQ ID NO.:06

A synthesis method was the same as that of Embodiment 36. The collected solution was freeze-dried to obtain 24.2 mg of a pure product. A theoretical relative molecular mass was 4969.5. ESI-MS m/z: Calcd. $[M+3H]^{3+}$ 1657.5, $[M+4H]^{4+}$ 1243.4; Found $[M+3H]^{3+}$ 1657.3, $[M+4H]^{4+}$ 1243.7.

Embodiment 39 compound 39:

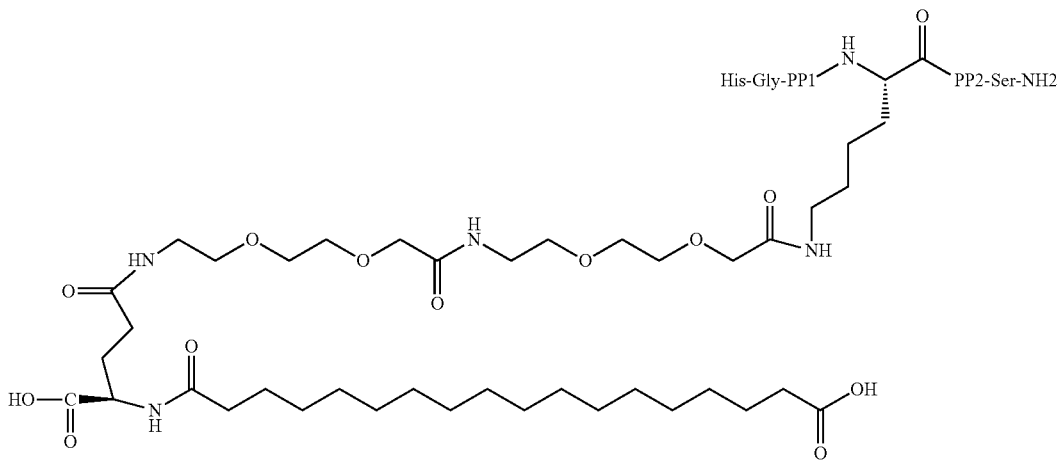

wherein PP1 is the polypeptide having the amino acid sequence shown as SEQ ID NO.:05 and PP2 is the polypeptide having the amino acid sequence shown as SEQ ID NO.:07

A synthesis method was the same as that of Embodiment 36. The collected solution was freeze-dried to obtain 22.2 mg of a pure product. A theoretical relative molecular mass was 5024.6. ESI-MS m/z: Calcd. $[M+3H]^{3+}$ 1675.9, $[M+4H]^{4+}$ 1257.2; Found $[M+3H]^{3+}$ 1675.7, $[M+4H]^{4+}$ 1257.4.

Embodiment 40 compound 40:

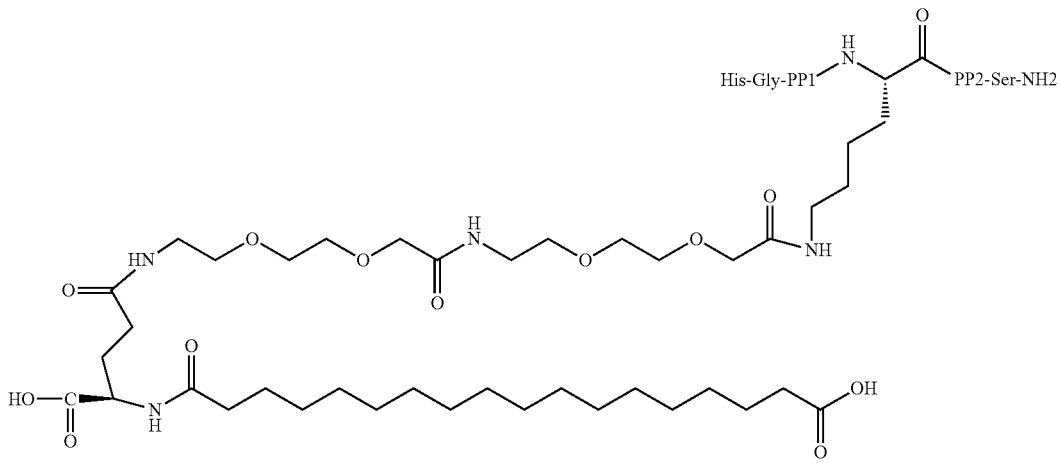

wherein PP1 is the polypeptide having the amino acid sequence shown as SEQ ID NO.:05 and PP2 is the polypeptide having the amino acid sequence shown as SEQ ID NO.:03

A synthesis method was the same as that of Embodiment 36. The collected solution was freeze-dried to obtain 22.4 mg of a pure product. A theoretical relative molecular mass was 4994.7. ESI-MS m/z: Calcd. $[M+3H]^{3+}$ 1665.9, $[M+4H]^{4+}$ 1249.7; Found $[M+3H]^{3+}$ 1665.4, $[M+4H]^{4+}$ 1249.5.

Embodiment 41 compound 41:

wherein PP1 is the polypeptide having the amino acid sequence shown as SEQ ID NO.:05 and PP2 is the polypeptide having the amino acid sequence shown as SEQ ID NO.:03

1. Synthesis of Polypeptide Main Chain 1.1 Swelling of Resin 50 mg of Fmoc-Rink amide-MBHA Resin (substitution degree: 0.4 mmol/g) was weighed, and was swelled with 7 mL of DCM for 30 min. DCM was removed through suction filtration. Then, the resin was swelled with 10 mL of NMP

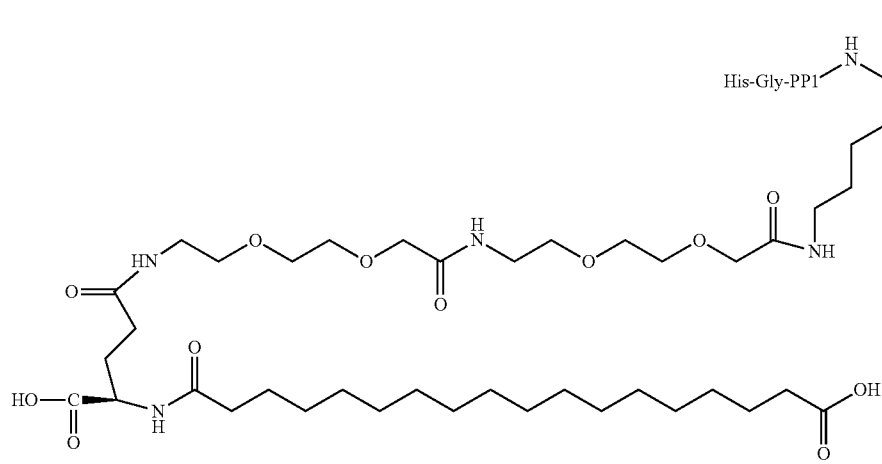

wherein PP1 is the polypeptide having the amino acid sequence shown as SEQ ID NO.:05 and PP2 is the polypeptide having the amino acid sequence shown as SEQ ID NO.:08

A synthesis method was the same as that of Embodiment 36. The collected solution was freeze-dried to obtain 21.8 mg of a pure product. A theoretical relative molecular mass was 4997.6. ESI-MS m/z: Calcd. $[M+3H]^{3+}$ 1666.9, $[M+4H]^{4+}$ 1250.4; Found $[M+3H]^{3+}$ 1666.8, $[M+4H]^{4+}$ 1249.7.

Embodiment 42 Solid-Phase Synthesis of compound 42:

for 30 min, and was finally and cleanly flushed respectively with 7 mL of NMP and 7 mL of DCM.

1.2 Removal of Fmoc Protecting Group

The swelled resin was put into a reactor. A 25% piperidine/NMP (V/V) solution containing 0.1 M HOBt was added into the resin to remove Fmoc. After the reaction was completed, the resin was cleanly washed with NMP. Resin with initially linked Fmoc protecting groups removed was obtained.

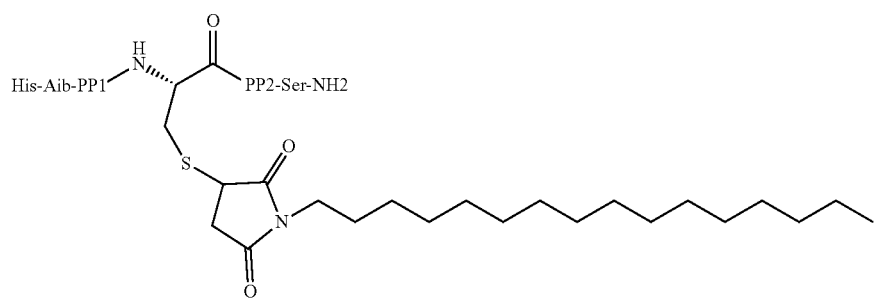

1.3 Synthesis of Fmoc-Ser(tBu)-Rink Amide-MBHA Resin

Fmoc-Ser(tBu)-OH (15.4 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin obtained in the previous step to react for 2 h. After the reaction was completed, reaction liquid was filtered away, and the resin was flushed with 7 mL of DCM and 7 mL of NMP 3 times.

1.4 Elongation of Peptide Chain

According to the sequence of the peptide chain, corresponding amino acids were sequentially linked by repeating the above deprotection and coupling steps. The corresponding amino acids were sequentially linked until the synthesis of the peptide chain was completed. The resin linked with the main chain peptide sequence was obtained.

1.5 Lysis of Polypeptide on Resin

The obtained resin linked with the main chain peptide sequence was put into a reaction bottle. 10 mL of a lysis agent Reagent K (TFA/thioanisole/water/phenol/EDT, 82.5:5:5:5:2.5, V/V) was added. Firstly, shaking was performed at 0° C. for 30 min, and then, reaction was performed at normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 82.4 mg of the crude product was finally obtained. The yield was 96.3%. A theoretical relative molecular mass was 4280.8. ESI-MS m/z: Calcd. [M+3H]$^{3+}$ 1427.9, [M+4H]$^{4+}$ 1071.2; Found. [M+3H]$^{3+}$ 1430.2, [M+4H]$^{4+}$ 1071.5.

2. Conjugation of Polypeptide Chain and Side Chain

The polypeptide chain was dissolved with DMSO and prepared into a solution about 10 mg/mL. N-hexadecyl maleimide was also dissolved in DMSO. After mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 m); mobile phase A: 0.1% TFA/water (V/V), and mobile phase B: 0.1% TFA/acetonitrile (V/V); mobile phase gradient: mobile phase B 40%-80%, 30 min; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 29.7 mg of a pure product. A theoretical relative molecular mass was 4603.3. ESI-MS m/z: Calcd. [M+3H]$^{3+}$ 1535.4, [M+4H]$^{4+}$ 1151.8; Found [M+3H]$^{3+}$ 1535.8, [M+4H]$^{4+}$ 1151.2.

Embodiment 43 Solid-Phase Synthesis of compound 43:

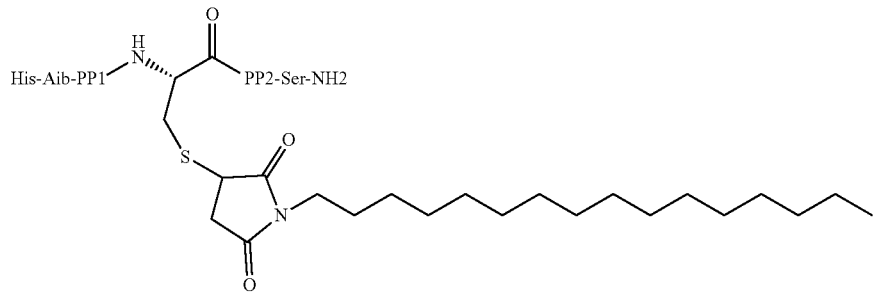

wherein PP1 is the polypeptide having the amino acid sequence shown as SEQ ID NO.:05 and PP2 is the polypeptide having the amino acid sequence shown as SEQ ID NO.:08

A synthesis method was the same as that of Embodiment 42. The collected solution was freeze-dried to obtain 27.4 mg of a pure product. A theoretical relative molecular mass was 4606.2. ESI-MS m/z: Calcd. [M+3H]$^{3+}$ 1536.4, [M+4H]$^{4+}$ 1152.6; Found. [M+3H]$^{3+}$ 1536.0, [M+4H]$^{4+}$ 1152.5.

Embodiment 44 Solid-Phase Synthesis of Compound 44

1. Synthesis of Polypeptide Main Chain

A synthesis method of the polypeptide main chain was the same as that of Embodiment 42.

2. Synthesis of Chemically Modified Group

Synthesis of 3,3'-(4-nitrophenylmethylene)-di-4-hydroxycoumarin

P-nitrobenzaldehyde (3.02 g, 0.02 mol) was dissolved in 35 mL of absolute ethyl alcohol. 4-hydroxycoumarin (6.6 g, 0.041 mol) was added. 15 mL of absolute ethyl alcohol was supplemented so that the dissolution could be complete.

Reaction was performed at 80° C. for 4 h. Filtration was performed when the solution was still hot. Filter cake was washed with 10 mL of hot ethyl alcohol 3 times. 8.4 g of a product was obtained, the yield was 92.1%, and mp was 227° C.

Synthesis of 3,3'-(4-aminophenylmethylene)-di-4-hydroxycoumarin 3,3'-(4-nitrophenylmethylene)-di-4-hydroxycoumarin (1.14 g, 0.0025 mol) was weighed, and was suspended by 30 mL of acetic acid. 0.3 g of 5% Pd/C was added and stirred. Gas extraction was performed 3 times by using a hydrogen tee-junction. Vaseline was coated on a bottle opening. Hydrogenation was performed at room temperature. Reaction was performed over the night. Suction filtration was performed. A part of solvent was removed from filter liquid through distillation. Recrystallization was performed by acetone. 0.7 g of a product was obtained, the yield was 65.5%, and mp was 220° C.

Synthesis of 3,3'-(4-(12-maleimidododecanamido)phenylmethylene)-di-4-hydroxycoumarin 12-maleimidododecanoic acid (294.1 mg, 1 mmol) was dissolved in tetrahydrofuran. DIC (17 μL, 1.1 mmol) and HOBt (148.5 mg, 1.1 mmol) were added and stirred at room temperature for 30 min. Then, the above solution was slowly dripped into a tetrahydrofuran solution of 3,3'-(4-aminophenylmethylene)-di-4-hydroxycoumarin and DIPEA (17.4 μL, 0.1 mmol) and stirred at room temperature over the night. After the result detected by using a thin-layer plate showed that the reaction was completed, reaction liquid was poured into water and was extracted with ethyl acetate three times. The extraction liquid was merged, and was respectively washed with a $K_2CO_3$ solution, 1 M HCl and a saturated salt solution three times. The extraction liquid was added into anhydrous $Na_2SO_4$ and dried over the night. Reduced pressure concentration was performed to obtain a crude product. Column chromatography purification was performed to obtain 51.4 mg of a pure product. The yield was 73%, and mp was 204-206° C.

$^1$H-NMR (DMSO-$d_6$, 300 MHz): δ ppm: 10.17 (s, 1H, —CONH—), 8.31 (d, J=7.8 Hz, 2H, Ar—H), 8.00 (t, J=7.2 Hz, 2H, Ar—H), 7.84 (d, J=8.0 Hz, 2H, Ar—H), 7.76-7.72 (m, 6H, Ar—H), 7.49 (s, 2H, —COCH═CHCO—), 6.70 (s, 1H, —CH—), 3.87 (t, J=7.0 Hz, 2H, —NCH$_2$—), 2.74 (t, J=7.2 Hz, 2H, —COCH$_2$—), 2.05-1.97 (m, 4H, —NCH$_2$CH$_2$(CH$_2$)$_7$CH$_2$—), 1.70 (s, 14H, —NCH$_2$CH$_2$(CH$_2$)$_7$CH$_2$—). ESI-MS m/z: 703.1 [M+H]$^+$.

3. Synthesis and Purification of Chemically Modified OXM Conjugate

The 3,3'-(4-(12-maleimidododecanamido)phenylmethylene)-di-4-hydroxycoumarin obtained in the previous step was dissolved by DMSO and prepared into a solution about 10 mg/mL. The polypeptide main chain was also dissolved in DMSO. After ultrasonic mixing of the two solutions, 20 μl of DIEPA was added and stirred for reaction at room temperature. Reaction conditions were monitored by using LC-MS. The chromatographic conditions were as follows: C18 reversed-phase column (1.7 μm 2.1×50 mm, Waters); mobile phase A: 0.1% formic acid/water (V/V), and mobile phase B: 0.1% formic acid/acetonitrile (V/V); mobile phase gradient: mobile phase B 10%-90%, 2 min, B 90%-90%, 3 min; flow rate: 0.3 mL/min; and ultraviolet detection wavelength: 214 nm. After the reaction was completed, reaction liquid was diluted with acetonitrile containing 1% TFA, was then subjected to high-speed centrifugation, and was filtered by a 0.45 μm microporous filtration membrane. Then, purification was performed by preparative liquid chromatography. The chromatographic conditions were as follows: C18 reversed-phase column (320 mm×28 mm, 5 μm); mobile phase A: 0.1% TFA/water (V/V), and mobile phase B: 0.1% TFA/acetonitrile (V/V); mobile phase gradient: mobile phase B 40%-80%, 30 mm; 80%-85%, 10 min; 85%-95%, 10 min; 95%-40%, 10 min; flow rate: 5 mL/min; and detection wavelength: 214 nm. A collected solution was subjected to reduced pressure concentration to remove acetonitrile. Freeze-drying was performed to obtain 31.6 mg of a pure product. A theoretical relative molecular mass was 4986.6. ESI-MS m/z: Calcd. [M+3H]$^{3+}$ 1663.2, [M+4H]$^{4+}$ 1247.7; Found [M+3H]$^{3+}$ 1663.5, [M+4H]$^{4+}$ 1247.2.

Embodiment 45 Solid-Phase Synthesis of Compound 45

A synthesis method was the same as that of Embodiment 44. The collected solution was freeze-dried to obtain 29.5 mg of a pure product. A theoretical relative molecular mass was 4989.5. ESI-MS m/z: Calcd. [M+3H]$^{3+}$ 1664.2, [M+4H]$^{4+}$ 1248.4; Found [M+3H]$^{3+}$ 1664.5, [M+4H]$^{4+}$ 1248.3.

Embodiment 46 Solid-Phase Synthesis of Compound 46

1. Synthesis of Polypeptide Main Chain

A synthesis method of the polypeptide main chain was the same as that of Embodiment 42.

2. Synthesis of Side Chain 100 mg 2-CTC resin (substitution degree: 0.8 mmol/g) was weighed, swelled with DCM for 30 min, then swelled with 10 mL of NMP for 30 min, and cleanly flushed respectively with 7 mL of NMP and 7 mL of DCM. Fmoc-AEEA (61.6 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into the resin to react for 2 h. After the reaction was completed, reaction liquid was filtered away. 10 mL of solution containing DCM, methanol and DIEA according to a ratio of 5:4:1 was added into resin for blocking reaction for 1 h. Reaction liquid was filtered way. The resin was washed with 7 mL of DCM and 7 mL of NMP 3 times.

A 25% piperidine/NMP (V/V) solution containing 0.1 M HOBt was added into the resin to remove Fmoc. After the reaction was completed, the resin was cleanly washed with NMP. Fmoc-AEEA was coupled again by the same method. After reaction was completed, the resin was washed with 7 mL of DCM and 7 mL of NMP 3 times. A 25% piperidine/NMP (V/V) solution containing 0.1 M HOBt was added into the resin to remove Fmoc. After the reaction was completed, the resin was cleanly washed with NMP. Fmoc-Glu-OtBu (68.0 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into the resin to react for 2 h. After the reaction was completed, reaction liquid was filtered away. The resin was washed with 7 mL of DCM and 7 mL of NMP 3 times. A 25% piperidine/NMP (V/V) solution containing 0.1 M HOBt was added into the resin to remove Fmoc. After the reaction was completed, the resin was cleanly washed with NMP. Octadecanedioic acid mono-tert-butyl ester (59.2 mg, 0.16 mmol), HBTU (60.6 mg, 0.16 mmol), DIEA (55.6 μL, 0.32 mmol) and HOBt (21.6 mg, 0.16 mmol) were dissolved in 10 mL of NMP. This solution was added into resin to react for 2 h. After the reaction was completed, reaction liquid was filtered away. The resin was washed with 7 mL of DCM and 7 mL of NMP 3 times.

The above obtained resin linked with Formula I was put into a reaction bottle. 10 mL of a lysis agent of 20% trifluoroethanol/DCM was added. Shaking was performed at normal temperature for 30 min. After the reaction was completed, suction filtration was performed. A solvent was dried through distillation to obtain 41.6 mg of a crude product of Formula I. A theoretical relative molecular mass was 846.1. ESI-MS m/z: 845.4[M−H$^+$].

3. Conjugation of Polypeptide Main Chain and Side Chain

A 2% hydrazine hydrate solution was added into the resin linked with the main chain peptide sequence to remove a side chain protecting group Dde of Lys at position 16. After the reaction was completed, the resin was cleanly washed with NMP. Side chain small molecules (33.8 mg, 0.04 mmol), HBTU (15.1 mg, 0.04 mmol), HOBt (5.4 mg, 0.04 mmol) and DIPEA (13.9 μL, 0.08 mmol) were dissolved in 10 mL of NMP. Then, this solution was added into the resin to react for 2 h. After the reaction was completed, reaction liquid was filtered away. The resin was washed for with 7 mL of DCM and 7 mL of NMP 3 times. The peptide resin linked with compound 5 was obtained.

4. Lysis of Polypeptide on Resin

The obtained resin linked with compound 5 was put into a reaction bottle. 10 mL of a lysis agent Reagent K (TFA/thioanisole/water/phenol/EDT, 82.5:5:5:5:2.5, V/V) was respectively added. Firstly, shaking was performed at 0° C. for 30 min, and then, reaction was performed at normal temperature for 3 h. After the reaction was completed, suction filtration was performed, and a small amount of TFA and DCM were added for washing three times. Filter liquid was merged. The filter liquid was added into a great amount of glacial ether to separate out white flocculent precipitates. Refrigerated centrifugation was performed to obtain a crude product of the target polypeptide. 95.0 mg of the crude product was finally obtained, and the yield was 94.6%. The reaction was monitored by using HPLC. The chromatographic conditions were as follows: C18 column (150 mm×4.6 mm, 5 μm); mobile phase A: 0.1% TFA/water (V/V), and mobile phase B: 0.1% TFA/acetonitrile (V/V); mobile phase gradient: mobile phase B 35%-85%, 20 min; flow rate: 1 mL/min; column temperature: 40° C.; and detection wavelength: 214 nm. After the reaction was completed, purification was performed by preparative liquid chromatography. The chromatographic conditions were as follows: C18 column (320 mm×28 mm, 5 μm); mobile phase A: 0.1% TFA/water (V/V), and mobile phase B: 0.1% TFA/acetonitrile (V/V); mobile phase gradient: mobile phase B 40%-90%, 20 min; flow rate: δ mL/min; and detection wavelength: 214 nm. A collected solution was freeze-dried to obtain 32.7 mg of a pure product. A theoretical relative molecular mass was 5022.7. ESI-MS m/z: Calcd. [M+3H]$^{3+}$ 1675.2, [M+4H]$^{4+}$ 1256.7; Found [M+3H]$^{3+}$ 1675.9, [M+4H]$^{4+}$ 1256.1.

Embodiment 47 Solid-Phase Synthesis of Compound 47

A synthesis method was the same as that of Embodiment 46. The collected solution was freeze-dried to obtain 26.1 mg of a pure product. A theoretical relative molecular mass was 5025.6. ESI-MS m/z: Calcd. [M+3H]$^{3+}$ 1676.2, [M+4H]$^{4+}$ 1257.4; Found [M+3H]$^{3+}$ 1676.5, [M+4H]$^{4+}$ 1257.7.

Embodiment 48 Solid-Phase Synthesis of Compound 48

A synthesis method was the same as that of Embodiment 42. The collected solution was freeze-dried to obtain 30.1 mg of a pure product. A theoretical relative molecular mass was 4605.3. ESI-MS m/z: Calcd. [M+3H]$^{3+}$ 1536.1, [M+4H]$^{4+}$ 1152.3; Found. [M+3H]$^{3+}$ 1536.5, [M+4H]$^{4+}$ 1152.1.

Embodiment 49 Solid-Phase Synthesis of Compound 49

A synthesis method was the same as that of Embodiment 42. The collected solution was freeze-dried to obtain 29.4 mg of a pure product. A theoretical relative molecular mass was 4608.2. ESI-MS m/z: Calcd. [M+3H]$^{3+}$ 1537.1, [M+4H]$^{4+}$ 1153.1; Found. [M+3H]$^{3+}$ 1537.6, [M+4H]$^{4+}$ 1153.1.

Embodiment 50 Solid-Phase Synthesis of Compound 50

A synthesis method was the same as that of Embodiment 44. The collected solution was freeze-dried to obtain 31.2 mg of a pure product. A theoretical relative molecular mass was 4988.5. ESI-MS m/z: Calcd. [M+3H]$^{3+}$ 1663.8, [M+4H]$^{4+}$ 1248.1; Found [M+3H]$^{3+}$ 1663.4, [M+4H]$^{4+}$ 1248.3.

Embodiment 51 Solid-Phase Synthesis of Compound 51

A synthesis method was the same as that of Embodiment 44. The collected solution was freeze-dried to obtain 32.5 mg of a pure product. A theoretical relative molecular mass was 4991.5. ESI-MS m/z: Calcd. [M+3H]$^{3+}$ 1664.8, [M+4H]$^{4+}$ 1248.9; Found [M+3H]$^{3+}$ 1664.4, [M+4H]$^{4+}$ 1248.6.

Embodiment 52 Solid-Phase Synthesis of Compound 52

A synthesis method was the same as that of Embodiment 46. The collected solution was freeze-dried to obtain 32.3 mg of a pure product. A theoretical relative molecular mass was 5024.7. ESI-MS m/z: Calcd. [M+3H]$^{3+}$ 1675.9, [M+4H]$^{4+}$ 1257.2; Found [M+3H]$^{3+}$ 1675.4, [M+4H]$^{4+}$ 1257.5.

Embodiment 53 Solid-Phase Synthesis of Compound 53

A synthesis method was the same as that of Embodiment 46. The collected solution was freeze-dried to obtain 31.1 mg of a pure product. A theoretical relative molecular mass was 5027.6. ESI-MS m/z: Calcd. $[M+3H]^{3+}$ 1676.9, $[M+4H]^{4+}$ 1257.9; Found $[M+3H]^{3+}$ 1676.7, $[M+4H]^{4+}$ 1257.8.

Embodiment 54 Solid-Phase Synthesis of Compound 54

A synthesis method was the same as that of Embodiment 42. The collected solution was freeze-dried to obtain 29.1 mg of a pure product. A theoretical relative molecular mass was 4604.3. ESI-MS m/z: Calcd. $[M+3H]^{3+}$ 1535.7, $[M+4H]^{4+}$ 1152.1; Found. $[M+3H]^{3+}$ 1535.6, $[M+4H]^{4+}$ 1152.1.

Embodiment 55 Solid-Phase Synthesis of Compound 55

A synthesis method was the same as that of Embodiment 42. The collected solution was freeze-dried to obtain 24.8 mg of a pure product. A theoretical relative molecular mass was 4607.2. ESI-MS m/z: Calcd. $[M+3H]^{3+}$ 1536.7, $[M+4H]^{4+}$ 1152.8; Found. $[M+3H]^{3+}$ 1536.5, $[M+4H]^{4+}$ 1152.6.

Embodiment 56 Solid-Phase Synthesis of Compound 56

A synthesis method was the same as that of Embodiment 44. The collected solution was freeze-dried to obtain 31.1 mg of a pure product. A theoretical relative molecular mass was 4987.6. ESI-MS m/z: Calcd. $[M+3H]^{3+}$ 1663.5, $[M+4H]^{4+}$ 1247.9; Found $[M+3H]^{3+}$ 1663.4, $[M+4H]^{4+}$ 1247.6.

Embodiment 57 Solid-Phase Synthesis of Compound 57

A synthesis method was the same as that of Embodiment 44. The collected solution was freeze-dried to obtain 32.5 mg of a pure product. A theoretical relative molecular mass was 4990.5. ESI-MS m/z: Calcd. $[M+3H]^{3+}$ 1664.5, $[M+4H]^{4+}$ 1248.6; Found $[M+3H]^{3+}$ 1664.4, $[M+4H]^{4+}$ 1248.3.

Embodiment 58 Solid-Phase Synthesis of Compound 58

A synthesis method was the same as that of Embodiment 46. The collected solution was freeze-dried to obtain 32.7 mg of a pure product. A theoretical relative molecular mass was 5023.7. ESI-MS m/z: Calcd. $[M+3H]^{3+}$ 1675.6, $[M+4H]^{4+}$ 1256.9; Found $[M+3H]^{3+}$ 1675.4, $[M+4H]^{4+}$ 1256.6.

Embodiment 59 Solid-Phase Synthesis of Compound 59

A synthesis method was the same as that of Embodiment 46. The collected solution was freeze-dried to obtain 31.6 mg of a pure product. A theoretical relative molecular mass was 5026.6. ESI-MS m/z: Calcd. $[M+3H]^{3+}$ 1676.5, $[M+4H]^{4+}$ 1257.7; Found $[M+3H]^{3+}$ 1676.2, $[M+4H]^{4+}$ 1257.5.

Experimental example: Relevant pharmacological experiment methods and results of OXM hybrid peptides compound 1-24 in the present invention are as follows:

1. GLP-1R and GCGR Receptor Agonistic Activity Screening of OXM Analogs

HEK 293 cells were respectively co-transfected with cDNA encoding GLP-1R or GCGR. In compound determination tests, cells were seeded in a 96-well plate 2 h in advance. The compounds were dissolved with DMSO, diluted to different folds with a culture medium containing 0.1% bovine serum albumin, and added into co-transfected cells. After incubation of the cells for 20 min, fluorescence readings were measured by using an ELISA kit from Cisbo Company and using an enzyme-labeled instrument. A standard curve was established to convert the fluorescence readings into corresponding cAMP values. $EC_{50}$ values of the compounds were calculated by using nonlinear regression of Graphpad Prism 5.0 software.

As shown in Table 1, compared with those of prototype glucagon, the agonistic activity of all compounds on GLP-1R was obviously improved, and the agonistic activity of all compounds on GCGR was slightly reduced. After the compounds are conjugated with fatty acids, the GLP-1R/GCGR receptor agonistic activity was improved to different degrees. The compound 24 was obtained after the compound 6 was conjugated with fatty acids, the GLP-1R receptor agonistic activity was improved by 11.7 times, and the GCGR receptor agonistic activity was improved by 4.4 times.

TABLE 1

Agonistic activity of OMX analogs on GLP-1R and GCGR

| peptides | mGLP1R (pM) | mGCGR (pM) |
| --- | --- | --- |
| OXM | 15.7 ± 0.2 | 6.1 ± 0.2 |
| Exenatide | 5.8 ± 0.6 | >1000 |
| compound 1 | 133.2 ± 1.5**## | 102.5 ± 1.2** |
| compound 2 | 12.4 ± 1.1**## | 7.6 ± 1.7 |
| compound 3 | 15.4 ± 0.6## | 22.5 ± 1.7** |
| compound 4 | 19.5 ± 1.5**## | 62.5 ± 1.2** |
| compound 5 | 6.9 ± 0.9** | 22.1 ± 0.4** |
| compound 6 | 3.8 ± 0.4** | 13.6 ± 1.3** |
| compound 7 | 117.2 ± 1.9**## | 54.1 ± 1.8** |
| compound 8 | 9.3 ± 0.8**## | 3.9 ± 0.9 |
| compound 9 | 11.7 ± 1.0**## | 29.8 ± 0.7** |
| compound 10 | 19.7 ± 0.9**## | 51.8 ± 1.3** |
| compound 11 | 5.1 ± 0.7** | 10.8 ± 1.2** |
| compound 12 | 2.2 ± 1.4**## | 7.1 ± 1.5 |
| compound 13 | 71.9 ± 0.8**## | 33.8 ± 0.9** |
| compound 14 | 5.5 ± 1.5** | 2.4 ± 0.8 |
| compound 15 | 2.2 ± 1.7**## | 17.9 ± 1.4** |
| compound 16 | 14.9 ± 0.8## | 29.8 ± 1.5** |
| compound 17 | 5.7 ± 1.4** | 3.3 ± 1.8 |
| compound 18 | 0.7 ± 0.8**## | 2.8 ± 1.7 |
| compound 19 | 52.2 ± 0.8**## | 27.4 ± 0.6 |

TABLE 1-continued

Agonistic activity of OMX analogs on GLP-1R and GCGR

| peptides | mGLP1R (pM) | mGCGR (pM) |
|---|---|---|
| compound 20 | 3.5 ± 0.8** | 1.6 ± 0.3** |
| compound 21 | 2.3 ± 0.5***## | 128.0 ± 1.9** |
| compound 22 | 11.4 ± 0.9***## | 19.3 ± 1.8** |
| compound 23 | 2.5 ± 0.4***# | 3.4 ± 0.6 |
| compound 24 | 0.3 ± 0.1***## | 2.5 ± 0.3* |

Results are expressed as mean ± SD,
*P < 0.05,
**P < 0.01 vs OXM,
# P < 0.05,
## P < 0.01 vs Exenatide.

2. Intraperitoneal Glucose Tolerance Test of OXM Hybrid Peptides

Normal Kunming mice were randomly divided into groups, 8 mice per group, and were raised in standardized animal houses. Before the test, the mice were fasted for 12 h, and only fed with water. Each group of mice received initial blood glucose value measurement before administration of OXM hybrid peptides, and the time was set to be −30 min. Then, 50 nmol/kg of the OXM hybrid peptides were intraperitoneally injected. After 30 min, 18 mmol/kg of a glucose solution was intraperitoneally injected, the time was set to be 0 min, and a control group was injected with the same volume of saline or 50 nmol/kg of exenatide. Blood glucose levels were measured by a glucose meter at 0, 15, 30, 45, 60 and 120 min, so as to determine the hypoglycemic activity of the OXM hybrid peptides.

TABLE 2

Result of intraperitoneal glucose tolerance test of OXM hybrid peptides

| Group | −30 min | 0 min | 15 min | 30 min | 45 min | 60 min | 120 min |
|---|---|---|---|---|---|---|---|
| saline | 6.16 ± 1.7 | 6.62 ± 1.0 | 22.25 ± 0.4 | 17.89 ± 0.6 | 15.21 ± 0.3 | 10.51 ± 1.8 | 5.76 ± 0.7 |
| Exenatide | 6.21 ± 1.6 | 6.58 ± 1.7 | 7.77 ± 1.6*** | 5.62 ± 1.7*** | 5.32 ± 1.8*** | 7.46 ± 1.8* | 6.32 ± 1.7 |
| compound 1 | 6.27 ± 0.8 | 7.44 ± 0.9 | 6.27 ± 0.8*** | 6.86 ± 0.1*** | 6.74 ± 1.5*** | 5.68 ± 1.2* | 7.07 ± 0.7 |
| compound 2 | 7.98 ± 1.4 | 6.01 ± 1.4 | 6.93 ± 0.0*** | 5.32 ± 1.6*** | 7.05 ± 1.3*** | 7.10 ± 1.2* | 7.94 ± 0.6 |
| compound 3 | 6.05 ± 1.1 | 7.34 ± 1.5 | 6.78 ± 1.1*** | 7.72 ± 1.1*** | 7.23 ± 0.8*** | 7.02 ± 0.8* | 5.67 ± 1.5 |
| compound 4 | 6.48 ± 1.2 | 5.52 ± 0.5 | 6.27 ± 1.3*** | 5.33 ± 0.5*** | 7.12 ± 1.6*** | 7.87 ± 1.1* | 6.68 ± 0.7 |
| compound 5 | 5.06 ± 1.1 | 5.03 ± 1.6 | 6.73 ± 1.4*** | 7.76 ± 0.9*** | 7.65 ± 0.6*** | 7.32 ± 1.2* | 6.83 ± 0.8 |
| compound 6 | 5.87 ± 0.3 | 5.51 ± 0.4 | 7.84 ± 1.0*** | 5.09 ± 1.8*** | 7.75 ± 1.9*** | 7.08 ± 0.4* | 6.17 ± 1.7 |
| compound 7 | 5.83 ± 1.3 | 7.37 ± 0.8 | 7.49 ± 1.7*** | 5.09 ± 0.1*** | 7.65 ± 1.2*** | 6.63 ± 0.2* | 7.39 ± 1.8 |
| compound 8 | 5.97 ± 0.2 | 7.04 ± 1.6 | 6.02 ± 1.7*** | 5.85 ± 1.5*** | 6.29 ± 0.9*** | 7.49 ± 1.1* | 6.57 ± 0.8 |
| compound 9 | 7.43 ± 0.4 | 5.93 ± 0.8 | 6.92 ± 0.5*** | 5.94 ± 1.2*** | 5.00 ± 1.3*** | 7.90 ± 1.4* | 5.49 ± 1.9 |
| compound 10 | 7.16 ± 0.6 | 5.65 ± 1.8 | 6.95 ± 0.5*** | 5.40 ± 0.9*** | 5.30 ± 1.9*** | 6.58 ± 0.3* | 6.81 ± 0.1 |
| compound 11 | 6.82 ± 1.8 | 6.49 ± 1.2 | 6.97 ± 0.2*** | 5.79 ± 0.3*** | 6.87 ± 1.8*** | 7.24 ± 1.1* | 7.31 ± 0.3 |
| compound 12 | 6.62 ± 0.9 | 5.20 ± 1.6 | 7.47 ± 0.8*** | 6.41 ± 1.8*** | 7.52 ± 0.5*** | 6.47 ± 0.5* | 6.25 ± 0.5 |
| compound 13 | 7.00 ± 0.1 | 6.06 ± 1.8 | 6.67 ± 0.2*** | 5.15 ± 1.6*** | 5.14 ± 1.6*** | 5.72 ± 1.8* | 6.03 ± 0.6 |
| compound 14 | 5.95 ± 0.3 | 7.89 ± 1.7 | 5.72 ± 0.7*** | 6.24 ± 1.5*** | 5.17 ± 1.6*** | 6.75 ± 1.7* | 6.85 ± 0.4 |
| compound 15 | 7.32 ± 1.6 | 5.25 ± 0.3 | 7.77 ± 1.6*** | 6.88 ± 1.6*** | 7.91 ± 1.2*** | 5.58 ± 1.1* | 7.17 ± 1.4 |
| compound 16 | 6.92 ± 0.6 | 5.94 ± 1.4 | 5.97 ± 0.1*** | 6.34 ± 1.6*** | 6.55 ± 1.1*** | 7.87 ± 1.5* | 7.60 ± 1.9 |
| compound 17 | 6.90 ± 0.9 | 5.28 ± 1.6 | 7.70 ± 1.1*** | 5.16 ± 1.1*** | 6.02 ± 0.5*** | 7.28 ± 0.9* | 7.98 ± 1.8 |
| compound 18 | 6.19 ± 1.2 | 6.91 ± 1.2 | 5.17 ± 0.7*** | 6.12 ± 0.4*** | 6.69 ± 0.8*** | 7.72 ± 1.7* | 7.11 ± 0.7 |
| compound 19 | 6.99 ± 0.2 | 6.39 ± 70.4 | 6.78 ± 0.6*** | 5.50 ± 0.4*** | 6.41 ± 1.6*** | 5.00 ± 0.1* | 6.24 ± 1.0 |
| compound 20 | 7.79 ± 0.4 | 6.60 ± 1.7 | 5.14 ± 0.9*** | 6.79 ± 0.5*** | 7.61 ± 1.3*** | 6.52 ± 1.2* | 5.59 ± 0.9 |
| compound 21 | 7.16 ± 0.3 | 6.10 ± 1.5. | 5.12 ± 1.8* | 5.52 ± 1.*7 | 5.81 ± 0.9*** | 5.93 ± 0.2* | 5.38 ± 0.7 |
| compound 22 | 5.48 ± 1.5 | 5.76 ± 16 | 5.73 ± 1.9*** | 7.34 ± 0.6*** | 6.17 ± 1.9*** | 6.73 ± 0.9* | 7.88 ± 01.7 |

TABLE 2-continued

Result of intraperitoneal glucose tolerance test of OXM hybrid peptides

| Group | −30 min | 0 min | 15 min | 30 min | 45 min | 60 min | 120 min |
|---|---|---|---|---|---|---|---|
| compound 23 | 6.10 ± 1.2 | 6.10 ± 1.9 | 6.86 ± 1.8*** | 5.94 ± 0.4*** | 7.65 ± 1.2*** | 6.06 ± 0.3* | 5.04 ± 0.1 |
| compound 24 | 5.94 ± 1.4 | 6.86 ± 0.1 | 5.09 ± 1.3*** | 7.41 ± 0.5*** | 7.26 ± 0.5*** | 5.37 ± 0.9* | 7.27 ± 0.1 |

Results are expressed as mean ± SD, *P <0.05, P <0.01, *P <0.001 vs saline.

As shown in Table 2, the hypoglycemic test result shows that when an administration concentration of the OXM hybrid peptides in the present invention was 50 nmol/kg, the hypoglycemic effect was equivalent to the hypoglycemic effect of exenatide.

3. Second Day Glucose Tolerance Test of OXM Hybrid Peptides

After the intraperitoneal glucose tolerance test was completed, the mice immediately and normally ate and drunk for 10 h, and were then fasted for 12 h, and the mouse intraperitoneal glucose tolerance test was performed again. Each group of mice were injected with 18 mmol/kg of a glucose solution intraperitoneally, and the glucose injection time was set to be 0 min. Blood glucose levels were measured by a glucose meter at 0, 15, 30, 45, 60 and 120 min.

As shown in FIG. 1, FIG. 2, FIG. 3 and FIG. 4, the result of the second day glucose tolerance test shows that the OXM hybrid peptides conjugated with the fatty acid side chains in the present invention still had the hypoglycemic effect after being metabolized for 24 h in the body, while exenatide had lost activity for a long time. This shows that the hypoglycemic time of the OXM hybrid peptides obtained after modification was significantly prolonged, and the hypoglycemic action could maintain for nearly 30 h.

4. Blood Glucose Stabilizing Test of OXM Hybrid Peptides

Blood glucose of STZ-induced diabetes model mice was measured. Mice with blood glucose values higher than 20 mmol/L were selected and randomly divided into groups, six mice per group. The mice received free choice feeding during the test. A positive control group was intraperitoneally injected with exenatide or liraglutide at a dose of 50 nmol/kg, a negative control group was intraperitoneally injected with saline, and administration groups were respectively injected with OXM hybrid peptide at a dose of 50 nmol/kg. Compounds were administered at 0 h, and blood glucose levels were measured by using a glucose meter at 0, 0.5, 1, 2, 3, 4, 6, 8, 10, 12, 16, 24, 36, 48 and 60 h. An evaluation index was the time at which the blood glucose value of the mice was lower than 8.35 mmol/L after intraperitoneal injection of the compounds.

Figure 5:
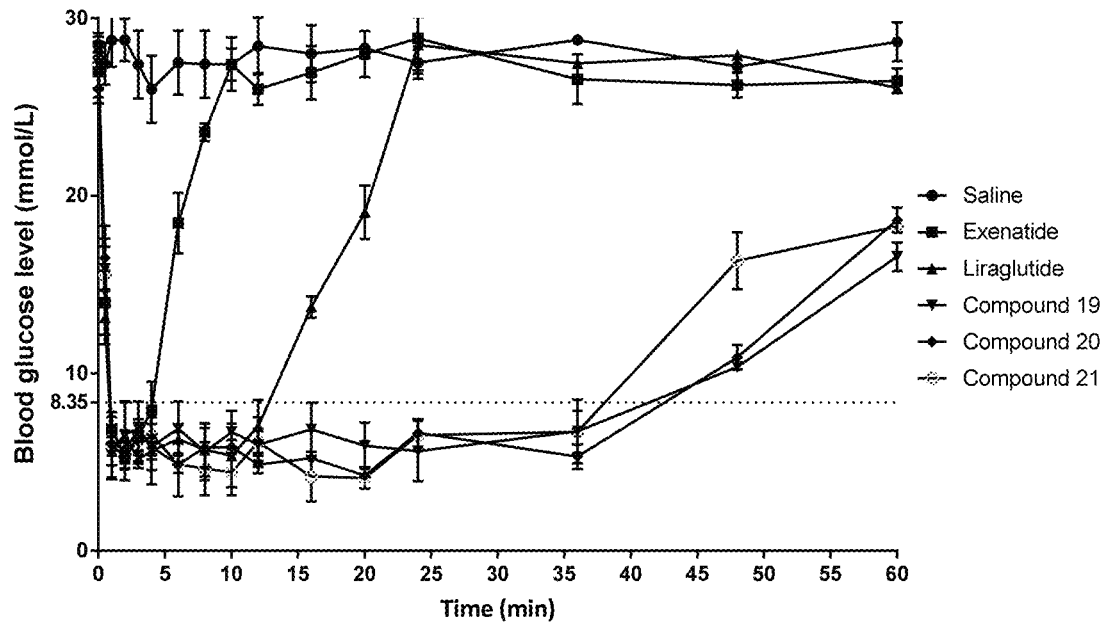
FIG. 5 is a result of a blood glucose stabilizing test of OXM hybrid peptides compound 19-21.
Figure 6:
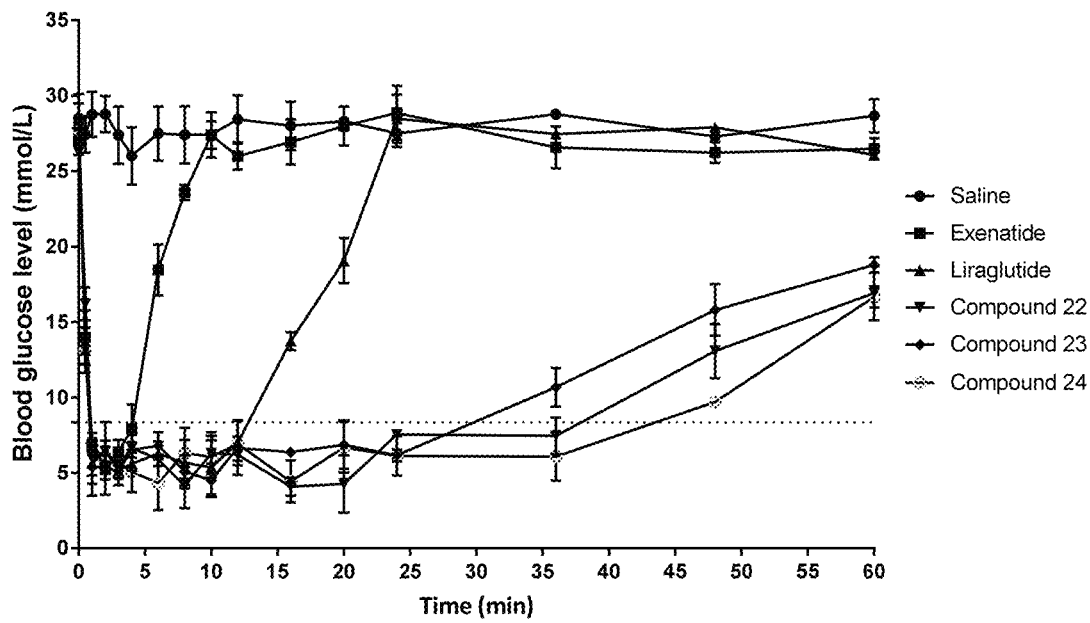
FIG. 6 is a result of a blood glucose stabilizing test of OXM hybrid peptides compound 22-24.
Figure 7:
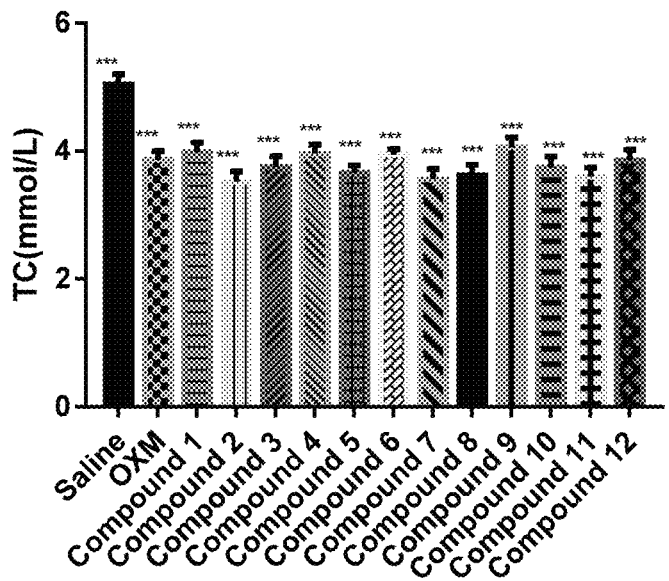
FIG. 7 is a result of TC detection of OXM hybrid peptides compound 1-12.
Figure 8:
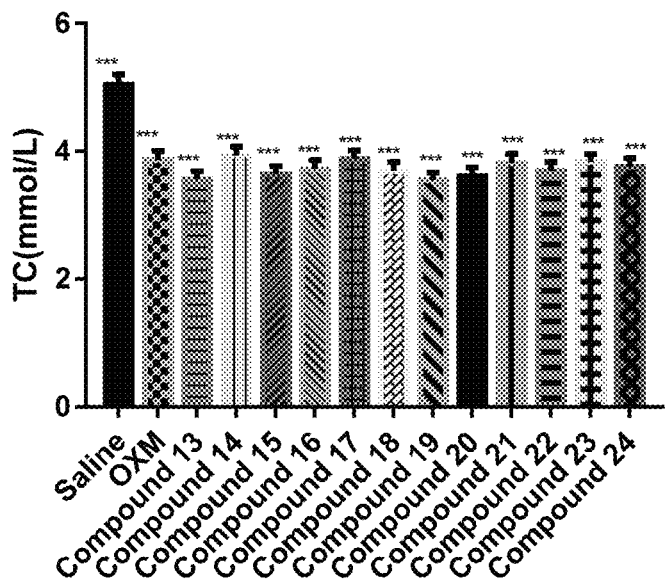
FIG. 8 is a result of TC detection of OXM hybrid peptides compound 13-24.
Figure 9:
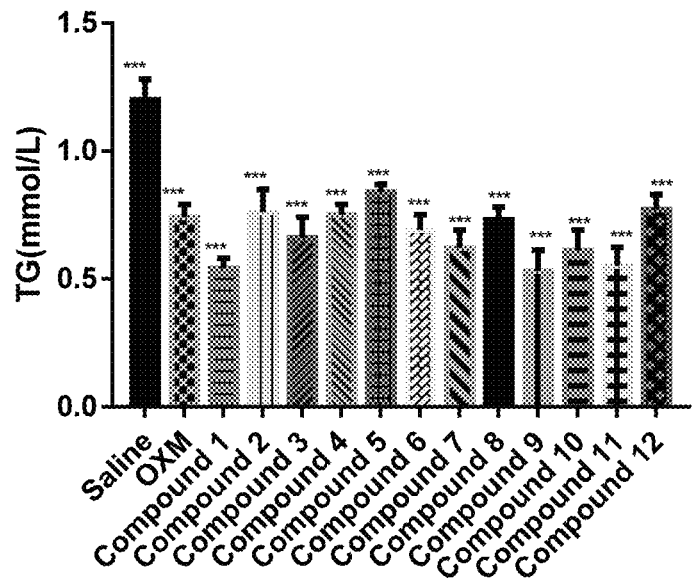
FIG. 9 is a result of TG detection of OXM hybrid peptides compound 1-12.
Figure 10:
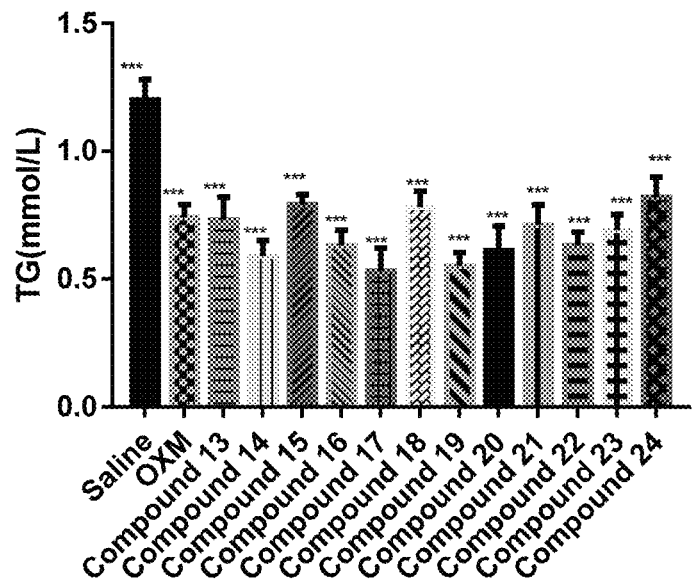
FIG. 10 is a result of TG detection of OXM hybrid peptides compound 13-24.

From FIG. 5 and FIG. 6, it can be seen that the blood glucose stabilizing time of exenatide was only 4.1 h, the blood glucose stabilizing time of liraglutide was 10.7 h, and the blood glucose stabilizing time of the long-acting hypoglycemic polypeptides in the present invention was 40 h or above, and the blood glucose stabilizing time of parts of the long-acting hypoglycemic polypeptides in the present invention could exceed 50 h. The blood glucose stabilizing test shows that the OXM hybrid peptides have a good long-acting hypoglycemic effect, can achieve a better long-acting hypoglycemic effect, and have the potential of being developed into a hypoglycemic medicine administered once every two days.

5. Weight Gain Slowing Test of OXM Hybrid Peptides

Male C57bl/6 mice were fed with high-fat feed for 4 weeks. The mice with body weights greater than 30 g were selected for the test, and were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. Fasting body weights of each group of mice on Day 1 and Day 56 were tested, and the average body weight change of each group of mice was examined.

TABLE 3

Weight gain slowing test of OXM hybrid peptides

| compound | Day 1 | Day 56 |
|---|---|---|
| saline | 32.8 ± 1.4 | 45.6 ± 0.4 |
| OXM | 32.5 ± 0.7 | 40.3 ± 1.3 |
| compound 1 | 31.4 ± 1.7 | 39.9 ± 1.9 |
| compound 2 | 30.9 ± 1.3 | 40.1 ± 0.9 |
| compound 3 | 31.0 ± 1.4 | 40.5 ± 1.6 |
| compound 4 | 30.7 ± 0.6 | 41.2 ± 1.6 |
| compound 5 | 30.8 ± 0.6 | 40.3 ± 0.8 |
| compound 6 | 30.8 ± 0.9 | 40.4 ± 0.9 |
| compound 7 | 31.4 ± 0.8 | 39.0 ± 1.4 |
| compound 8 | 32.3 ± 1.6 | 39.9 ± 0.6 |
| compound 9 | 32.8 ± 0.7 | 35.6 ± 1.6 |
| compound 10 | 31.3 ± 0.6 | 39.3 ± 1.5 |
| compound 11 | 32.3 ± 1.5 | 39.0 ± 0.4 |
| compound 12 | 31.5 ± 0.5 | 38.1 ± 0.7 |
| compound 13 | 32.8 ± 1.5 | 38.2 ± 0.4 |
| compound 14 | 31.9 ± 1.3 | 37.7 ± 1.2 |
| compound 15 | 31.6 ± 1.7 | 36.6 ± 1.4 |
| compound 16 | 31.3 ± 1.5 | 35.9 ± 0.2 |
| compound 17 | 33.5 ± 0.7 | 38.0 ± 1.1 |
| compound 18 | 33.6 ± 0.5 | 37.2 ± 1.3 |
| compound 19 | 32.2 ± 0.8 | 34.9 ± 1.5 |
| compound 20 | 30.3 ± 0.7 | 36.5 ± 0.8 |
| compound 21 | 30.6 ± 1.4 | 36.4 ± 1.1 |
| compound 22 | 32.8 ± 0.4 | 35.4 ± 1.7 |
| compound 23 | 31.4 ± 0.1 | 35.1 ± 1.1 |
| compound 24 | 30.3 ± 1.3 | 33.0 ± 0.1 |

Results are expressed as mean ± SD.

From Table 3, it can be seen that after long-time administration, all compounds showed a better body weight control effect, and the body weight control effect was obviously superior to that of OXM.

6. Blood Lipid Lowering Test of OXM Hybrid Peptides

Male C57bl/6 mice were fed with high-fat feed for 4 weeks. The mice with body weights greater than 30 g were selected for the test, and were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect contents of total cholesterol (TC) and triglyceride (TG).

From FIG. 7-FIG. 10, it can be seen that each lipid parameter of the mice in the saline group was increased, while the lipid parameter of the mice in the administration group was reduced. The result shows that the OXM analogs have a hyperlipidemia treatment effect.

7. Non-Alcoholic Fatty Liver Disease Treatment Test of OXM Hybrid Peptides

Male C57bl/6 mice were fed with high-fat feed for 8 weeks. Non-alcoholic fatty liver disease models were established. The mice were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect the content of alanine aminotransferase.

Figure 11:
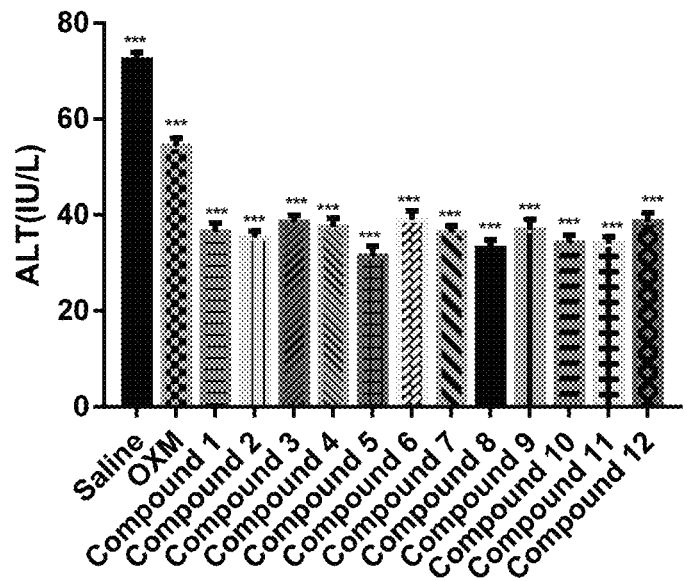
FIG. 11 is a result of ALT detection of OXM hybrid peptides compound 1-12.
Figure 12:
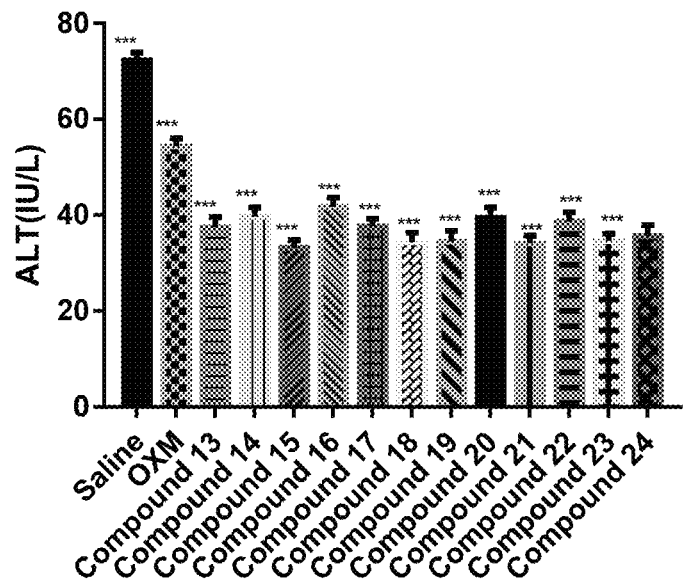
FIG. 12 is a result of ALT detection of OXM hybrid peptides compound 13-24.

From FIG. 11-FIG. 12, it can be seen that the content of alanine aminotransferase (ALT) of the mice in the saline group was increased, and the condition conformed to the pathological features of the non-alcoholic fatty liver disease, while the content of alanine aminotransferase of the mice in the administration group was reduced. The result shows that the OXM analogs have the non-alcoholic fatty liver disease treatment effect.

Relevant pharmacological experiment methods and results of OXM hybrid peptides compound 25-29 in the present invention are as follows:

evaluation index was the time at which the blood glucose value of the mice was lower than 8.35 mmol/L after intraperitoneal injection of the compounds.

Figure 13:
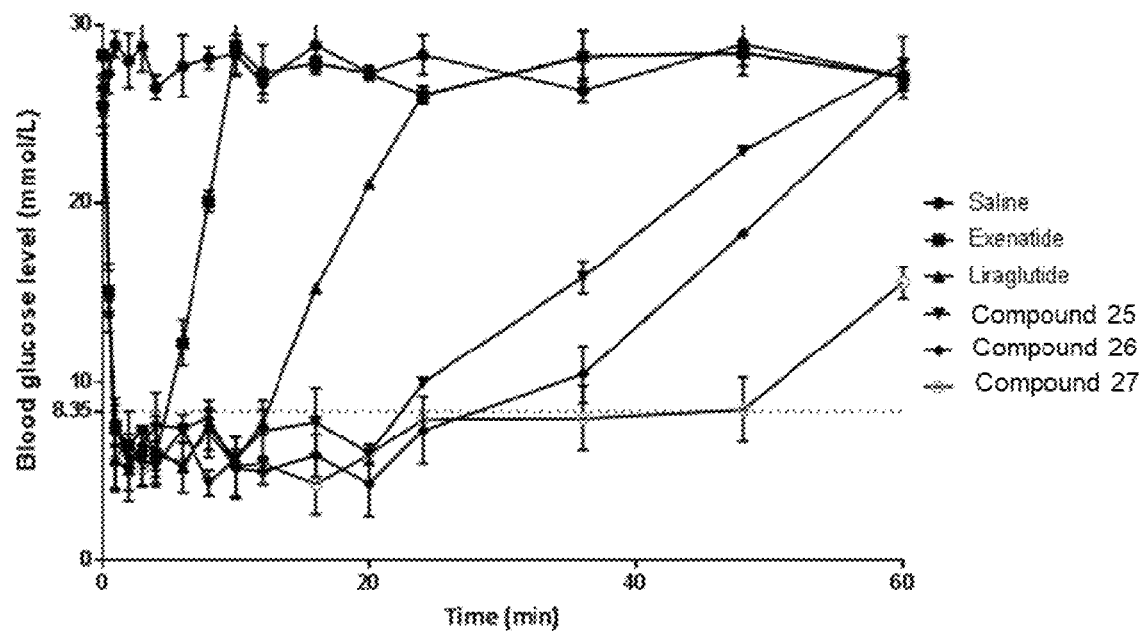
FIG. 13 is a result of a blood glucose stabilizing test of OXM hybrid peptides compound 25-27.
Figure 14:
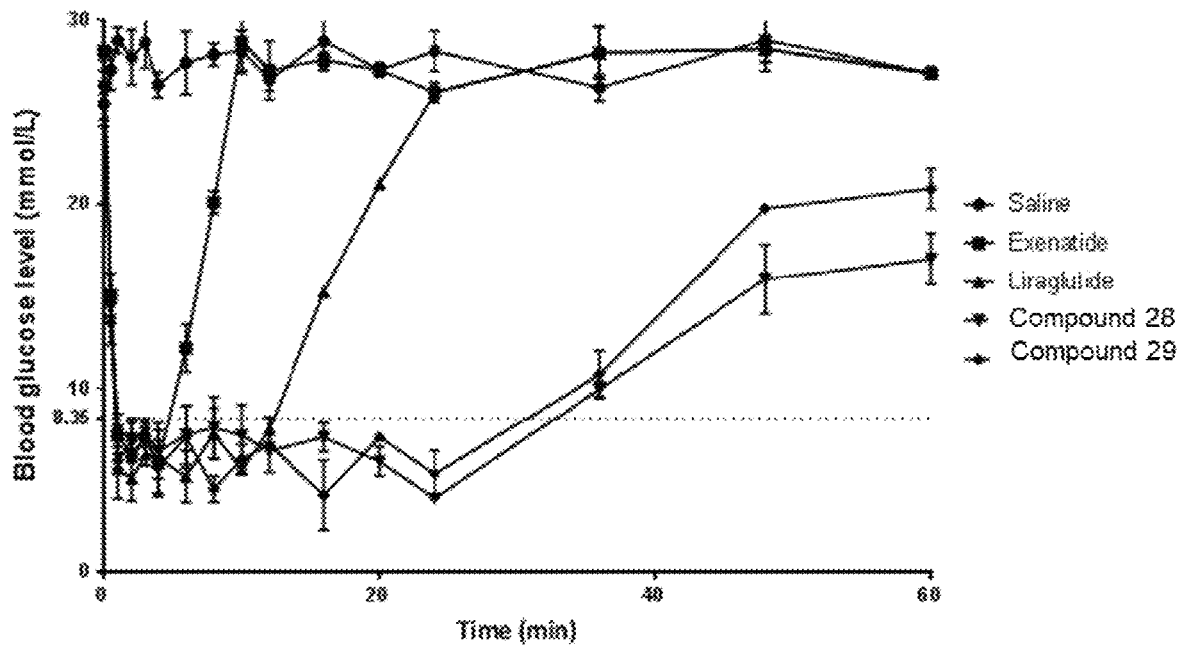
FIG. 14 is a result of a blood glucose stabilizing test of OXM hybrid peptides compound 28-29.

From FIG. 13 and FIG. 14, the blood glucose stabilizing time of exenatide was only 4.7 h, the blood glucose stabilizing time of liraglutide was 12.3 h, and the blood glucose stabilizing time of the long-acting hypoglycemic polypeptides in the present invention could reach 40 h or above. The blood glucose stabilizing test shows that the OXM hybrid peptides have a good long-acting hypoglycemic effect, can achieve a better long-acting hypoglycemic effect, and have the potential of being developed into a hypoglycemic medicine administered once every two days.

3. Weight Gain Slowing Test of OXM Hybrid Peptides

Male C57bl/6 mice were fed with high-fat feed for 4 weeks. The mice with body weights greater than 30 g were selected for the test, and were randomly divided into 7 groups, 8 mice per group. The mice were administrated with OXM hybrid peptides (50 nmol/kg, 10 mL/kg) every day for 56 days, a negative control group was administrated with saline every day, and a positive control group was administrated with OXM. Fasting body weights of each group of mice on Day 1 and Day 56 were tested, and the average body weight change of each group of mice was examined.

TABLE 4

Result of intraperitoneal glucose tolerance test of OXM hybrid peptides

| Group | −30 min | 0 min | 15 min | 30 min | 45 min | 60 min | 120 min |
|---|---|---|---|---|---|---|---|
| saline | 7.35 ± 1.9 | 6.92 ± 0.8 | 21.13 ± 1.5 | 18.52 ± 0.9 | 14.28 ± 1.7 | 10.37 ± 0.9 | 7.78 ± 1.8 |
| Exenatide | 5.53 ± 1.8 | 7.03 ± 0.8 | 7.01 ± 1.1*** | 6.11 ± 0.3*** | 7.31 ± 0.9*** | 7.31 ± 0.3** | 6.56 ± 1.4 |
| compound 25 | 6.98 ± 1.8 | 5.69 ± 1.1 | 5.19 ± 0.9*** | 6.52 ± 1.3*** | 5.23 ± 1.9*** | 6.84 ± 1.3** | 6.06 ± 1.6 |
| compound 26 | 5.71 ± 0.9 | 7.71 ± 0.1 | 7.15 ± 1.1*** | 6.85 ± 0.3*** | 5.41 ± 1.5*** | 6.53 ± 1.4** | 5.79 ± 1.1 |
| compound 27 | 5.81 ± 0.5 | 7.84 ± 1.7 | 7.97 ± 1.4*** | 5.68 ± 1.5*** | 5.27 ± 0.2*** | 6.61 ± 0.3** | 7.58 ± 1.2 |
| compound 28 | 7.81 ± 0.7 | 7.51 ± 1.4 | 6.98 ± 0.6*** | 5.48 ± 0.6*** | 5.10 ± 0.6*** | 6.11 ± 1.1** | 7.23 ± 0.5 |
| compound 29 | 6.41 ± 0.8 | 5.85 ± 1.5 | 5.23 ± 0.4*** | 7.17 ± 1.2*** | 7.09 ± 1.7*** | 6.17 ± 1.4** | 7.47 ± 1.7 |

Results are expressed as mean ± SD, *P <0.05, P <0.01, *P <0.001 vs saline.

As shown in Table 4, the hypoglycemic test result shows that when an administration concentration of the OXM hybrid peptides in the present invention was 50 nmol/kg, the hypoglycemic effect was equivalent to the hypoglycemic effect of exenatide.

2. Blood Glucose Stabilizing Test of OXM Hybrid Peptides

Blood glucose of STZ-induced diabetes model mice was measured. Mice with blood glucose values higher than 20 mmol/L were selected and randomly divided into groups, six mice per group. The mice received free choice feeding during the test. A positive control group was intraperitoneally injected with exenatide or liraglutide at a dose of 50 nmol/kg, a negative control group was intraperitoneally injected with saline, and administration groups were respectively injected with OXM hybrid peptide at a dose of 50 nmol/kg. Compounds were administered at 0 h, and blood glucose levels were measured by using a glucose meter at 0, 0.5, 1, 2, 3, 4, 6, 8, 10, 12, 16, 24, 36, 48 and 60 h. An

TABLE 5

Weight gain slowing test of OXM hybrid peptides

| compound | Day 1 | Day 56 |
|---|---|---|
| saline | 32.5 ± 0.8 | 47.3 ± 1.8 |
| OXM | 31.0 ± 0.8 | 41.0 ± 0.7 |
| compound 25 | 32.7 ± 1.7 | 39.4 ± 0.4 |
| compound 26 | 30.9 ± 0.4 | 38.0 ± 1.1 |
| compound 27 | 30.0 ± 0.5 | 39.1 ± 0.4 |
| compound 28 | 30.4 ± 0.5 | 38.1 ± 1.1 |
| compound 29 | 32.8 ± 1.1 | 37.4 ± 0.7 |

Results are expressed as mean ± SD.

From Table 5, it can be seen that after long-time administration, all compounds showed better body weight control effect, and the body weight control effect was obviously superior to that of OXM.

4. Blood Lipid Lowering Test of OXM Hybrid Peptides

Male C57bl/6 mice were fed with high-fat feed for 4 weeks. The mice with body weights greater than 30 g were selected for the test, and were randomly divided into 7 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect contents of total cholesterol (TC) and triglyceride (TG).

Figure 15:
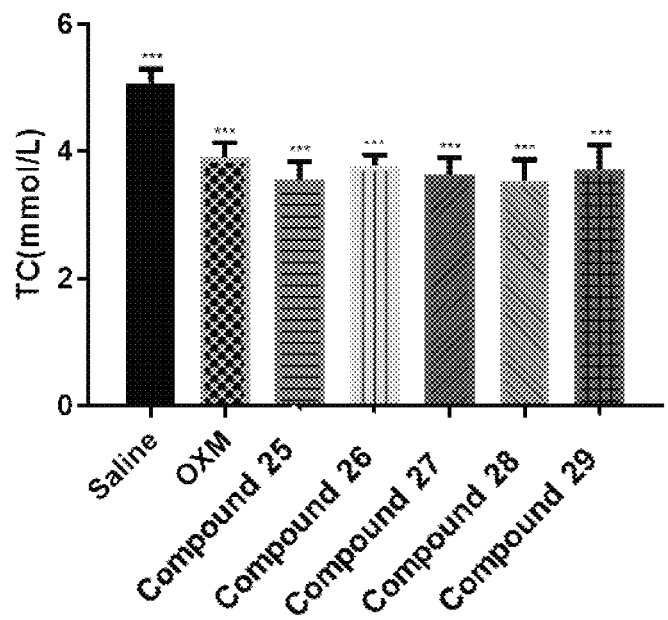
FIG. 15 is a result of TC detection of OXM hybrid peptides compound 25-29.
Figure 16:
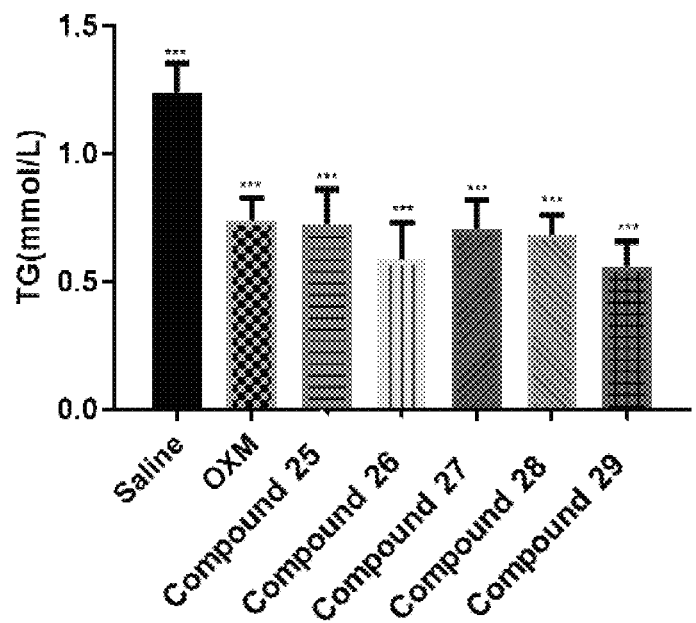
FIG. 16 is a result of TG detection of OXM hybrid peptides compound 25-29.

From FIG. 15-FIG. 16, it can be seen that each lipid parameter of the mice in the saline group was increased, while the lipid parameter of the mice in the administration group was reduced. The result shows that the OXM analogs have a hyperlipidemia treatment effect.

5. Non-Alcoholic Fatty Liver Disease Treatment Test of OXM Hybrid Peptides

Male C57bl/6 mice were fed with high-fat feed for 8 weeks. Non-alcoholic fatty liver disease models were established. The mice were randomly divided into 7 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect the content of alanine aminotransferase.

Figure 17:
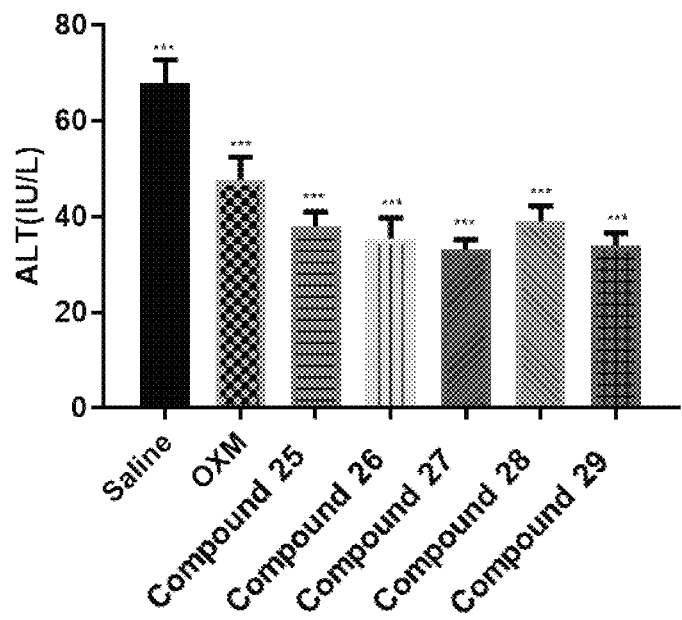
FIG. 17 is a result of ALT detection of OXM hybrid peptides compound 25-29.

From FIG. 17, it can be seen that the content of alanine aminotransferase (ALT) of the mice in the saline group was increased, and the condition conformed to the pathological features of the non-alcoholic fatty liver disease, while the content of alanine aminotransferase of the mice in the administration group was reduced. The result shows that the OXM analogs have the non-alcoholic fatty liver disease treatment effect.

Relevant pharmacological experiment methods and results of OXM hybrid peptides compound 30-35 in the present invention are as follows:

1. GLP-1R and GCGR Receptor Agonistic Activity Screening of OXM Analogs

HEK 293 cells were respectively co-transfected with cDNA encoding GLP-1R or GCGR. Cell lines expressed, and the protein level of GLP-1R or GCGR in the constructed HEK 293 cells was detected by using Western Blot to confirm whether the stable high-expression cell line HEK 293 has been established or not. In compound determination tests, cells were seeded in a 96-well plate 2 h in advance. The compounds were dissolved with DMSO, diluted to different folds with a culture medium containing 0.1% bovine serum albumin, and added into co-transfected cells. After incubation of the cells for 20 min, fluorescence readings were measured by using an ELISA kit from Cisbo Company and using an enzyme-labeled instrument. A standard curve was established to convert the fluorescence readings into corresponding cAMP values. $EC_{50}$ values of the compounds were calculated by using nonlinear regression of Graphpad Prism 5.0 software.

TABLE 6

Agonistic activity of OMX analogs on GLP-1R and GCGR

| peptide | mGLP1R $EC_{50}$ (pM) | mGCGR $EC_{50}$ (pM) |
|---|---|---|
| OXM | 22.6 ± 1.2 | 7.3 ± 0.8 |
| Exenatide | 6.2 ± 0.6 | >1000 |
| compound 30 | 6.4 ± 1.1** | 13.4 ± 0.6** |
| compound 31 | 13.5 ± 0.9**## | 22.8 ± 1.8** |
| compound 32 | 8.2 ± 0.7** | 10.9 ± 0.8* |

TABLE 6-continued

Agonistic activity of OMX analogs on GLP-1R and GCGR

| peptide | mGLP1R $EC_{50}$ (pM) | mGCGR $EC_{50}$ (pM) |
|---|---|---|
| compound 33 | 3.8 ± 0.8** | 12.4 ± 1.2** |
| compound 34 | 22.8 ± 2.1## | 25.4 ± 2.2** |
| compound 35 | 4.6 ± 1.8** | 8.4 ± 1.8 |

Results are expressed as mean ± SD,
*$P < 0.05$,
**$P < 0.01$ vs OXM,
$P < 0.05$,
$P < 0.01$ vs Exenatide.

2. Intraperitoneal Glucose Tolerance Test of OXM Hybrid Peptides

Normal Kunming mice were randomly divided into groups, 8 mice per group, and were raised in standardized animal houses. Before the test, the mice were fasted for 12 h, and only fed with water. Each group of mice received initial blood glucose value measurement before administration of OXM hybrid peptides, and the time was set to be −30 min. Then, 50 nmol/kg of the OXM hybrid peptides were intraperitoneally injected. After 30 min, 18 mmol/kg of a glucose solution was intraperitoneally injected, the time was set to be 0 min, and a control group was injected with the same volume of saline or 50 nmol/kg of exenatide. Blood glucose levels were measured by a glucose meter at 0, 15, 30, 45, 60 and 120 min, so as to determine the hypoglycemic activity of the OXM hybrid peptides.

Figure 18:
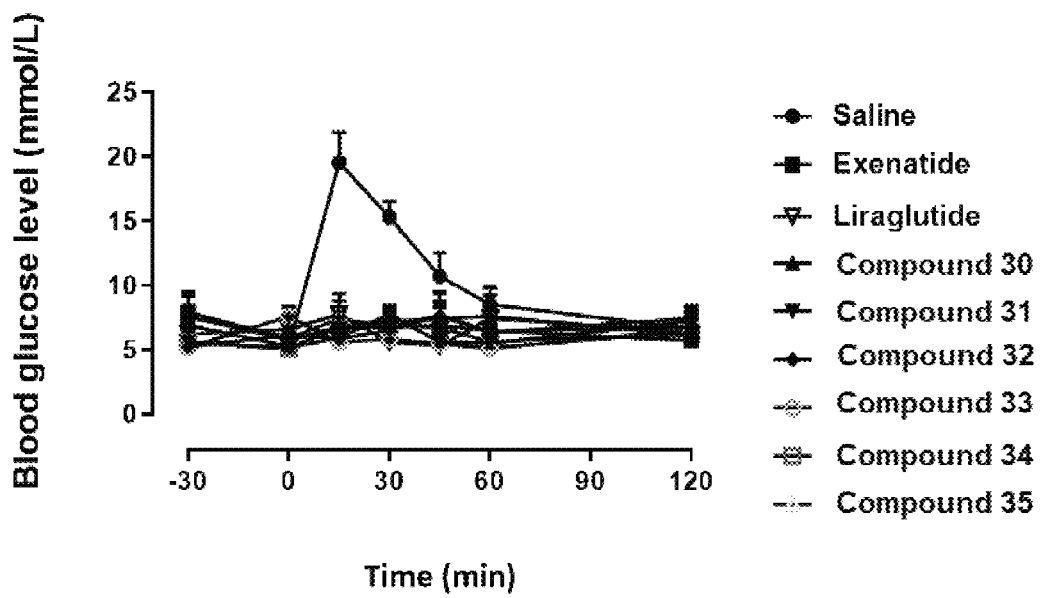
FIG. 18 is a result of an intraperitoneal glucose tolerance test of OXM hybrid peptides compound 30-35.

As shown in FIG. 18, the hypoglycemic test result shows that when an administration concentration of the OXM hybrid peptides in the present invention was 50 nmol/kg, the hypoglycemic effect was equivalent to the hypoglycemic effect of exenatide and liraglutide.

3. Blood Glucose Stabilizing Test of OXM Hybrid Peptides

Blood glucose of STZ-induced diabetes model mice was measured. Mice with blood glucose values higher than 20 mmol/L were selected and randomly divided into groups, six mice per group. The mice received free choice feeding during the test. A positive control group was intraperitoneally injected with exenatide or liraglutide at a dose of 50 nmol/kg, a negative control group was intraperitoneally injected with saline, and administration groups were respectively injected with OXM hybrid peptide at a dose of 50 nmol/kg. Compounds were administered at 0 h, and blood glucose levels were measured by using a glucose meter at 0, 0.5, 1, 2, 3, 4, 6, 8, 10, 12, 16, 24, 36, 48 and 60 h. An evaluation index was the time at which the blood glucose value of the mice was lower than 8.35 mmol/L after intraperitoneal injection of the compounds.

Figure 19:
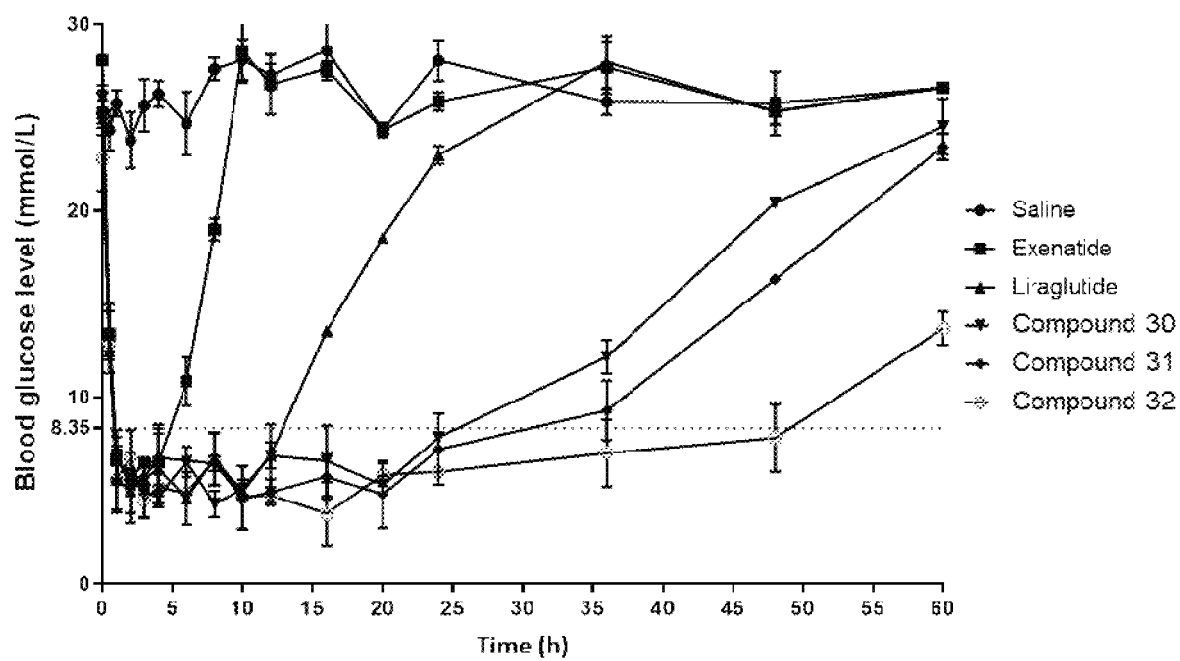
FIG. 19 is a result of a blood glucose stabilizing test of OXM hybrid peptides compound 30-32.
Figure 20:
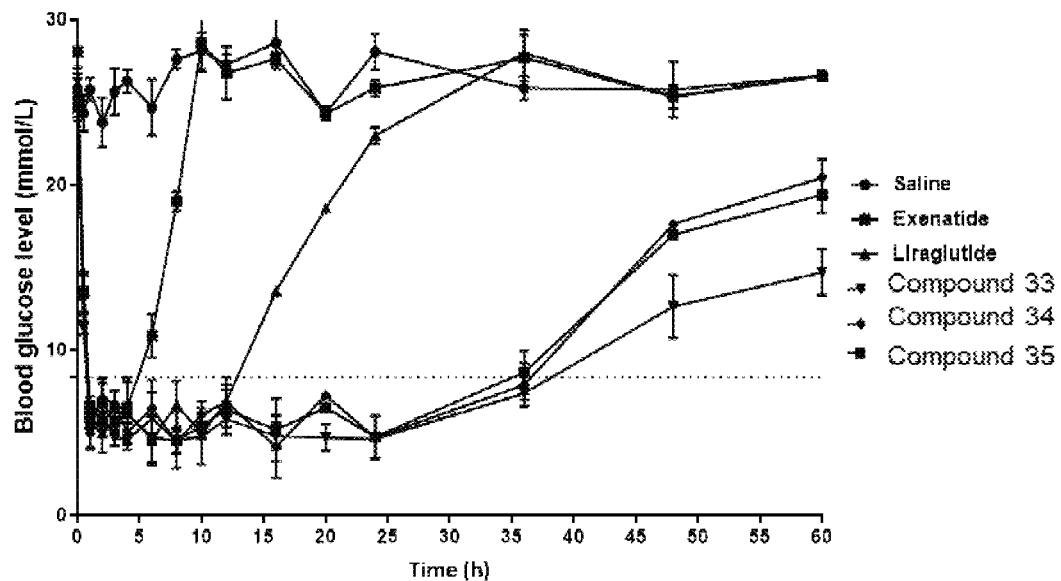
FIG. 20 is a result of a blood glucose stabilizing test of OXM hybrid peptides compound 33-35.

From FIG. 19 and FIG. 20, it can be seen that the blood glucose stabilizing time of exenatide was only 4.0 h, the blood glucose stabilizing time of liraglutide was 12.1 h, and the blood glucose stabilizing time of the long-acting hypoglycemic polypeptides in the present invention could reach 40 h or above. The blood glucose stabilizing test shows that the OXM hybrid peptides have a good long-acting hypoglycemic effect, can achieve a better long-acting hypoglycemic effect, and have the potential of being developed into a hypoglycemic medicine administered once every two days.

4. Weight Gain Slowing Test of OXM Hybrid Peptides

Male C57bl/6 mice were fed with high-fat feed for 4 weeks. The mice with body weights greater than 30 g were selected for the test, and were randomly divided into 8 groups, 8 mice per group. The mice were administered with OXM hybrid peptides (50 nmol/kg, 10 mL/kg) every day for 56 days, a negative control group was administrated with saline every day, and a positive control group was administrated with OXM. Fasting body weights of each group of mice on Day 1 and Day 56 were tested, and the average body weight change of each group of mice was examined.

TABLE 7

The effect of OXM hybrid peptides on slowing down weight gain

| Treatment Group | Day 1 | Day 56 |
|---|---|---|
| saline | 32.5 ± 0.8 | 47.3 ± 1.8 |
| OXM | 30.5 ± 0.6 | 39.6 ± 1.3 |
| compound 30 | 31.9 ± 0.4 | 40.2 ± 1.1 |
| compound 31 | 32.8 ± 1.1 | 37.4 ± 0.7 |
| compound 32 | 32.3 ± 1.5 | 39.6 ± 0.5 |
| compound 33 | 33.4 ± 0.5 | 40.6 ± 0.8 |
| compound 34 | 32.1 ± 0.6 | 38.6 ± 1.5 |
| compound 35 | 29.9 ± 1.4 | 37.8 ± 0.4 |

Results are expressed as mean ± SD.

From Table 7, it can be seen that after long-time administration, all compounds showed a better body weight control effect, and the body weight control effect was obviously superior to that of OXM.

5. Blood Lipid Lowering Test of OXM Hybrid Peptides

Male C57bl/6 mice were fed with high-fat feed for 4 weeks. The mice with body weights greater than 30 g were selected for the test, and were randomly divided into 8 groups, 8 mice per group. The mice were administered with OXM hybrid peptides (50 nmol/kg, 10 mL/kg) every day for 56 days, a negative control group was administrated with saline every day, and a positive control group was administrated with OXM. After the administration was completed, blood serum of mice was taken to detect contents of total cholesterol (TC) and triglyceride (TG).

Figure 21:
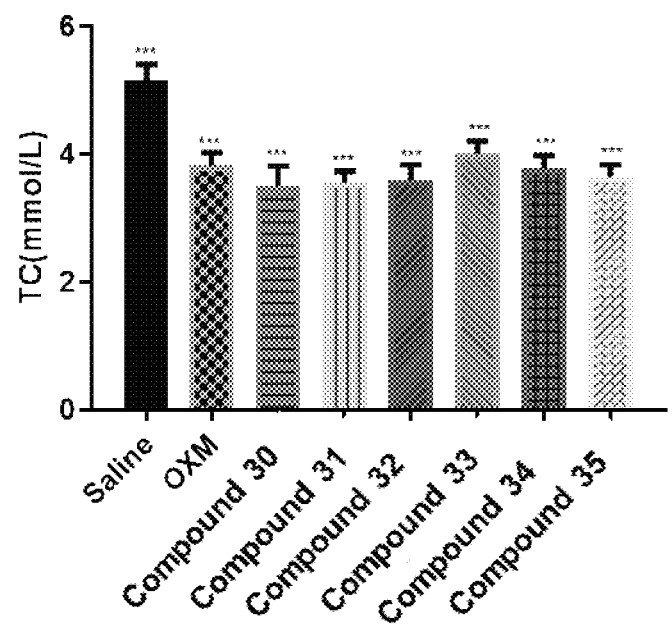
FIG. 21 is a result of TC detection of OXM hybrid peptides compound 30-35.
Figure 22:
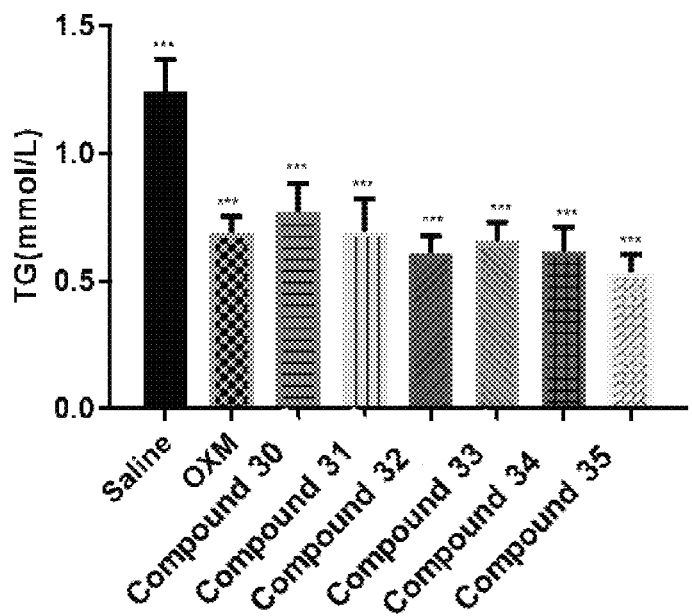
FIG. 22 is a result of TG detection of OXM hybrid peptides compound 30-35.

From FIG. 21-FIG. 22, it can be seen that each lipid parameter of the mice in the saline group was increased, while the lipid parameter of the mice in the administration group was reduced. The result shows that the OXM analogs have a hyperlipidemia treatment effect.

6. Non-Alcoholic Fatty Liver Disease Treatment Test of OXM Hybrid Peptides

Male C57bl/6 mice were fed with high-fat feed for 8 weeks. Non-alcoholic fatty liver disease models were established. The mice were randomly divided into 8 groups, 8 mice per group. The mice were administered with OXM hybrid peptides (50 nmol/kg, 10 mL/kg) every day for 56 days, a negative control group was administrated with saline every day, and a positive control group was administrated with OXM. After the administration was completed, blood serum of mice was taken to detect the content of alanine aminotransferase (ALT).

Figure 23:
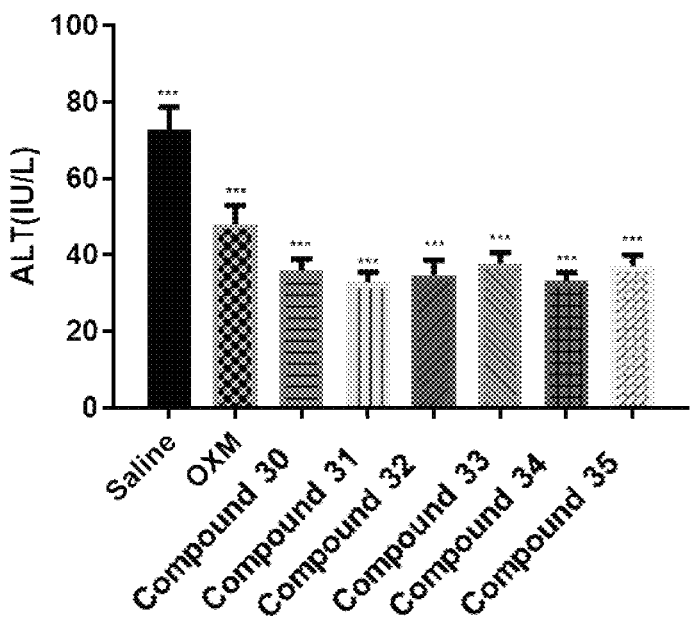
FIG. 23 is a result of ALT detection of OXM hybrid peptides compound 30-35.

From FIG. 23, it can be seen that the content of ALT of the mice in the saline group was increased, and the condition conformed to the pathological features of the non-alcoholic fatty liver disease, while the content of alanine aminotransferase of the mice in the administration group was reduced. The result shows that the OXM analogs have the non-alcoholic fatty liver disease treatment effect.

Relevant pharmacological experiment methods and results of OXM hybrid peptides compound 36-41 in the present invention are as follows:

1. GLP-1R and GCGR Receptor Agonistic Activity Screening of OXM Analogs

HEK 293 cells were respectively co-transfected with cDNA encoding GLP-1R or GCGR. Cell lines expressed, and the protein level of GLP-1R or GCGR in the constructed HEK 293 cells was detected by using Western Blot to confirm whether the stable high-expression cell line HEK 293 has been established or not. In compound determination tests, cells were seeded in a 96-well plate 2 h in advance. The compounds were dissolved with DMSO, diluted to different folds with a culture medium containing 0.1% bovine serum albumin, and added into co-transfected cells. After incubation of the cells for 20 min, fluorescence readings were measured by using an ELISA kit from Cisbo Company and using an enzyme-labeled instrument. A standard curve was established to convert the fluorescence readings into corresponding cAMP values. $EC_{50}$ values of the compounds were calculated by using nonlinear regression of Graphpad Prism 5.0 software.

TABLE 8

Agonistic activity of OMX analogs on GLP-1R and GCGR

| peptide | mGLP1R $EC_{50}$ (pM) | mGCGR $EC_{50}$ (pM) |
|---|---|---|
| OXM | 17.6 ± 0.3 | 6.7 ± 0.2 |
| Exenatide | 6.5 ± 0.6 | >1000 |
| compound 36 | 11.9 ± 1.2**## | 13.4 ± 1.7** |
| compound 37 | 3.4 ± 0.5**## | 6.8 ± 0.4** |
| compound 38 | 6.8 ± 0.2** | 4.6 ± 0.6* |
| compound 39 | 2.5 ± 0.5**## | 1.4 ± 1.1** |
| compound 40 | 7.9 ± 0.9**# | 7.6 ± 0.5** |
| compound 41 | 5.4 ± 0.4** | 8.2 ± 0.8 |

Results are expressed as mean ± SD,
*$P < 0.05$,
**$P < 0.01$ vs OXM,
$P < 0.05$,
$P < 0.01$ vs Exenatide.

2. Intraperitoneal Glucose Tolerance Test of OXM Hybrid Peptides

Normal Kunming mice were randomly divided into groups, 8 mice per group, and were raised in standardized animal houses. Before the test, the mice were fasted for 12 h, and only fed with water. Each group of mice received initial blood glucose value measurement before administration of OXM hybrid peptides, and the time was set to be −30 min. Then, 50 nmol/kg of the OXM hybrid peptides were intraperitoneally injected. After 30 min, 18 mmol/kg of a glucose solution was intraperitoneally injected, the time was set to be 0 min, and a control group was injected with the same volume of saline or 50 nmol/kg of exenatide. Blood glucose levels were measured by a glucose meter at 0, 15, 30, 45, 60 and 120 min, so as to determine the hypoglycemic activity of the OXM hybrid peptides.

Figure 24:
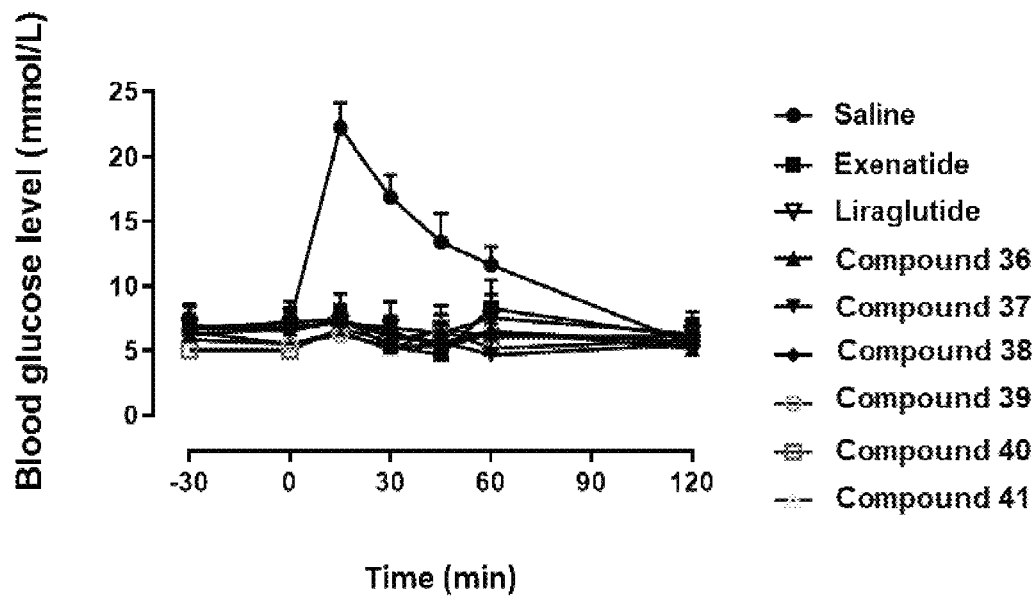
FIG. 24 is a result of an intraperitoneal glucose tolerance test of OXM hybrid peptides compound 36-41.

As shown in FIG. 24, the hypoglycemic test result shows that when an administration concentration of the OXM hybrid peptides in the present invention was 50 nmol/kg, the hypoglycemic effect was equivalent to the hypoglycemic effect of exenatide and liraglutide.

3. Blood Glucose Stabilizing Test of OXM Hybrid Peptides

Blood glucose of STZ-induced diabetes model mice was measured. Mice with blood glucose values higher than 20 mmol/L were selected and randomly divided into groups, six mice per group. The mice received free choice feeding during the test. A positive control group was intraperitoneally injected with exenatide or liraglutide at a dose of 50 nmol/kg, a negative control group was intraperitoneally injected with saline, and administration groups were respectively injected with OXM hybrid peptide at a dose of 50 nmol/kg. Compounds were administered at 0 h, and blood glucose levels were measured by using a glucose meter at 0, 0.5, 1, 2, 3, 4, 6, 8, 10, 12, 16, 24, 36, 48, 60, 72 and 84 h. An evaluation index was the time at which the blood glucose value of the mice was lower than 8.35 mmol/L after intraperitoneal injection of the compounds.

Figure 25:
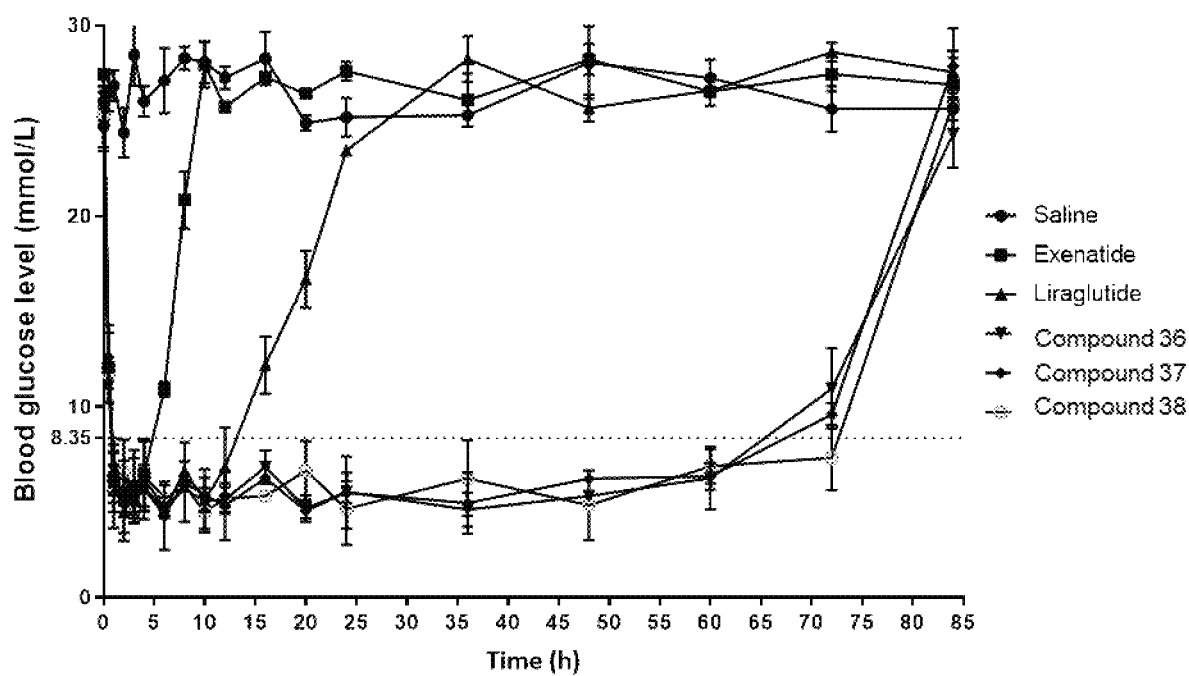
FIG. 25 is a result of a blood glucose stabilizing test of OXM hybrid peptides compound 36-38.
Figure 26:
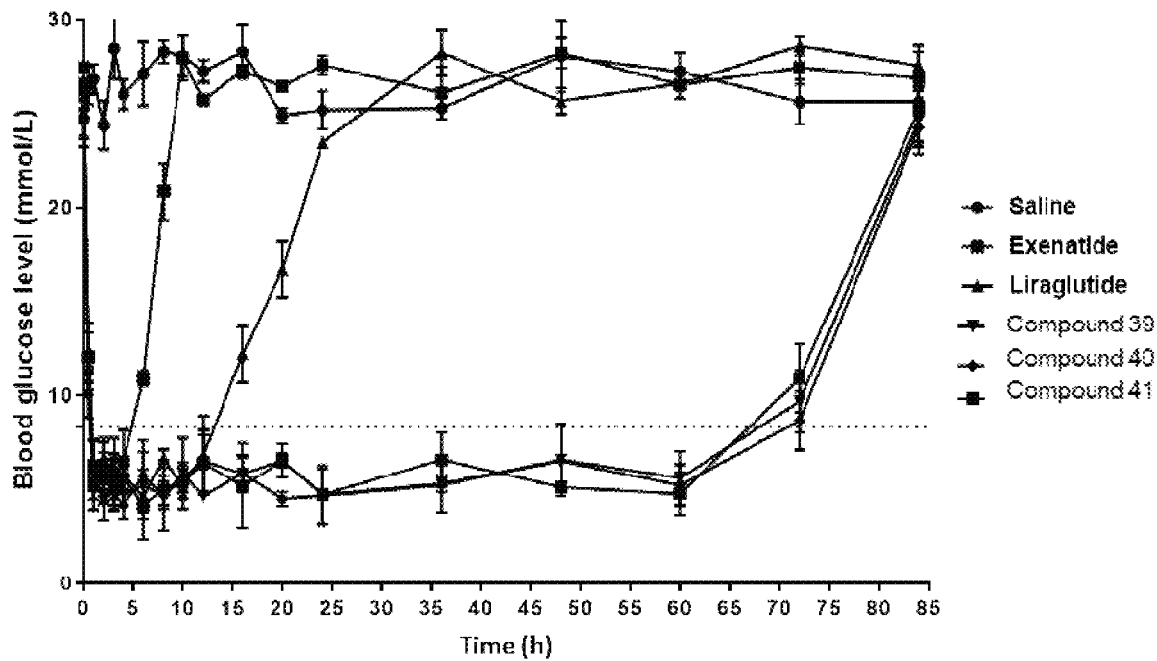
FIG. 26 is a result of a blood glucose stabilizing test of OXM hybrid peptides compound 39-41.

From FIG. 25 and FIG. 26, it can be seen that the blood glucose stabilizing time of exenatide was only 4.0 h, the blood glucose stabilizing time of liraglutide was 12.3 h, and the blood glucose stabilizing time of the long-acting hypoglycemic polypeptides in the present invention could reach 60 h or above. The blood glucose stabilizing test shows that the OXM hybrid peptides have a good long-acting hypoglycemic effect, can achieve a better long-acting hypoglycemic effect, and have the potential of being developed into a hypoglycemic medicine administered once every two days.

4. Weight Gain Slowing Test of OXM Hybrid Peptides

Male C57bl/6 mice were fed with high-fat feed for 4 weeks. The mice with body weights greater than 30 g were selected for the test, and were randomly divided into 8 groups, 8 mice per group. The mice were administrated with OXM hybrid peptides (50 nmol/kg, 10 mL/kg) every day for 56 days, a negative control group was administrated with saline every day, and a positive control group was administrated with OXM. Fasting body weights of each group of mice on Day 1 and Day 56 were tested, and the average body weight change of each group of mice was examined.

TABLE 9

The effect of OXM hybrid peptides on slowing down weight gain

| Treatment Group | Day 1 | Day 56 |
| --- | --- | --- |
| saline | 31.1 ± 0.9 | 48.0 ± 1.8 |
| OXM | 31.9 ± 0.6 | 42.1 ± 1.3 |
| compound 36 | 32.5 ± 0.5 | 40.9 ± 1.1 |
| compound 37 | 33.6 ± 1.1 | 40.1 ± 0.7 |
| compound 38 | 31.9 ± 1.5 | 39.2 ± 0.5 |
| compound 39 | 30.0 ± 0.7 | 38.7 ± 0.8 |
| compound 40 | 33.1 ± 0.5 | 41.9 ± 1.5 |
| compound 41 | 32.8 ± 1.7 | 40.4 ± 0.4 |

Results are expressed as mean ± SD.

From Table 9, it can be seen that after long-time administration, all compounds showed a better body weight control effect, and the body weight control effect was obviously superior to that of OXM.

5. Blood Lipid Lowering Test of OXM Hybrid Peptides

Male C57bl/6 mice were fed with high-fat feed for 4 weeks. The mice with body weights greater than 30 g were selected for the test, and were randomly divided into 8 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect contents of total cholesterol (TC) and triglyceride (TG).

Figure 27:
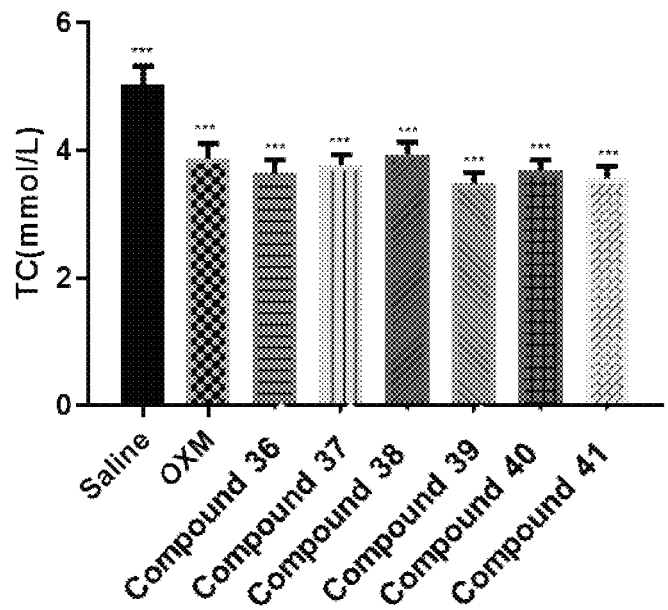
FIG. 27 is a result of TC detection of OXM hybrid peptides compound 36-41.
Figure 28:
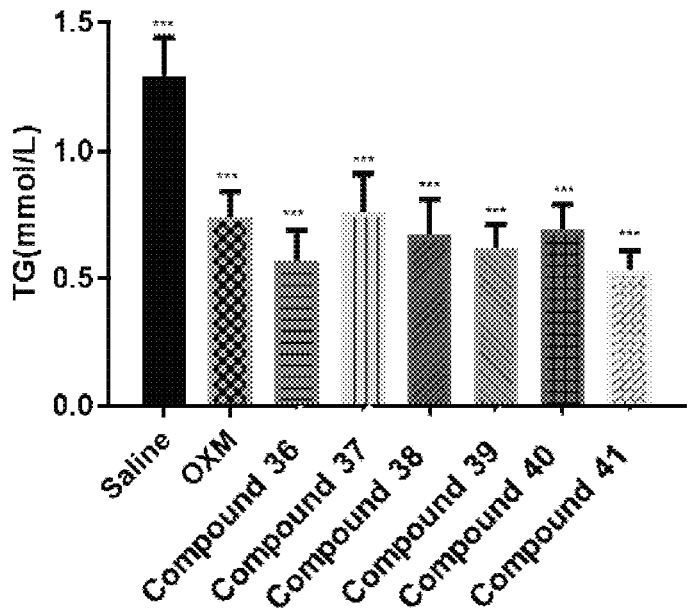
FIG. 28 is a result of TG detection of OXM hybrid peptides compound 36-41.

From FIG. 27-FIG. 28, it can be seen that each lipid parameter of the mice in the saline group was increased, while the lipid parameter of the mice in the administration group was reduced. The result shows that the OXM analogs have a hyperlipidemia treatment effect.

6. Non-Alcoholic Fatty Liver Disease Treatment Test of OXM Hybrid Peptides

Male C57bl/6 mice were fed with high-fat feed for 8 weeks. Non-alcoholic fatty liver disease models were established. The mice were randomly divided into 8 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect the content of alanine aminotransferase (ALT).

Figure 29:
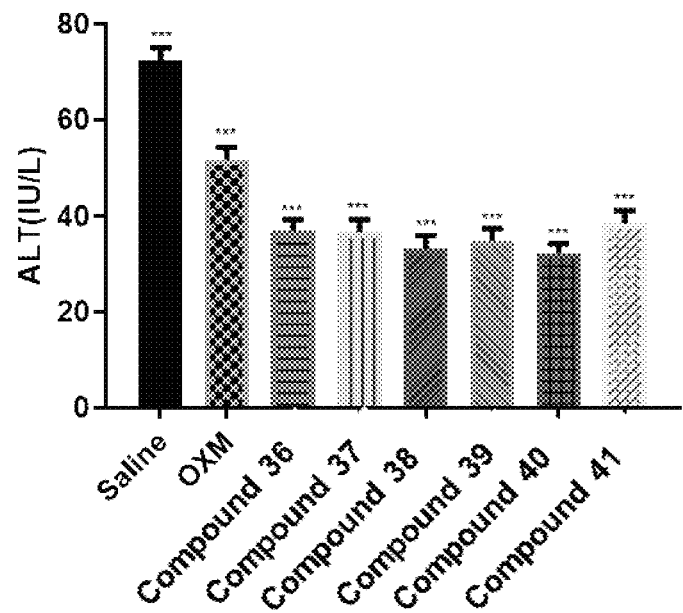
FIG. 29 is a result of ALT detection of OXM hybrid peptides compound 36-41.
Figure 30:
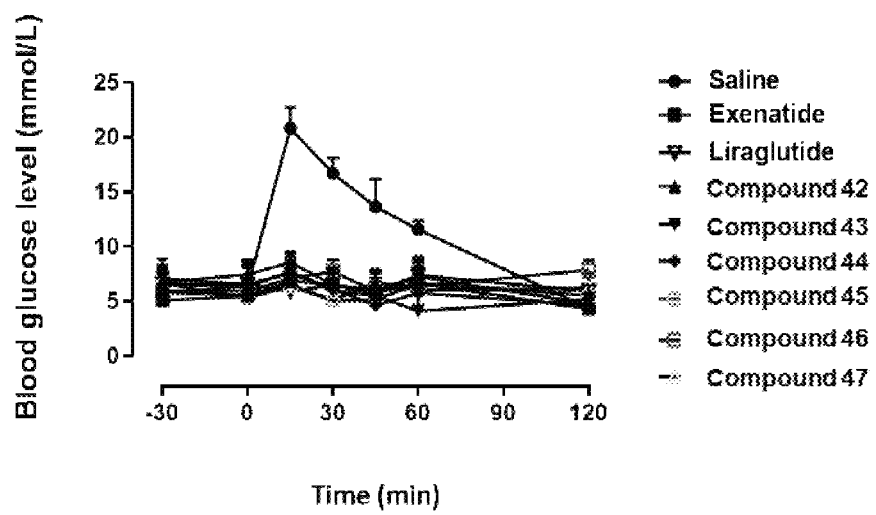
FIG. 30 is a result of an intraperitoneal glucose tolerance test of OXM hybrid peptides compound 42-47.
Figure 31:
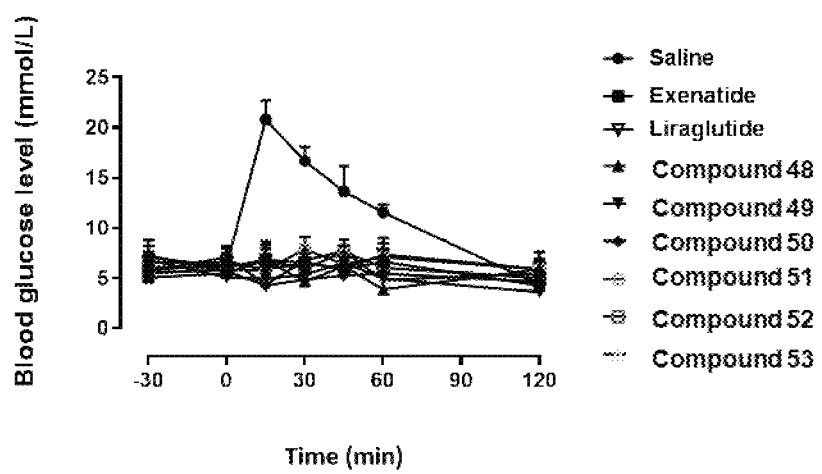
FIG. 31 is a result of an intraperitoneal glucose tolerance test of OXM hybrid peptides compound 48-53.
Figure 32:
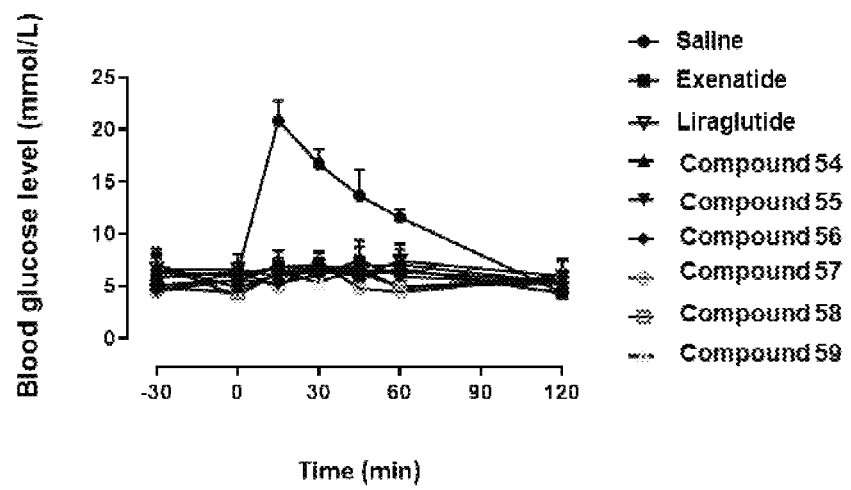
FIG. 32 is a result of an intraperitoneal glucose tolerance test of OXM hybrid peptides compound 54-59.
Figure 33:
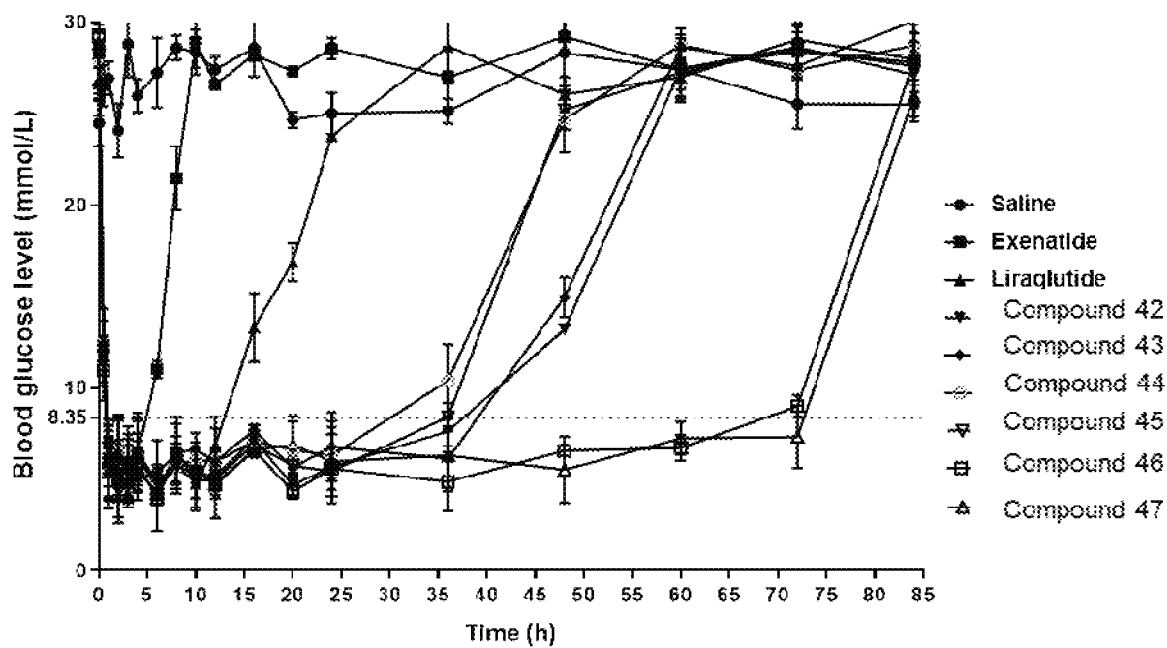
FIG. 33 is a result of a blood glucose stabilizing test of OXM hybrid peptides compound 42-47.
Figure 34:
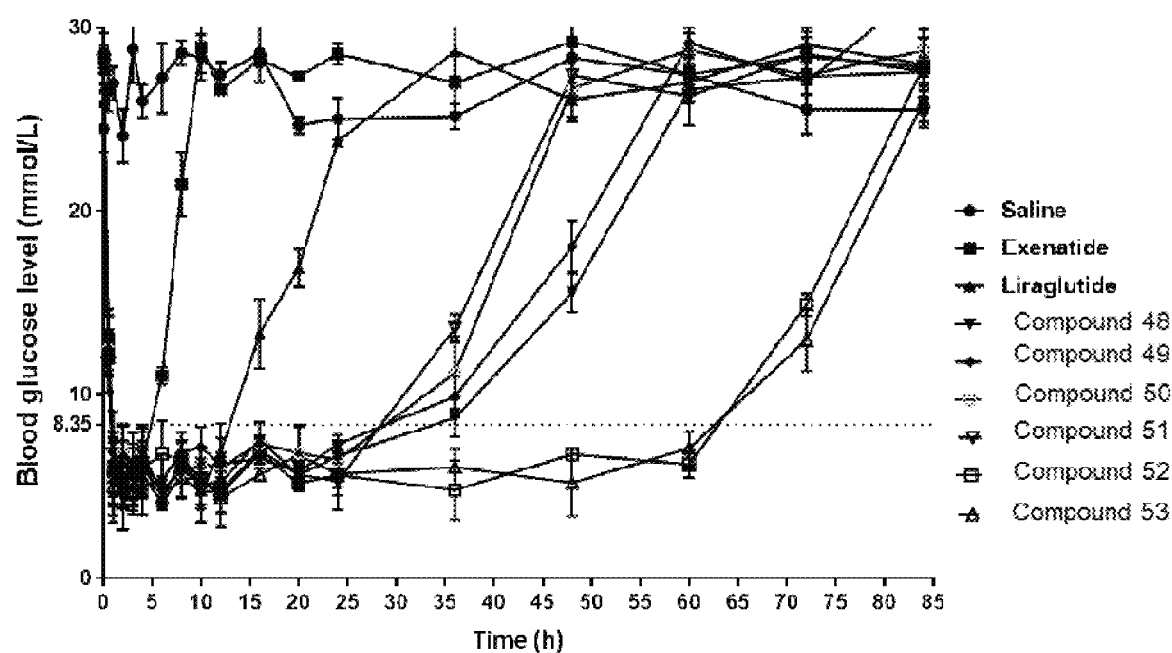
FIG. 34 is a result of a blood glucose stabilizing test of OXM hybrid peptides compound 48-53.
Figure 35:
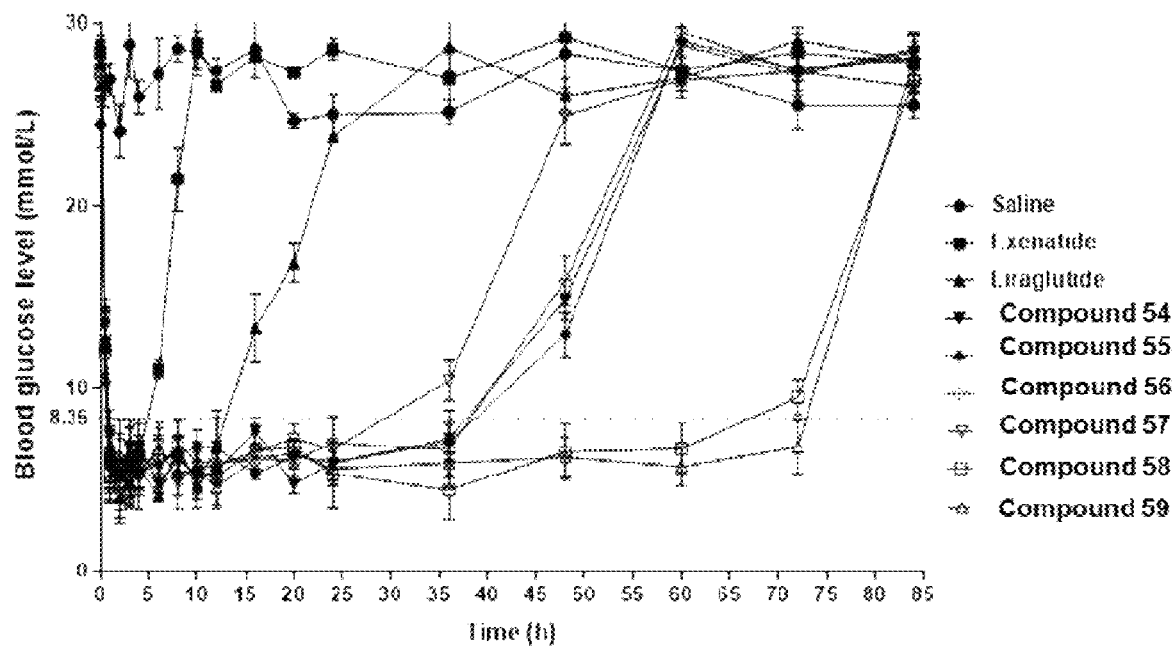
FIG. 35 is a result of a blood glucose stabilizing test of OXM hybrid peptides compound 54-59.
Figure 36:
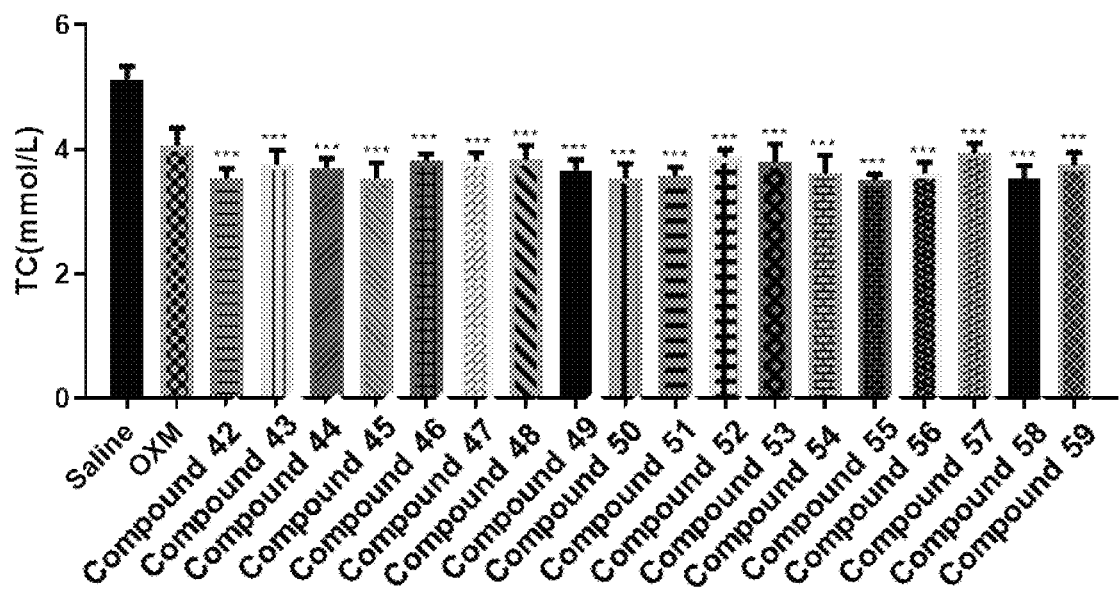
FIG. 36 is a result of TC detection of OXM hybrid peptides compound 42-59.
Figure 37:
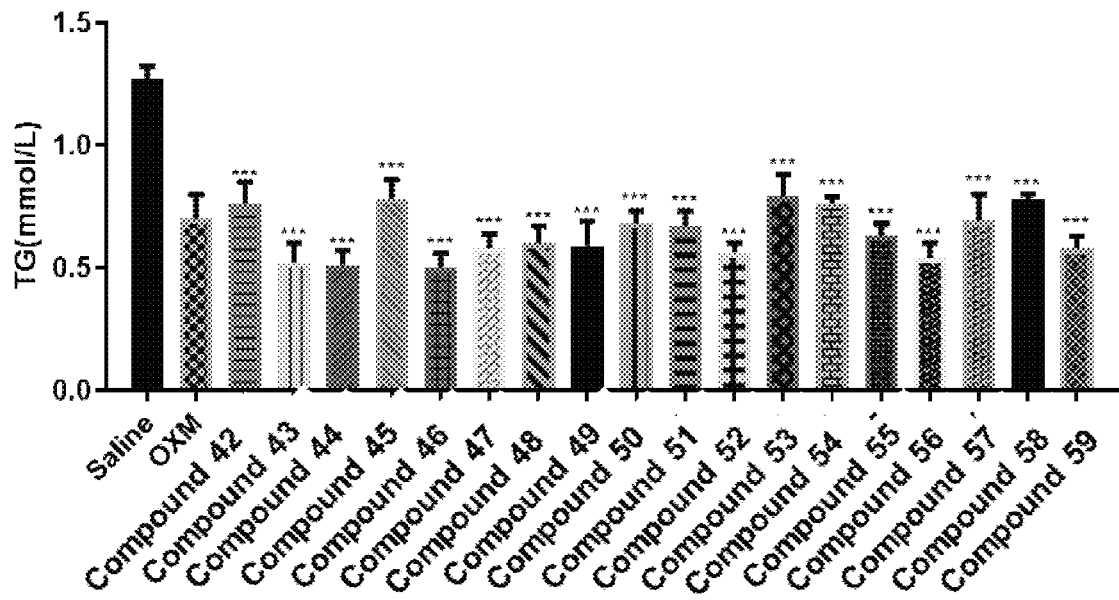
FIG. 37 is a result of TG detection of OXM hybrid peptides compound 42-59.

From FIG. 29, it can be seen that the content of ALT of the mice in the saline group was increased, and the condition conformed to the pathological features of the non-alcoholic fatty liver disease, while the content of alanine aminotransferase of the mice in the administration group was reduced. The result shows that the OXM analogs have the non-alcoholic fatty liver disease treatment effect.

Relevant pharmacological experiment methods and results of OXM hybrid peptides compound 42-59 in the present invention are as follows:

1. Stability Test of OXM Hybrid Peptides on DPP-4 Enzyme 5 nmol of OXM hybrid peptides and 5 mU of DPP-4 enzyme were put into 200 μL of a Tris-HCL buffer solution with a concentration of 50 mM. Under the condition of pH 7.4, incubation was performed for 8 h at 37° C. After the reaction was completed, 10 L of a 20% acetonitrile/water solution was added for terminating the reaction. Incubation solutions at 0 h and 8 h were taken, treated and subjected to HPLC analysis under the following analysis conditions: C18 reversed-phase column (150 mm×4.6 mm, 5 μm); mobile phase A: 0.1% TFA/water (V/V), and mobile phase B: 0.1% TFA/acetonitrile (V/V); mobile phase gradient: mobile phase B 10%-45%, 22 min; flow rate: 1 mL/min; column temperature: 40° C.; and detection wavelength: 214 nm. The stability condition of OXM analogs on the DPP-4 was expressed by a ratio (% intact peptide after 8 h) of the HPLC peak area of the incubation solution at 8 h to the HPLC peak area of the incubation solution at 0 h.

TABLE 10

Agonistic activity of OXM analogs on GLP-1R and GCGR

| peptides | % intact peptide after 8 h |
| --- | --- |
| GLP-1 | 4.3 ± 6.2 |
| OXM | 39.1 ± 5.9 |
| compound 42 | 99.3 ± 1.2 |
| compound 43 | 98.6 ± 0.8 |
| compound 44 | 99.1 ± 1.1 |
| compound 45 | 98.4 ± 1.8 |
| compound 46 | 98.6 ± 0.4 |
| compound 47 | 99.2 ± 0.5 |
| compound 48 | 98.7 ± 1.3 |
| compound 49 | 99.1 ± 0.4 |
| compound 50 | 99.2 ± 0.8 |
| compound 51 | 98.4 ± 0.3 |
| compound 52 | 98.7 ± 0.4 |
| compound 53 | 99.1 ± 0.4 |
| compound 54 | 97.5 ± 1.3 |
| compound 55 | 97.9 ± 0.3 |
| compound 56 | 98.1 ± 0.8 |
| compound 57 | 98.9 ± 1.8 |
| compound 58 | 98.5 ± 1.6 |
| compound 59 | 98.5 ± 0.3 |

From Table 10, it can be seen that through an 8 h enzymatic degradation stability test, the stability of the OXM analogs on the DPP-4 enzyme was much higher than that of OXM prototype and GLP-1 prototype.

2. Intraperitoneal Glucose Tolerance Test of OXM Hybrid Peptides

Normal Kunming mice were randomly divided into groups, 6 mice per group, and were raised in standardized animal houses. Before the test, the mice were fasted for 12 h, and only water was given. Each group of mice received initial blood glucose value measurement before administration of OXM hybrid peptides, and the time was set to be −30 min. Then, 50 nmol/kg of the OXM hybrid peptides were intraperitoneally injected. After 30 min, 18 mmol/kg of a glucose solution was intraperitoneally injected, the time was set to be 0 min, and a control group was injected with the same volume of saline or 50 nmol/kg of exenatide. Blood glucose levels were measured by a glucose meter at 0, 15, 30, 45, 60 and 120 min, so as to determine the hypoglycemic activity of the OXM hybrid peptides.

As shown in FIGS. 30-33, the hypoglycemic test result shows that when an administration concentration of the OXM hybrid peptides in the present invention is 50 nmol/kg, a hypoglycemic effect is equivalent to that of exenatide and liraglutide.

3. Blood Glucose Stabilizing Test of OXM Hybrid Peptides

Blood glucose of STZ-induced diabetes model mice was measured. Mice with blood glucose values higher than 20 mmol/L were selected and randomly divided into groups, six mice per group. The mice received free choice feeding during the test. A positive control group was intraperitoneally injected with exenatide or liraglutide at a dose of 50 nmol/kg, a negative control group was intraperitoneally injected with saline, and administration groups were respectively injected with OXM hybrid peptide at a dose of 50 nmol/kg. Compounds were administered at 0 h, and blood glucose levels were measured by using a glucose meter at 0, 0.5, 1, 2, 3, 4, 6, 8, 10, 12, 16, 24, 36, 48, 60, 72 and 84 h. An evaluation index was the time at which the blood glucose value of the mice was lower than 8.35 mmol/L after intraperitoneal injection of the compounds.

From FIGS. 34-37, it can be seen that the blood glucose stabilizing time of exenatide was only 4.0 h, the blood glucose stabilizing time of liraglutide was 12.3 h, and the blood glucose stabilizing time of the long-acting hypoglycemic polypeptides in the present invention could reach longer than 60 h. The blood glucose stabilizing test shows that the OXM hybrid peptides have a good long-acting hypoglycemic effect, can achieve a better long-acting hypoglycemic effect, and have the potential of being developed into a hypoglycemic medicine administered once every three days.

4. Weight Gain Slowing Test of OXM Hybrid Peptides

Male C57bl/6 mice were fed with high-fat feed for 4 weeks. The mice with body weights greater than 30 g were selected for the test, and were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. Fasting body weights of each group of mice on Day 1 and Day 56 were tested, and the average body weight change of each group of mice was examined.

TABLE 11

The effect of OXM hybrid peptides on slowing down weight gain

| Treatment Group | Day 1 | Day 56 |
| --- | --- | --- |
| saline | 31.7± | 48.6 ± 3.1 |
| OXM | 32.7 | 43.3± |
| compound 42 | 32.7± | 40.7 ± 0.8 |
| compound 43 | 33.3± | 40.4 ± 0.6 |
| compound 44 | 30.6± | 40.5 ± 0.7 |
| compound 45 | 31.8± | 39.7 ± 1.5 |
| compound 46 | 30.7± | 39.8 ± 1.3 |
| compound 47 | 31.9± | 40.7 ± 0.9 |
| compound 48 | 33.8± | 39.3 ± 1.7 |
| compound 49 | 31.7± | 41.3 ± 1.4 |
| compound 50 | 30.1± | 39.5 ± 1.6 |
| compound 51 | 30.2 | 39.3± |
| compound 52 | 33.5 | 41.1± |
| compound 53 | 32.7 | 39.1± |
| compound 54 | 33.6 | 40.8± |
| compound 55 | 32.5 | 41.1± |
| compound 56 | 31.5 | 41.4± |
| compound 57 | 31.6 | 40.8± |
| compound 58 | 30.6 | 40.5± |
| compound 59 | 30.7 | 39.1± |

Results are expressed as mean ± SD.

From Table 11, it can be seen that after long-time administration, all compounds showed a better body weight control effect, and the body weight control effect was obviously superior to that of OXM.

5. Blood Lipid Lowering Test of OXM Hybrid Peptides

Male C57bl/6 mice were fed with high-fat feed for 4 weeks. The mice with body weights greater than 30 g were selected for the test, and were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect contents of total cholesterol (TC) and triglyceride (TG).

Figure 38:
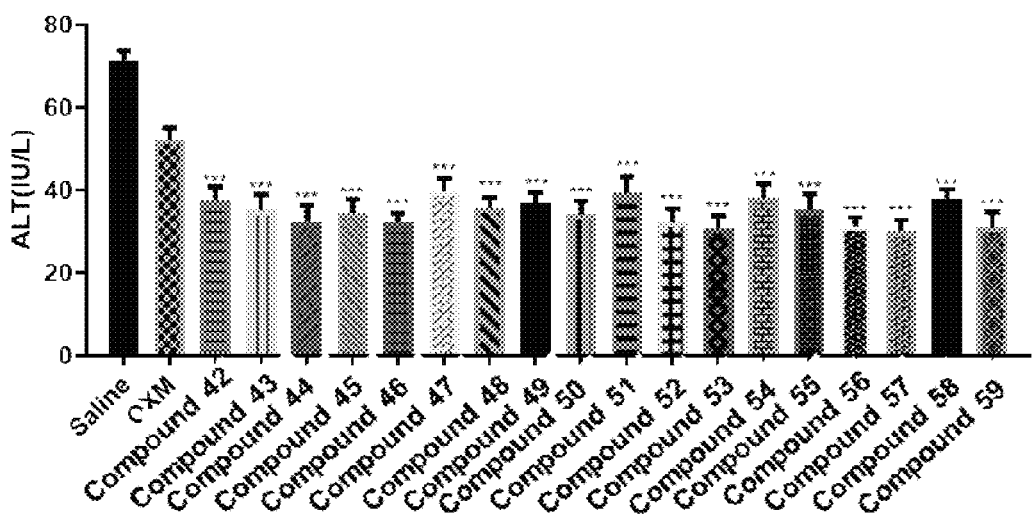
FIG. 38 is a result of ALT detection of OXM hybrid peptides compound 42-59.

From FIG. 38 and FIG. 39, it can be seen that each lipid parameter of the mice in the saline group was increased, while the lipid parameter of the mice in the administration group was reduced. The result shows that the OXM analogs have a hyperlipidemia treatment effect.

6. Non-Alcoholic Fatty Liver Disease Treatment Test of OXM Hybrid Peptides

Male C57bl/6 mice were fed with high-fat feed for 8 weeks. Non-alcoholic fatty liver disease models were established. The mice were randomly divided into 26 groups, 8 mice per group. The mice were administrated with OXM hybrid peptides (50 nmol/kg, 10 mL/kg) every day for 56 days, a negative control group was administrated with saline every day, and a positive control group was administrated with OXM. After the administration was completed, blood serum of mice was taken to detect the content of alanine aminotransferase (ALT).

From FIG. 40, it can be seen that the content of ALT of the mice in the saline group was increased, and the condition conformed to the pathological features of the non-alcoholic fatty liver disease, while the content of alanine aminotransferase of the mice in the administration group was reduced. The result shows that the OXM analogs have the non-alcoholic fatty liver disease treatment effect.

What is claimed is:

1. A compound having a general formula His-Xaa1-PP1-Xaa2-PP2-Xaa3 and its pharmaceutically acceptable salt, wherein PP1 is a polypeptide selecting from the group of polypeptides having the amino acid sequences shown as SEQ ID NO.:02, SEQ ID NO.:04 and SEQ ID NO.:05; PP2 is a polypeptide selecting from the group of polypeptides having the amino acid sequences shown as SEQ ID NO.:03, SEQ ID NO.:06, SEQ ID NO.:07 and SEQ ID NO.:08; PP1 is the polypeptide selecting from the group of polypeptides having the amino acid sequences shown as SEQ ID NO.:02, SEQ ID NO.:04 and SEQ ID NO.:05 when PP2 is the polypeptide having the amino acid sequence shown as SEQ ID NO.:03; PP1 is the polypeptide having the amino acid sequence shown as SEQ ID NO.:05 when PP2 is the polypeptide selecting from the group of polypeptides having the amino acid sequences shown as SEQ ID NO.:06, SEQ ID NO.:07 and SEQ ID NO.:08;

wherein

Xaa1 is selected from the group consisting of Gly, Aib, D-Ser, Ser, Arg, Asn, Asp, Cys, Gln, Glu, His, Ile, Leu, Lys, Met, Phe, Pro, Thr, Trp, Tyr and Val;

Xaa2 is selected from the group consisting of Cys,

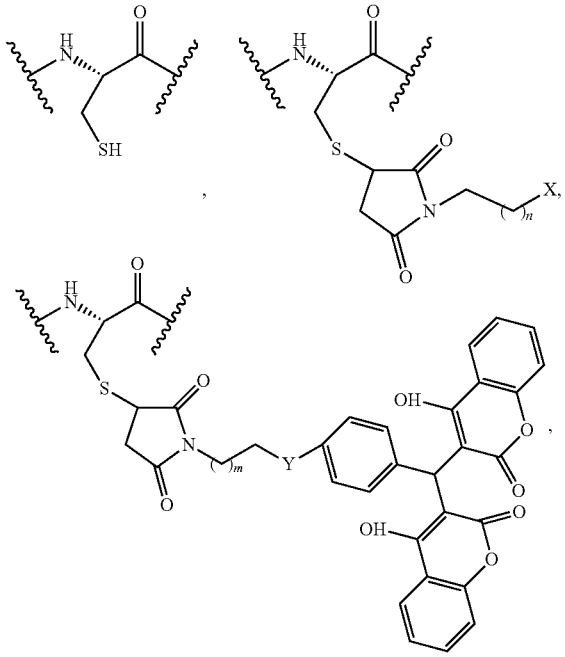

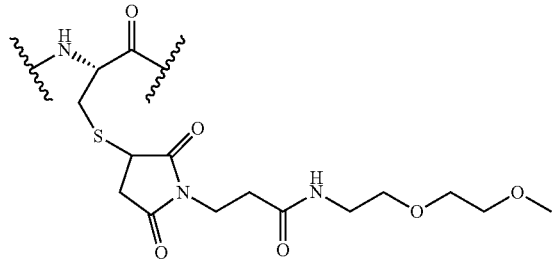

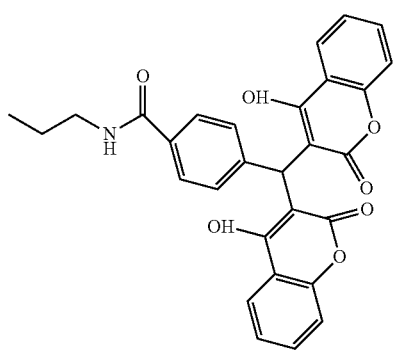

and

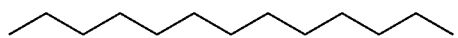

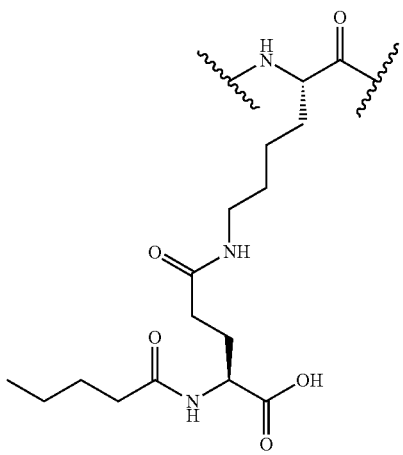

or

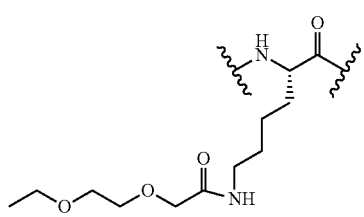

;

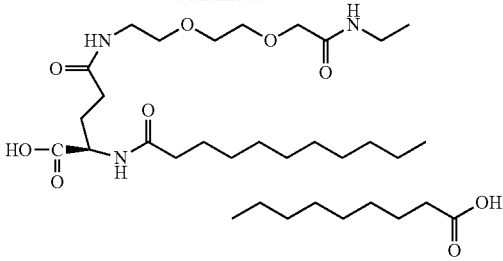

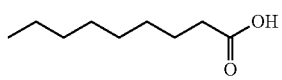

wherein X is —CH₃ or —COOH;
Y is —NH—CO— or —CO—NH—;
n is a natural number selected from 0 to 20;
m is a natural number selected from 1 to 20; and
Xaa3 is Ser-OH or Ser-NH₂;
wherein the compound is prepared by the following step:
  step 1: taking and activating resin, and then gradually coupling amino acids, so as to obtain first peptide resin;
  step 2: taking the first peptide resin, and coupling a fatty acid chain small molecule of Formula I or Formula II to a Lys side chain to obtain second peptide resin; and
  step 3: taking the second peptide resin, and performing lysis and purification to obtain the compound having the general formula His-Xaa1-PP1-Xaa2-PP2-Xaa3;

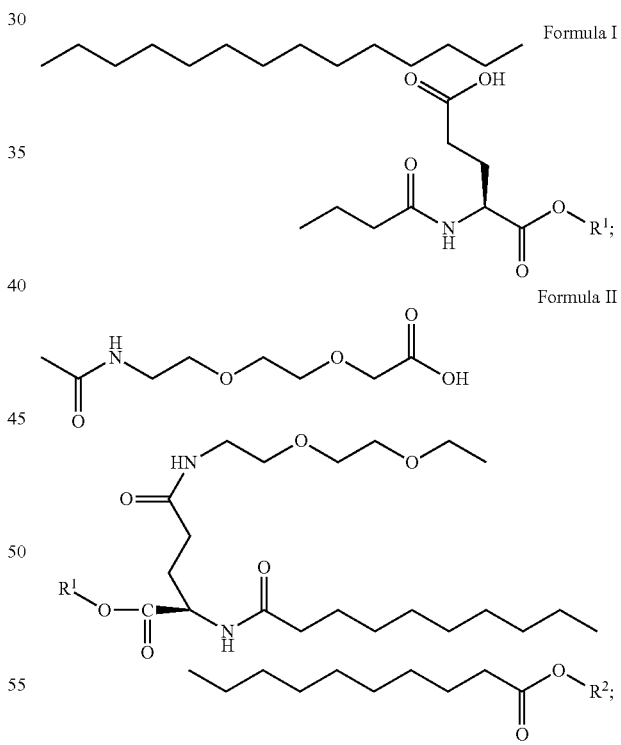

wherein R¹ is selected from tBu, Dmab, or Bzl;
R² is selected from methyl, ethyl, tert-butyl, and benzhydryl; and
  a Lys side chain protecting group coupled to the fatty acid chain small molecule of Formula I or Formula II is selected from Fmoc, Boc, Dde, or ivDde;
wherein the purity of the compound is higher than 85%; the compound maintains hypoglycemic activity for more than 40 hours.

2. The compound according to claim 1, wherein the compound has the general formula His-Xaa1-PP1-Xaa2-PP2-Xaa3,
wherein
Xaa1 is Gly or Aib;
Xaa2 is selected from the group consisting of Cys,
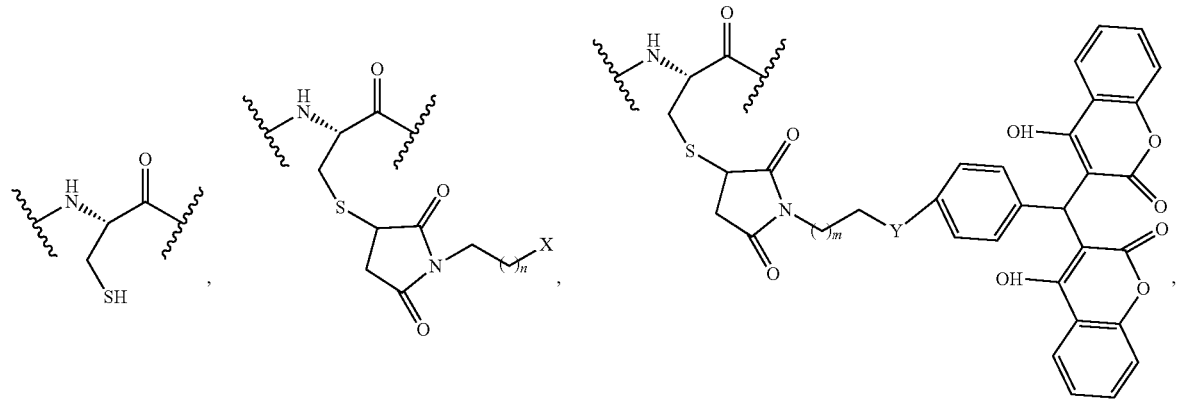,
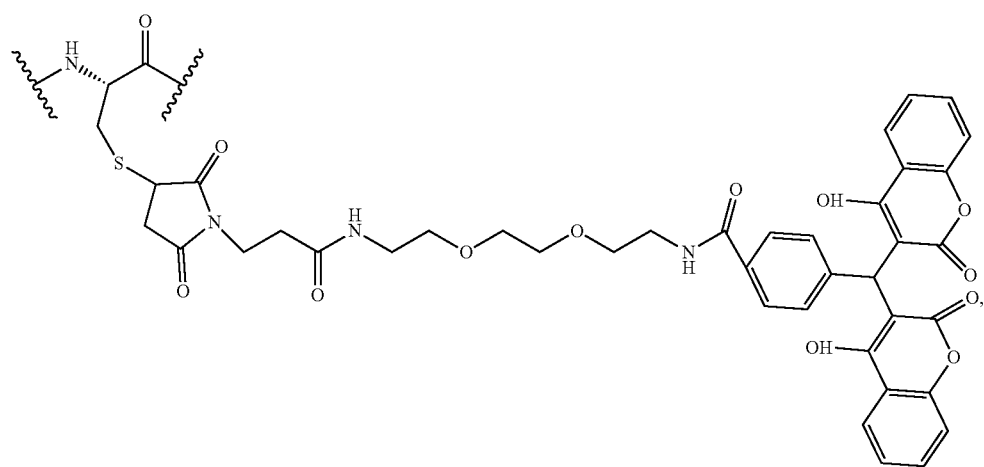,
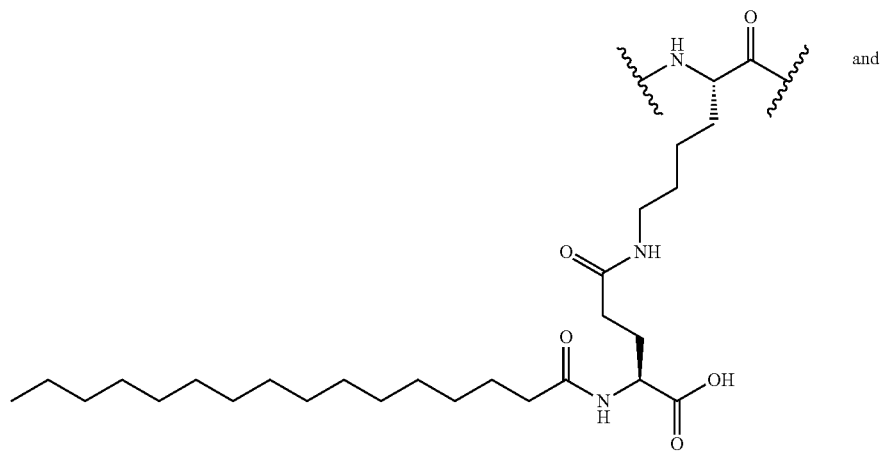 and

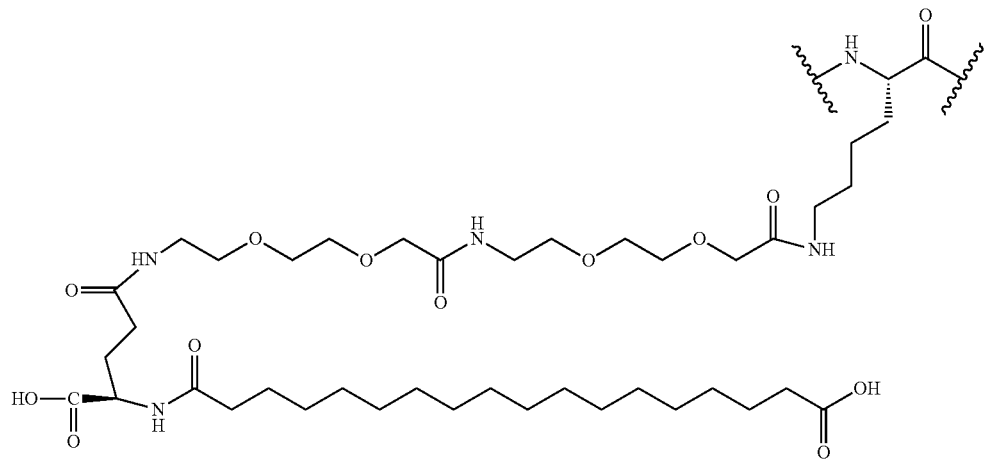

wherein X is —CH₃ or —COOH;
Y is —NH—CO— or —CO—NH—;
n is a natural number selected from 6, 10, 14, 11, or 15;
m is a natural number selected from 10 or 11;
Xaa3 is selected from Ser-OH or Ser-NH₂.

3. The compound according to claim 1, wherein the compound is selected from the group consisting of compound 1: His-Gly-PP1-Cys-PP2-Ser-NH2 wherein PP1 is the polypeptide having the amino acid sequence shown as SEQ ID NO.:02 and PP2 is the polypeptide having the amino acid sequence shown as SEQ ID NO.:03, compound 2: His-Gly-PP1-Cys-PP2-Ser-NH2 wherein PP1 is the polypeptide having the amino acid sequence shown as SEQ ID NO.:04 and PP2 is the polypeptide having the amino acid sequence shown as SEQ ID NO.:03, compound 3: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:06, compound 4: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:07, compound 5: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:03, compound 6: His-Gly-PP1-Cys-PP2-Ser-NH2 wherein PP1 is the polypeptide having the amino acid sequence shown as SEQ ID NO.:05 and PP2 is the polypeptide having the amino acid sequence shown as SEQ ID NO.:08, compound 7:

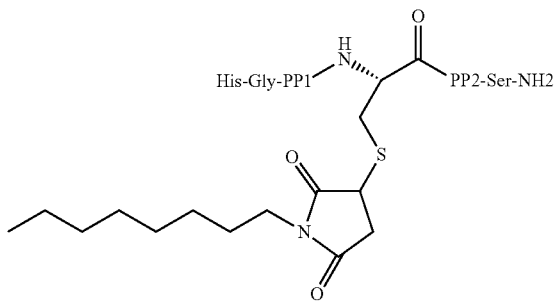

wherein PP1 is the polypeptide having the amino acid sequence shown as SEQ ID NO.:02 and PP2 is the polypeptide having the amino acid sequence shown as SEQ ID NO.:03, compound 8:

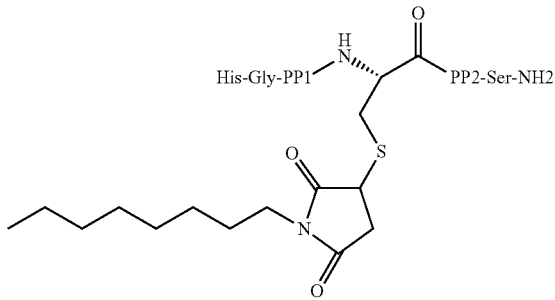

wherein PP1 is the polypeptide having the amino acid sequence shown as SEQ ID NO.:04 and PP2 is the polypeptide having the amino acid sequence shown as SEQ ID NO.:03, compound 9:

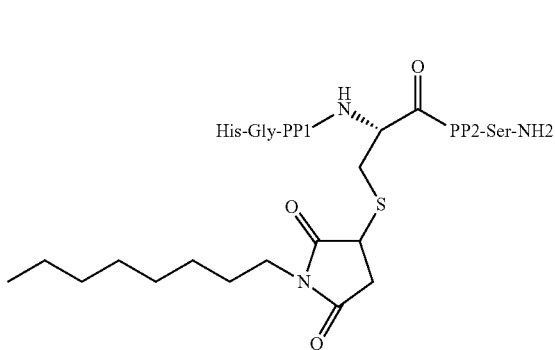

wherein PP1 is the polypeptide having the amino acid sequence shown as SEQ ID NO.:05 and PP2 is the polypeptide having the amino acid sequence shown as SEQ ID NO.:06, compound 10:

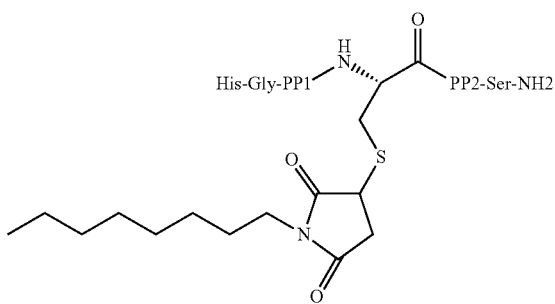

wherein PP1 is the polypeptide having the amino acid sequence shown as SEQ ID NO.:05 and PP2 is the polypeptide having the amino acid sequence shown as SEQ ID NO.:07, compound 11:

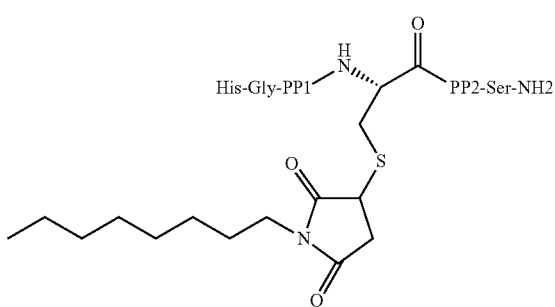

wherein PP1 is the polypeptide having the amino acid sequence shown as SEQ ID NO.:05 and PP2 is the polypeptide having the amino acid sequence shown as SEQ ID NO.:03, compound 12:

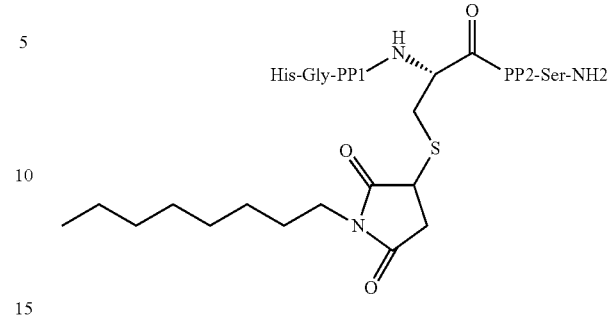

wherein PP1 is the polypeptide having the amino acid sequence shown as SEQ ID NO.:05 and PP2 is the polypeptide having the amino acid sequence shown as SEQ ID NO.:08, compound 13:

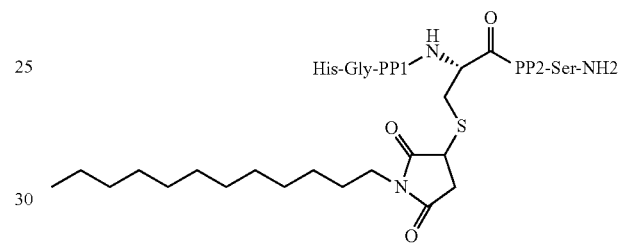

wherein PP1 is the polypeptide having the amino acid sequence shown as SEQ ID NO.:02 and PP2 is the polypeptide having the amino acid sequence shown as SEQ ID NO.:03, compound 14:

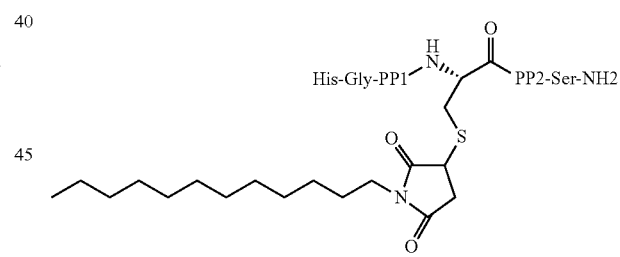

wherein PP1 is the polypeptide having the amino acid sequence shown as SEQ ID NO.:04 and PP2 is the polypeptide having the amino acid sequence shown as SEQ ID NO.:03, compound 15:

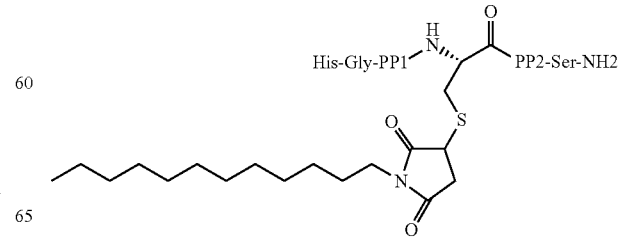

wherein PP1 is the polypeptide having the amino acid sequence shown as SEQ ID NO.:05 and PP2 is the polypeptide having the amino acid sequence shown as SEQ ID NO.:06,
compound 16:

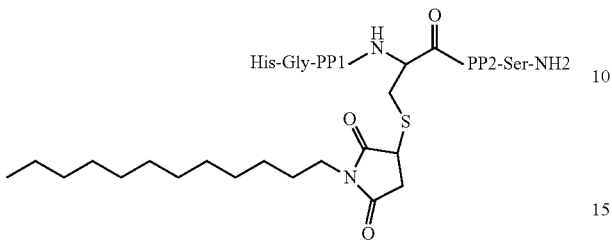

wherein PP1 is the polypeptide having the amino acid sequence shown as SEQ ID NO.:05 and PP2 is the polypeptide having the amino acid sequence shown as SEQ ID NO.:07,
compound 17:

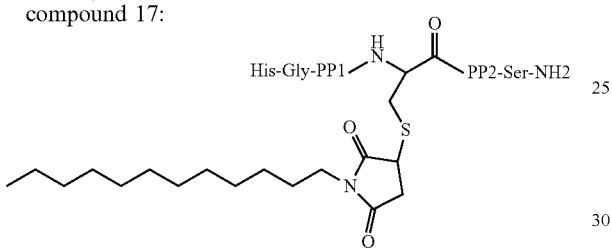

wherein PP1 is the polypeptide having the amino acid sequence shown as SEQ ID NO.:05 and PP2 is the polypeptide having the amino acid sequence shown as SEQ ID NO.:03, compound 18:

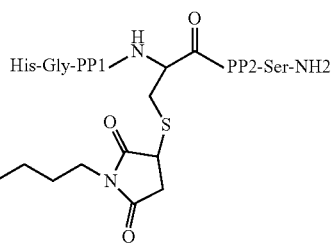

wherein PP1 is the polypeptide having the amino acid sequence shown as SEQ ID NO.:05 and PP2 is the polypeptide having the amino acid sequence shown as SEQ ID NO.:08, compound 19:

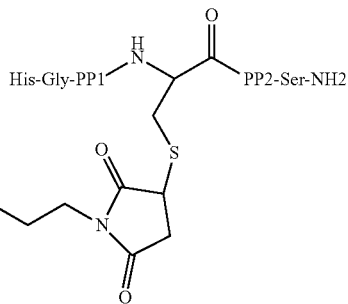

wherein PP1 is the polypeptide having the amino acid sequence shown as SEQ ID NO.:02 and PP2 is the polypeptide having the amino acid sequence shown as SEQ ID NO.:03,
compound 20:

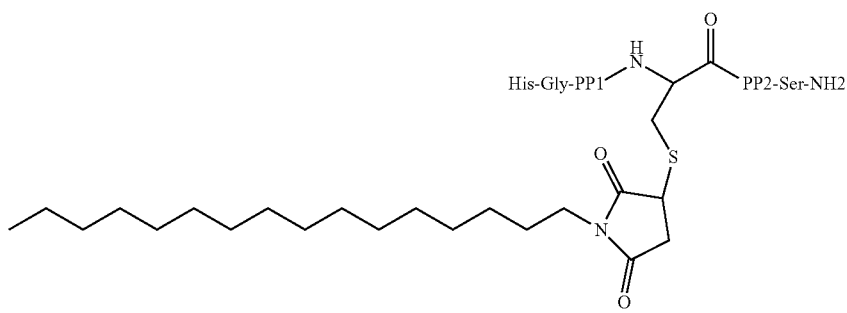

wherein PP1 is the polypeptide having the amino acid sequence shown as SEQ ID NO.:04 and PP2 is the polypeptide having the amino acid sequence shown as SEQ ID NO.:03, compound 21:

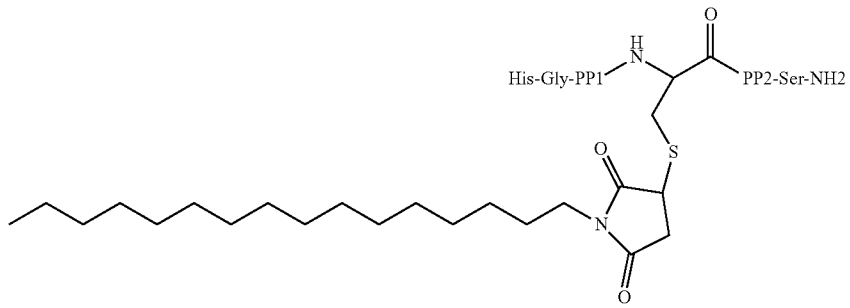

20 wherein PP1 is the polypeptide having the amino acid sequence shown as SEQ ID NO.:05 and PP2 is the polypeptide having the amino acid sequence shown as SEQ ID NO.:06, compound 22:

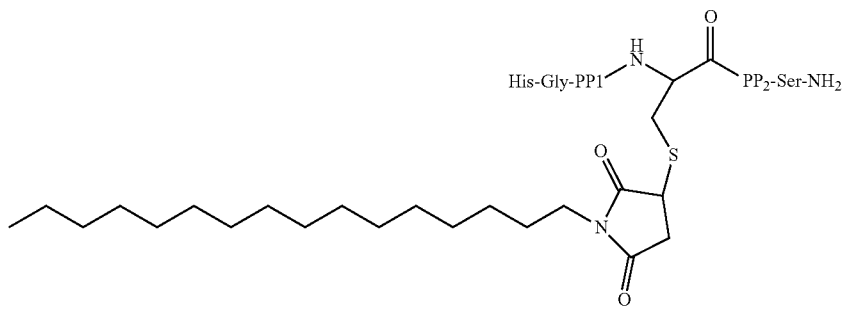

40 wherein PP1 is the polypeptide having the amino acid sequence shown as SEQ ID NO.:05 and PP2 is the polypeptide having the amino acid sequence shown as SEQ ID NO.:07, compound 23:

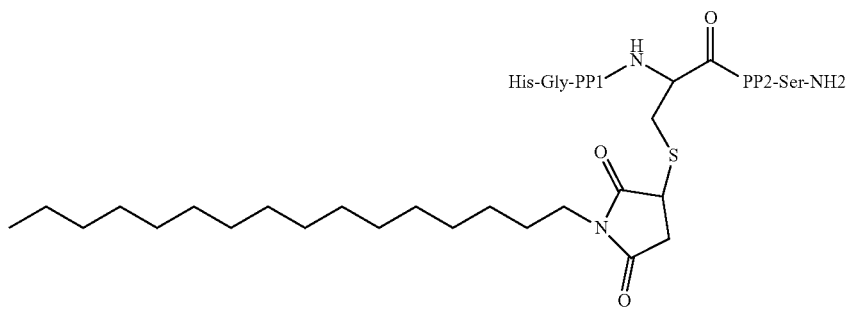

wherein PP1 is the polypeptide having the amino acid sequence shown as SEQ ID NO.:05 and PP2 is the polypeptide having the amino acid sequence shown as SEQ ID NO.:03, compound 24:

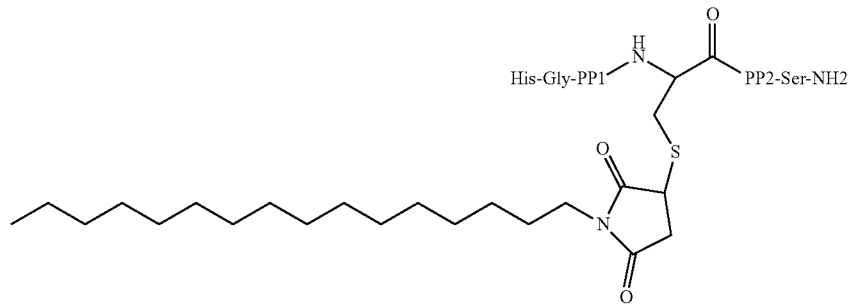

wherein PP1 is the polypeptide having the amino acid sequence shown as SEQ ID NO.:05 and PP2 is the polypeptide having the amino acid sequence shown as SEQ ID NO.:08, compound 25:

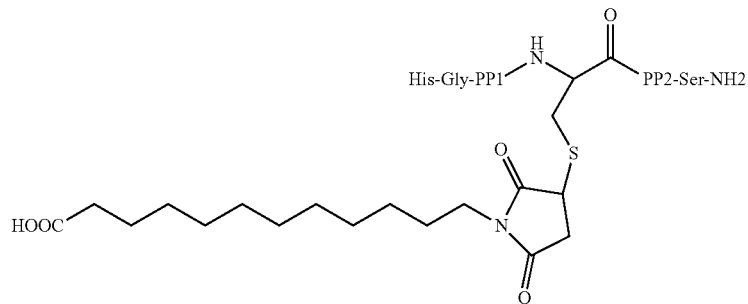

wherein PP1 is the polypeptide having the amino acid sequence shown as SEQ ID NO.:05 and PP2 is the polypeptide having the amino acid sequence shown as SEQ ID NO.:08, compound 26:

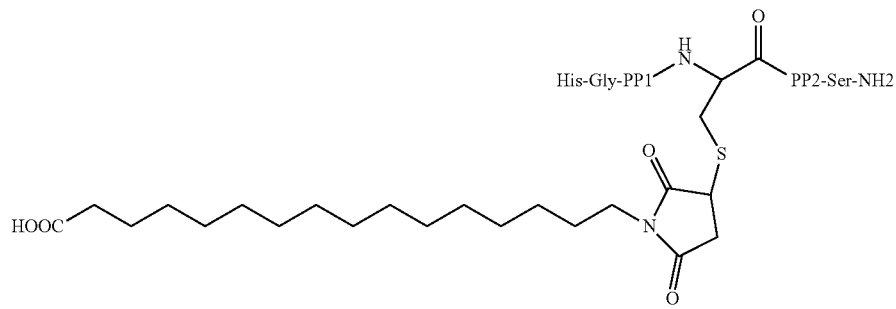

wherein PP1 is the polypeptide having the amino acid sequence shown as SEQ ID NO.:05 and PP2 is the polypeptide having the amino acid sequence shown as SEQ ID NO.:08, compound 27:
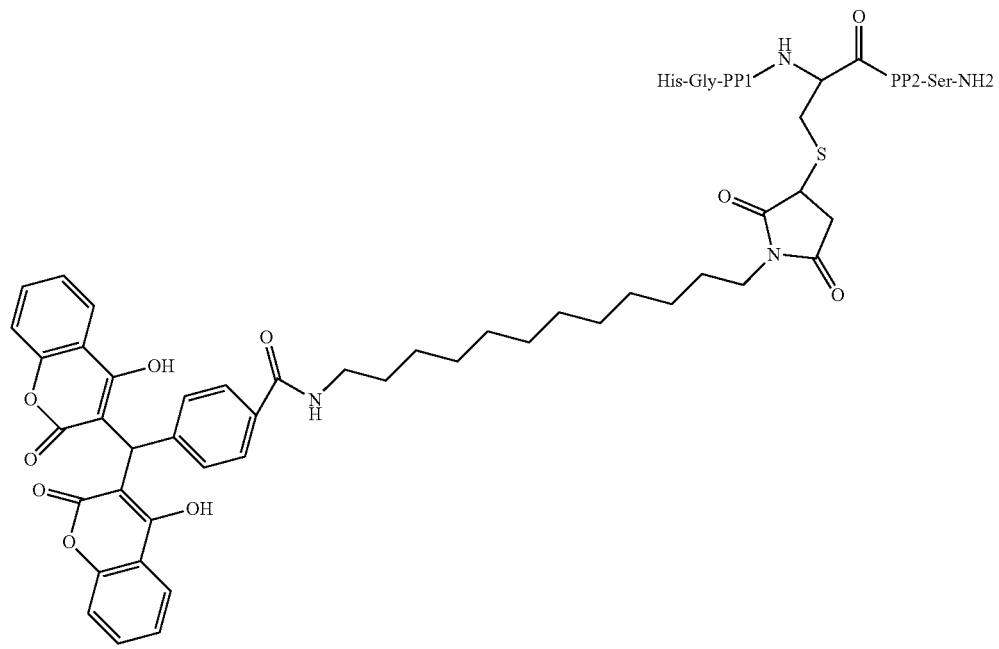
wherein PP1 is the polypeptide having the amino acid sequence shown as SEQ ID NO.:05 and PP2 is the polypeptide having the amino acid sequence shown as SEQ ID NO.:08,
compound 28:
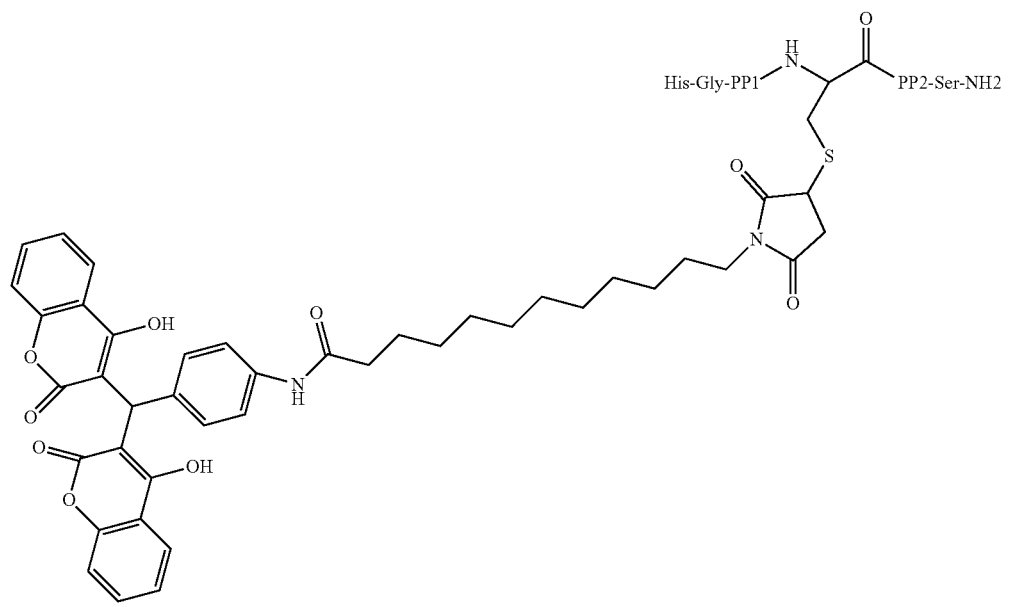
wherein PP1 is the polypeptide having the amino acid sequence shown as SEQ ID NO.:05 and PP2 is the polypeptide having the amino acid sequence shown as SEQ ID NO.:08, compound 29:
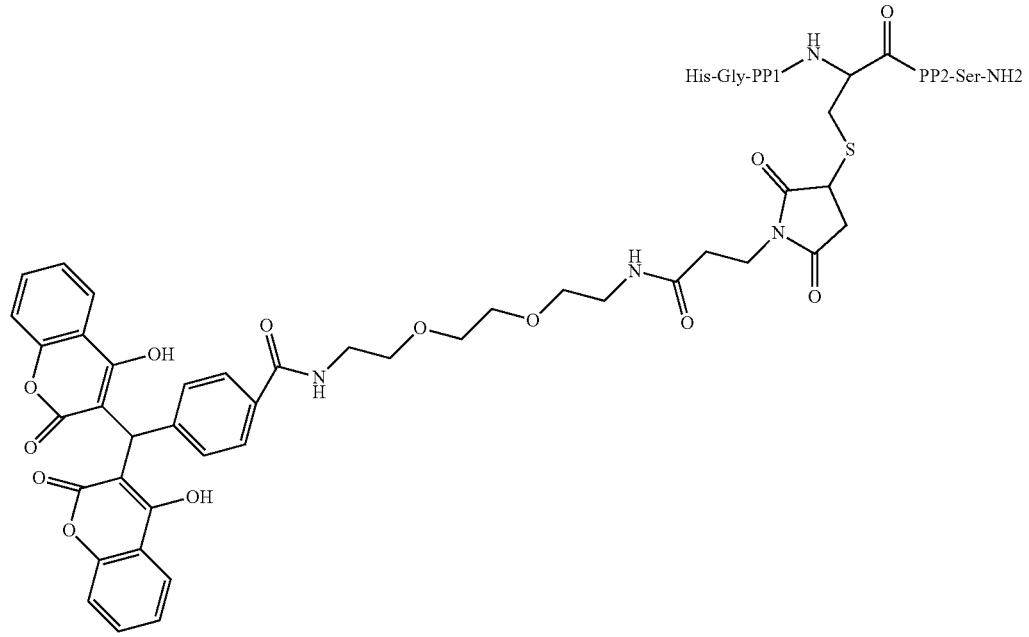
wherein PP1 is the polypeptide having the amino acid sequence shown as SEQ ID NO.:05 and PP2 is the polypeptide having the amino acid sequence shown as SEQ ID NO.:08,
compound 30:
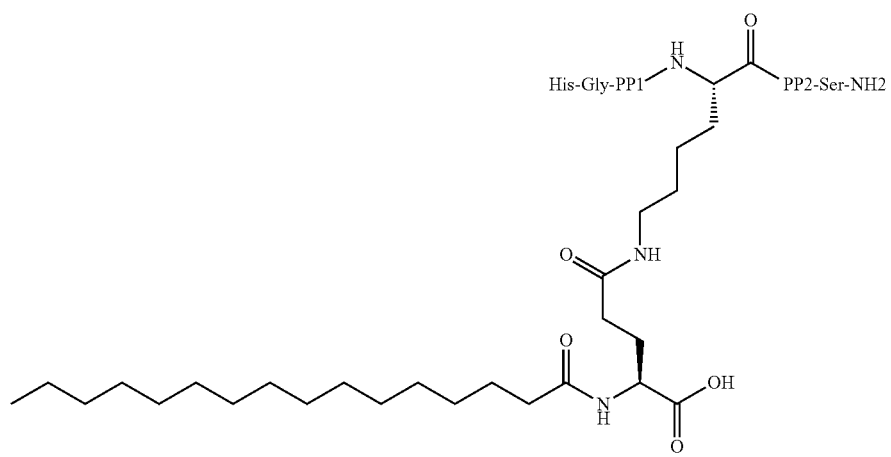
wherein PP1 is the polypeptide having the amino acid sequence shown as SEQ ID NO.:02 and PP2 is the polypeptide having the amino acid sequence shown as SEQ ID NO.:03, compound 31:
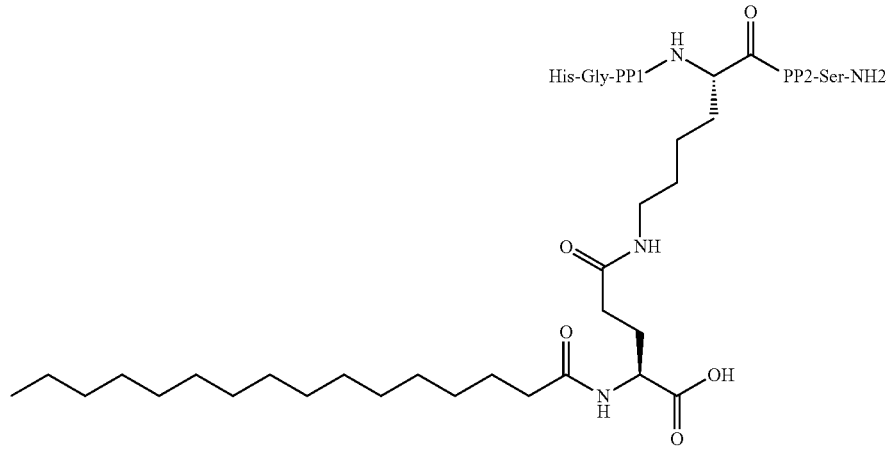
wherein PP1 is the polypeptide having the amino acid sequence shown as SEQ ID NO.:04 and PP2 is the polypeptide having the amino acid sequence shown as SEQ ID NO.:03,
compound 32:
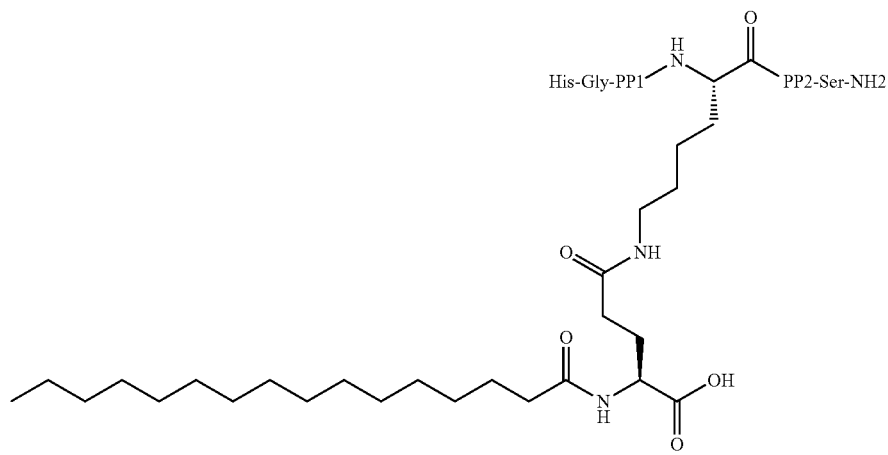
wherein PP1 is the polypeptide having the amino acid sequence shown as SEQ ID NO.:05 and PP2 is the polypeptide having the amino acid sequence shown as SEQ ID NO.:06, compound 33:
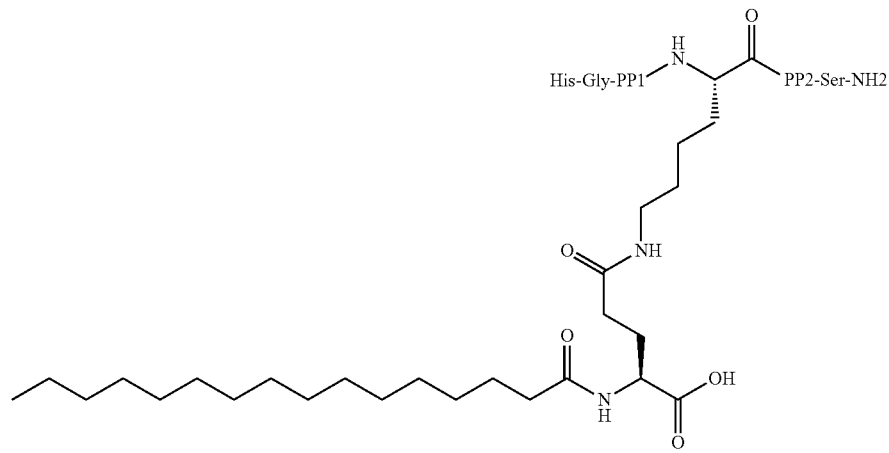
wherein PP1 is the polypeptide having the amino acid sequence shown as SEQ ID NO.:05 and PP2 is the polypeptide having the amino acid sequence shown as SEQ ID NO.:07,
compound 34:
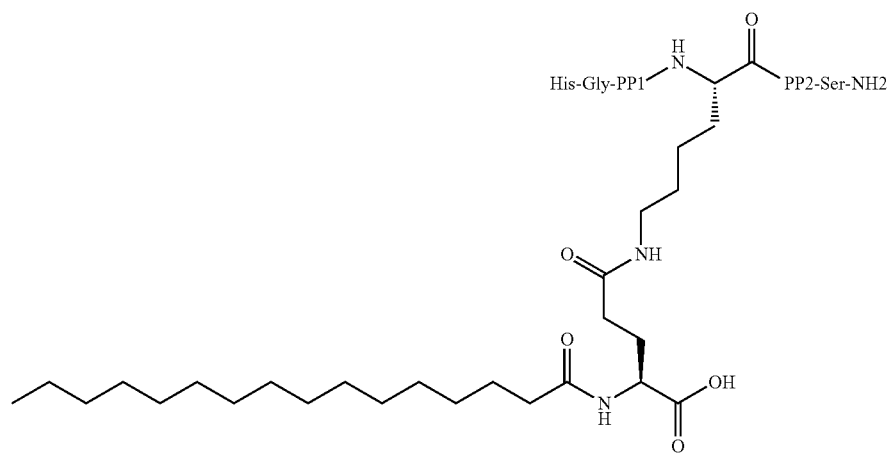
wherein PP1 is the polypeptide having the amino acid sequence shown as SEQ ID NO.:05 and PP2 is the polypeptide having the amino acid sequence shown as SEQ ID NO.:03, compound 35:
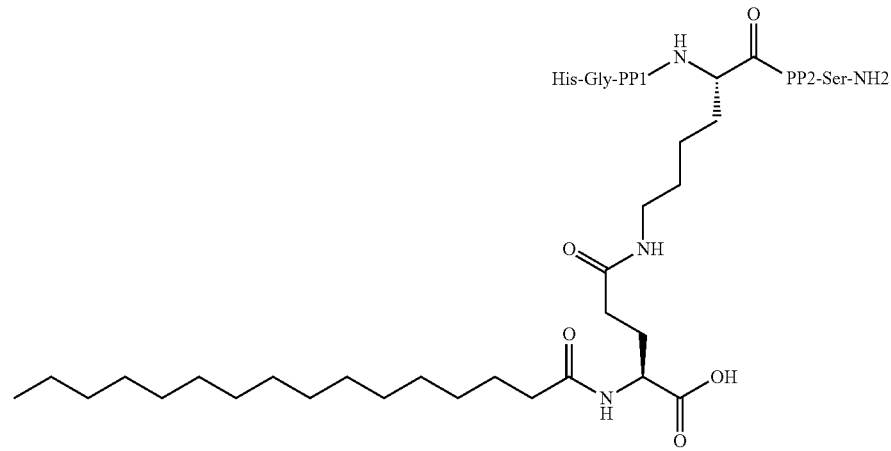
wherein PP1 is the polypeptide having the amino acid sequence shown as SEQ ID NO.:05 and PP2 is the polypeptide having the amino acid sequence shown as SEQ ID NO.:08,
compound 36:
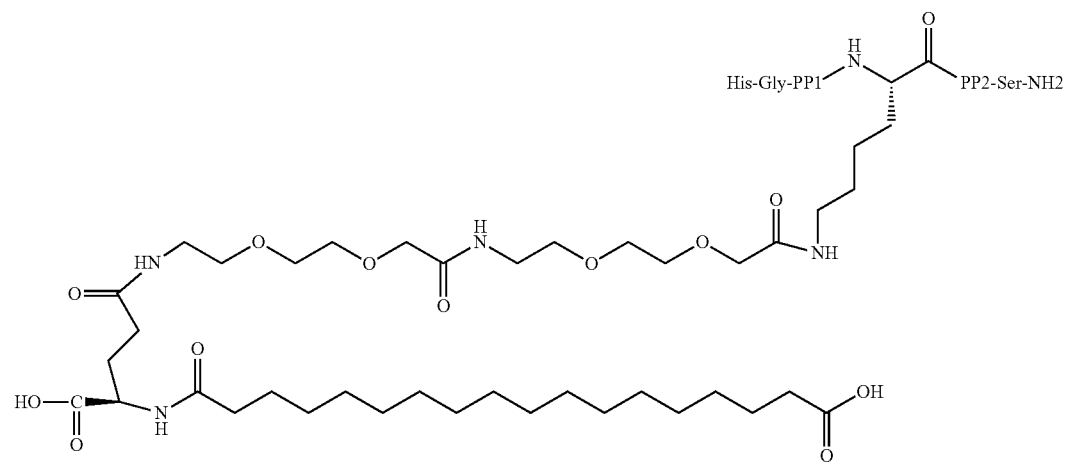
wherein PP1 is the polypeptide having the amino acid sequence shown as SEQ ID NO.:02 and PP2 is the polypeptide having the amino acid sequence shown as SEQ ID NO.:03, compound 37:
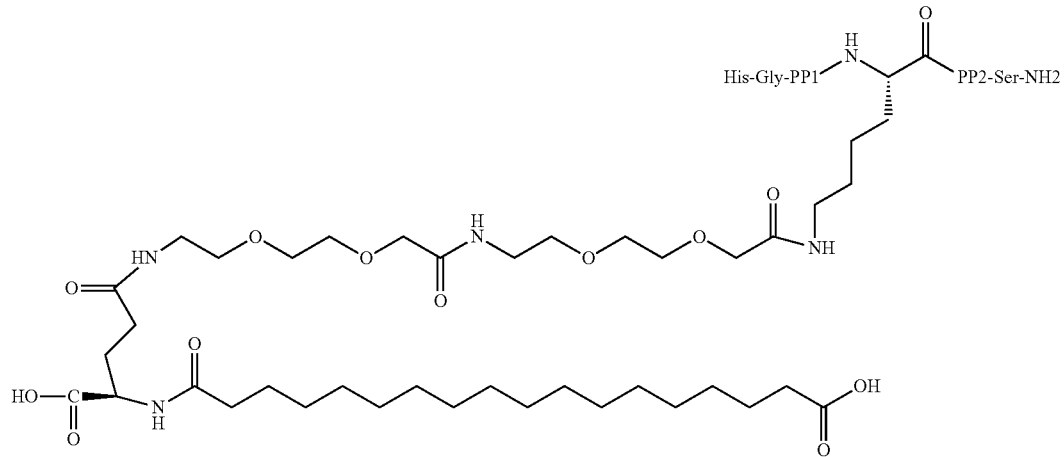
wherein PP1 is the polypeptide having the amino acid sequence shown as SEQ ID NO.:04 and PP2 is the polypeptide having the amino acid sequence shown as SEQ ID NO.:03,
compound 38:
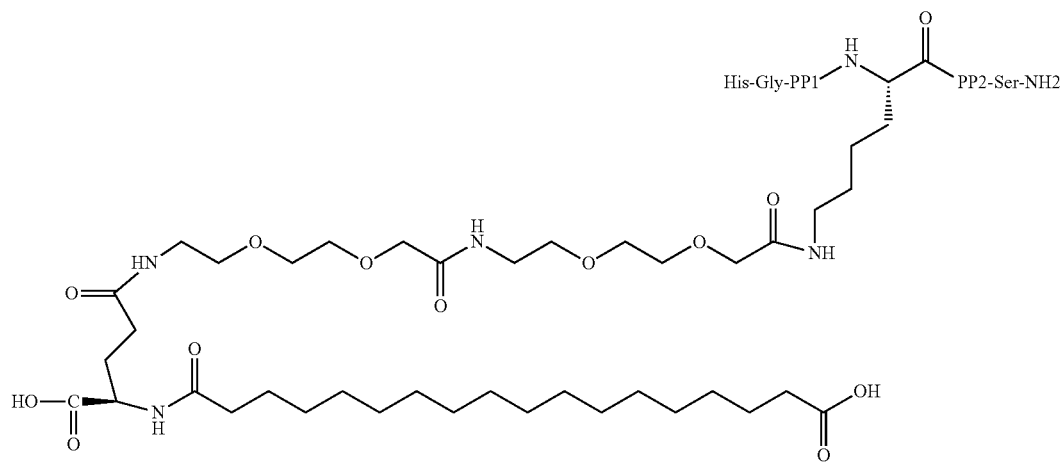
wherein PP1 is the polypeptide having the amino acid sequence shown as SEQ ID NO.:05 and PP2 is the polypeptide having the amino acid sequence shown as SEQ ID NO.:06, compound 39:
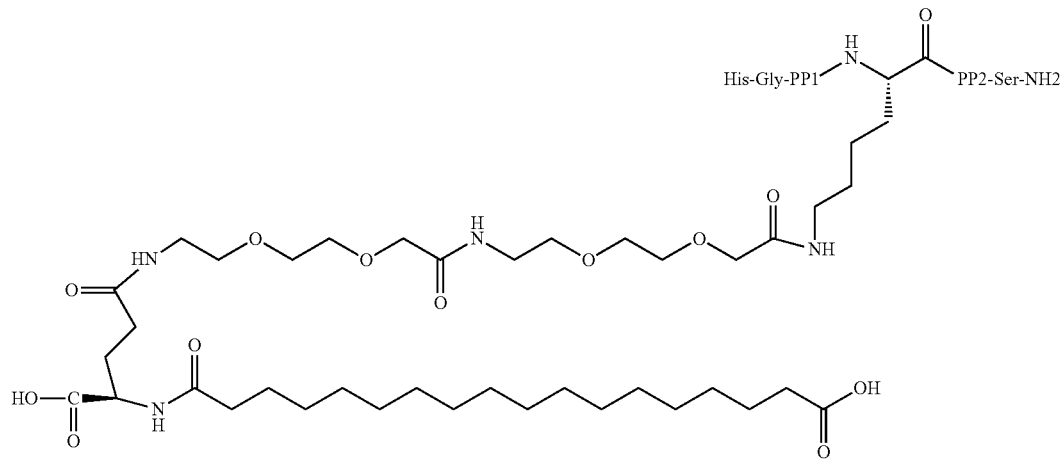
wherein PP1 is the polypeptide having the amino acid sequence shown as SEQ ID NO.:05 and PP2 is the polypeptide having the amino acid sequence shown as SEQ ID NO.:07,
compound 40:
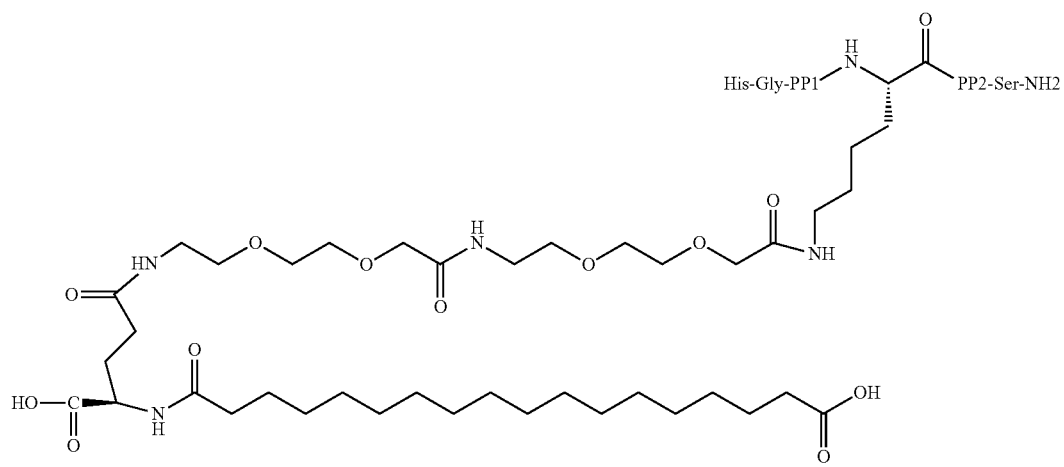
wherein PP1 is the polypeptide having the amino acid sequence shown as SEQ ID NO.:05 and PP2 is the polypeptide having the amino acid sequence shown as SEQ ID NO.:03, compound 41:

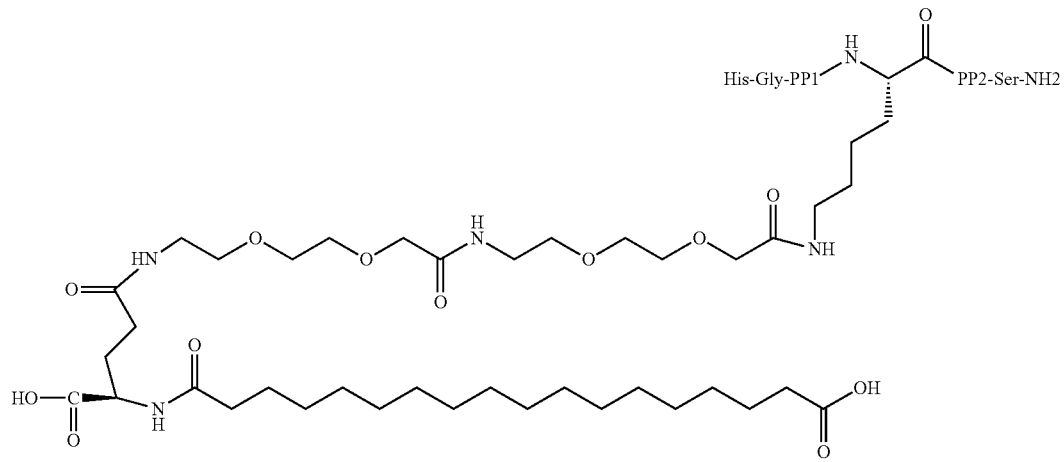

wherein PP1 is the polypeptide having the amino acid sequence shown as SEQ ID NO.:05 and PP2 is the polypeptide having the amino acid sequence shown as SEQ ID NO.:08, compound 42:

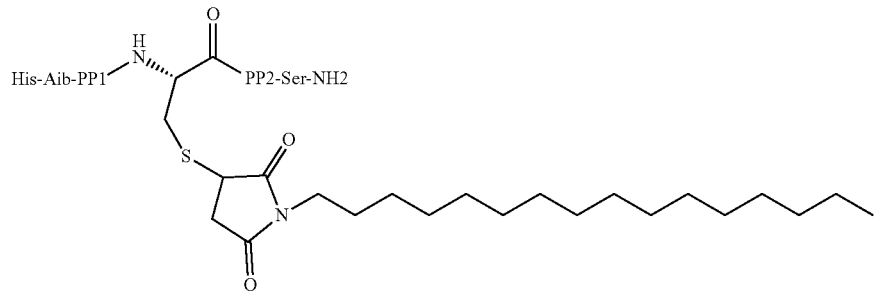

wherein PP1 is the polypeptide having the amino acid sequence shown as SEQ ID NO.:05 and PP2 is the polypeptide having the amino acid sequence shown as SEQ ID NO.:03, compound 43:

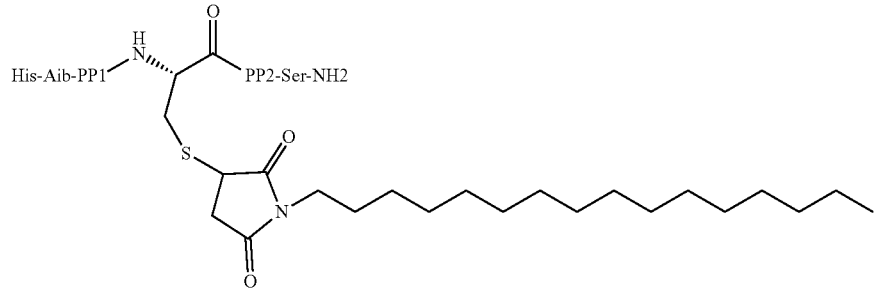

wherein PP1 is the polypeptide having the amino acid sequence shown as SEQ ID NO.:05 and PP2 is the polypeptide having the amino acid sequence shown as SEQ ID NO.:08, compound 44:
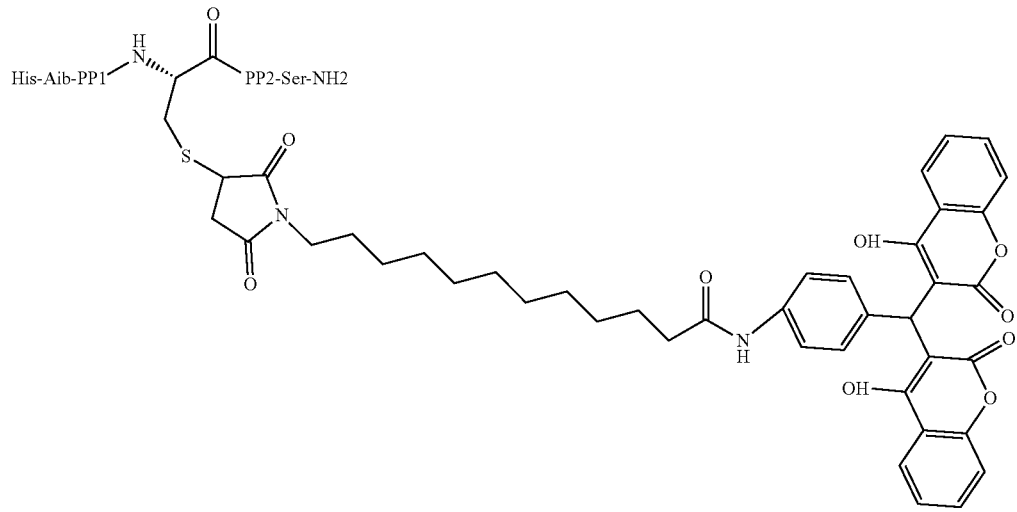
wherein PP1 is the polypeptide having the amino acid sequence shown as SEQ ID NO.:05 and PP2 is the polypeptide having the amino acid sequence shown as SEQ ID NO.:03,
compound 45:
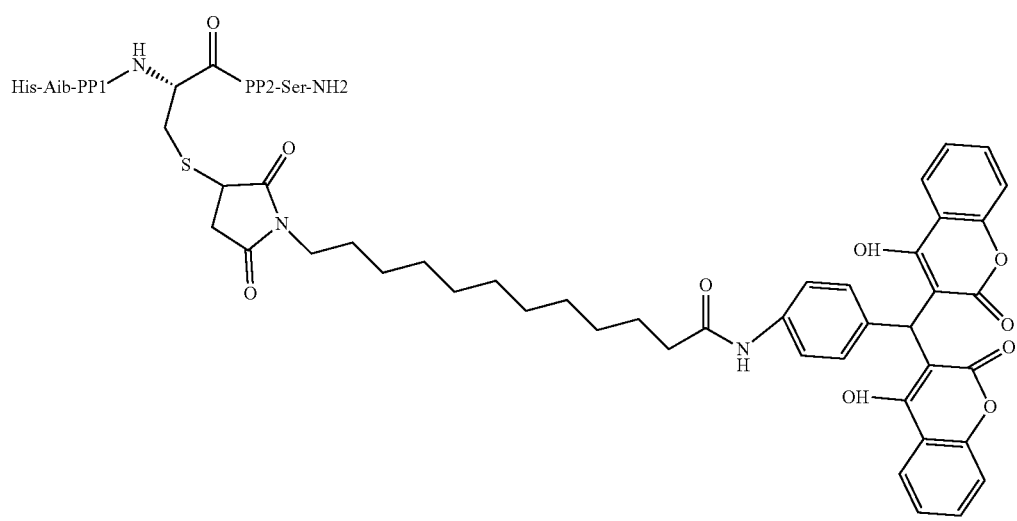
wherein PP1 is the polypeptide having the amino acid sequence shown as SEQ ID NO.:05 and PP2 is the polypeptide having the amino acid sequence shown as SEQ ID NO.:08, compound 46:
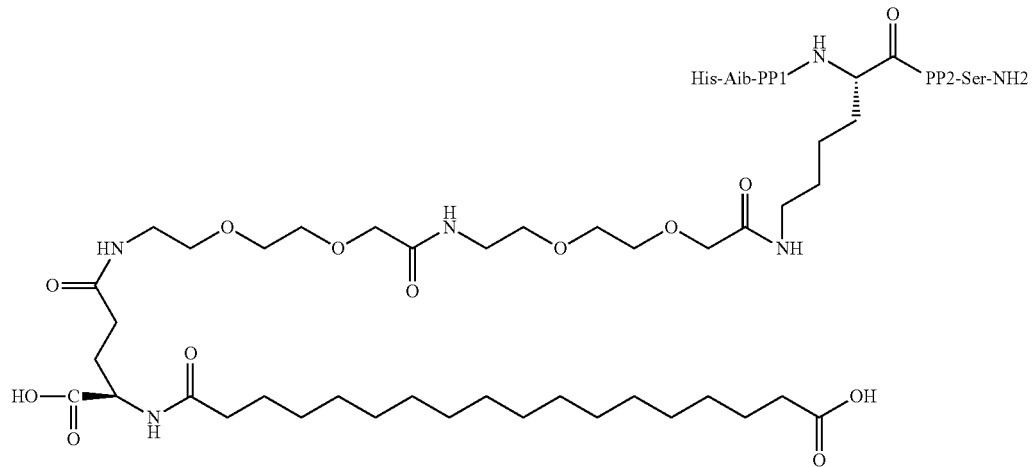
wherein PP1 is the polypeptide having the amino acid sequence shown as SEQ ID NO.:05 and PP2 is the polypeptide having the amino acid sequence shown as SEQ ID NO.:03,
compound 47:
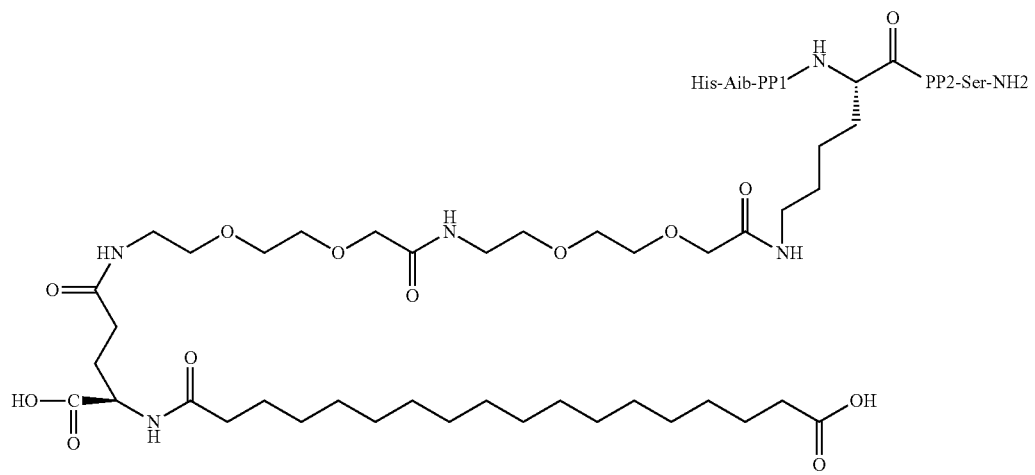
wherein PP1 is the polypeptide having the amino acid sequence shown as SEQ ID NO.:05 and PP2 is the polypeptide having the amino acid sequence shown as SEQ ID NO.:08, compound 48:
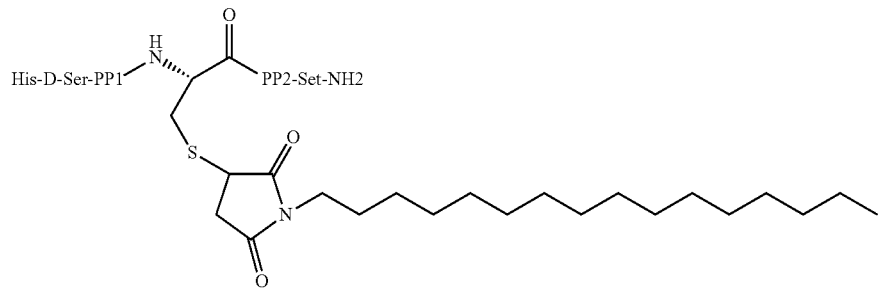
wherein PP1 is the polypeptide having the amino acid sequence shown as SEQ ID NO.:05 and PP2 is the polypeptide having the amino acid sequence shown as SEQ ID NO.:03,
compound 49:
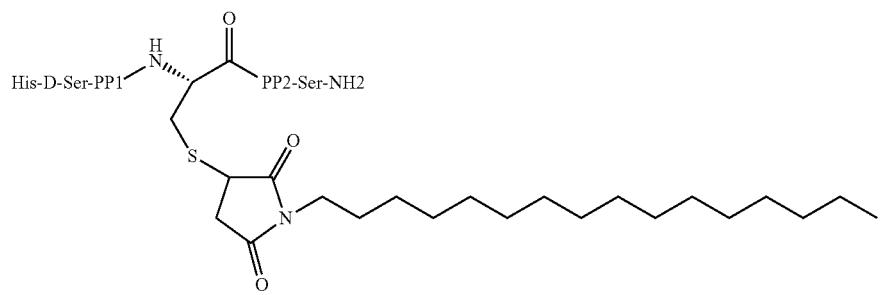
wherein PP1 is the polypeptide having the amino acid sequence shown as SEQ ID NO.:05 and PP2 is the polypeptide having the amino acid sequence shown as SEQ ID NO.:08,
compound 50:
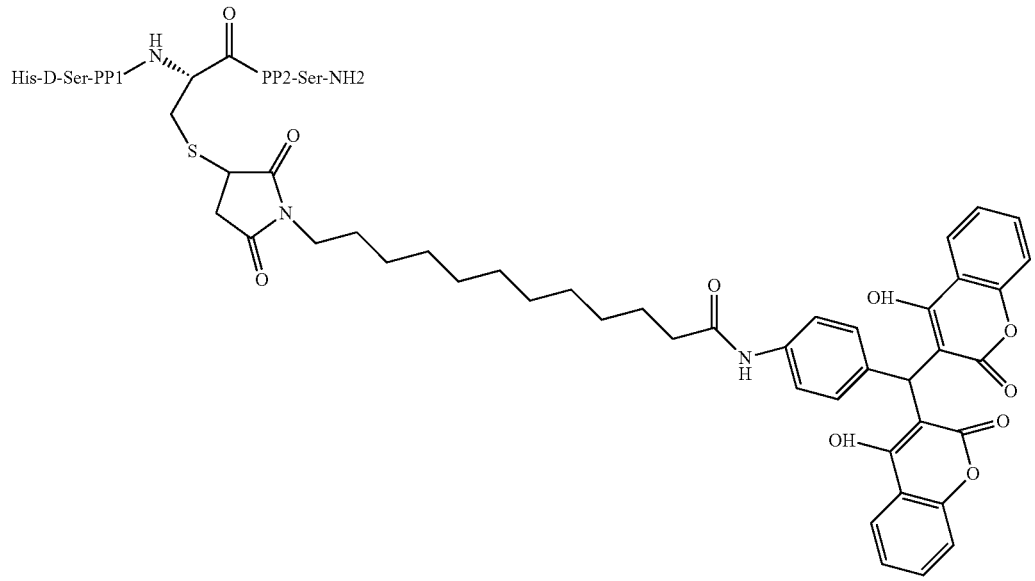

wherein PP1 is the polypeptide having the amino acid sequence shown as SEQ ID NO.:05 and PP2 is the polypeptide having the amino acid sequence shown as SEQ ID NO.:03, compound 51:

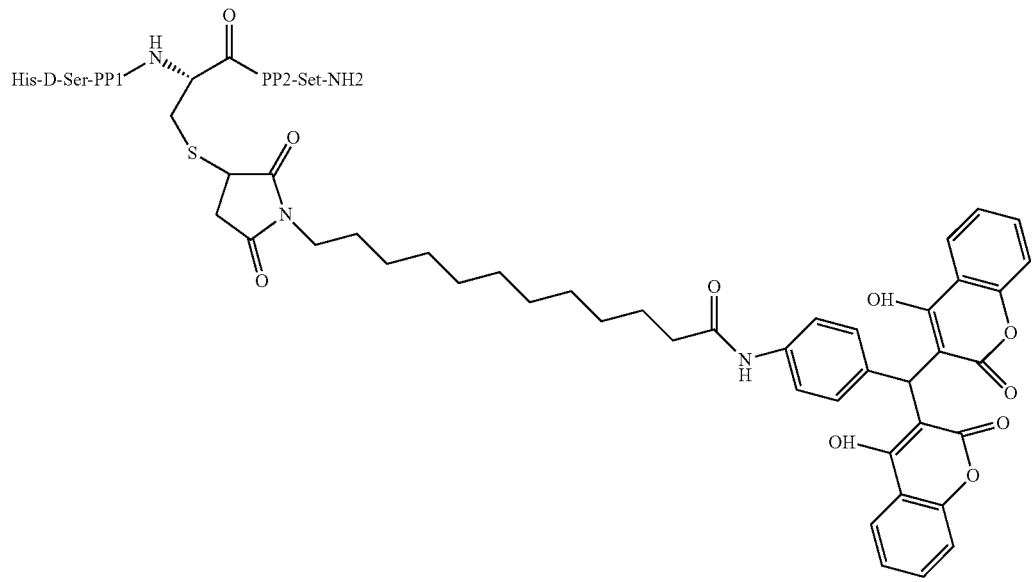

wherein PP1 is the polypeptide having the amino acid sequence shown as SEQ ID NO.:05 and PP2 is the polypeptide having the amino acid sequence shown as SEQ ID NO.:08, compound 52:

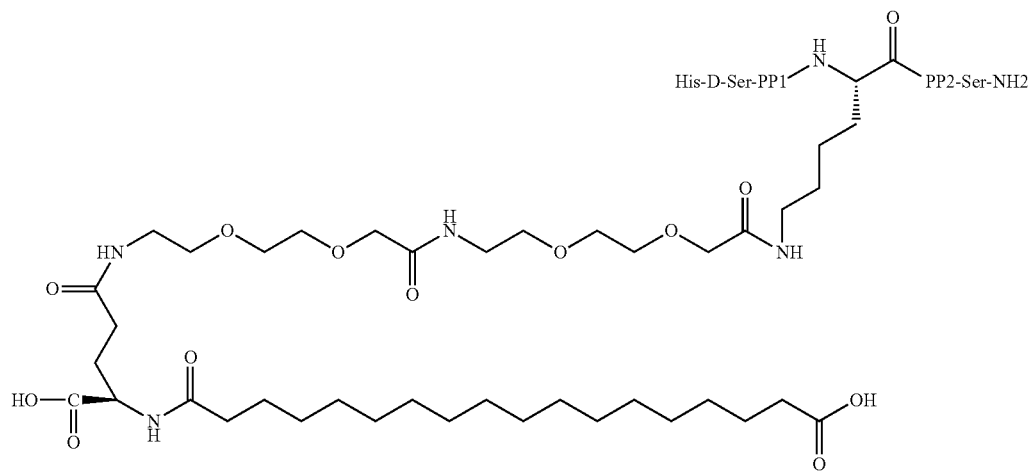

wherein PP1 is the polypeptide having the amino acid sequence shown as SEQ ID NO.:05 and PP2 is the polypeptide having the amino acid sequence shown as SEQ ID NO.:03, compound 53:

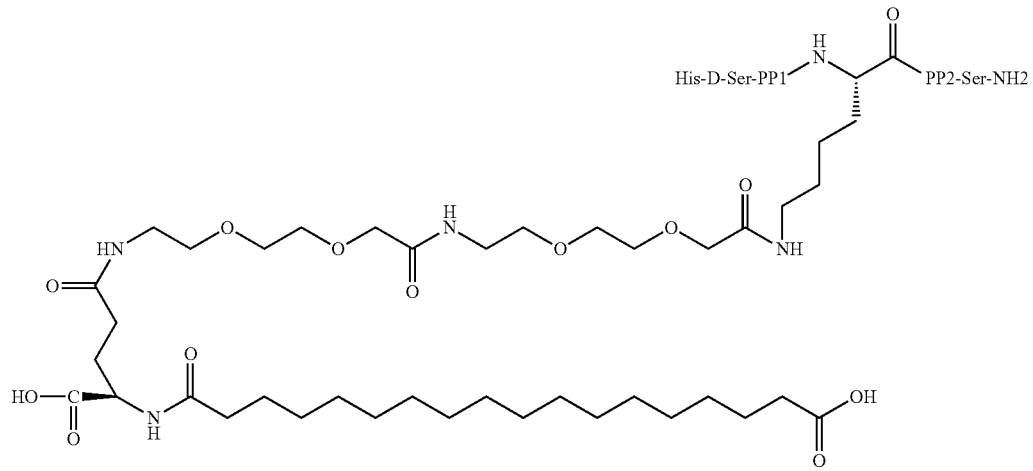

wherein PP1 is the polypeptide having the amino acid sequence shown as SEQ ID NO.:05 and PP2 is the polypeptide having the amino acid sequence shown as SEQ ID NO.:08, compound 54:

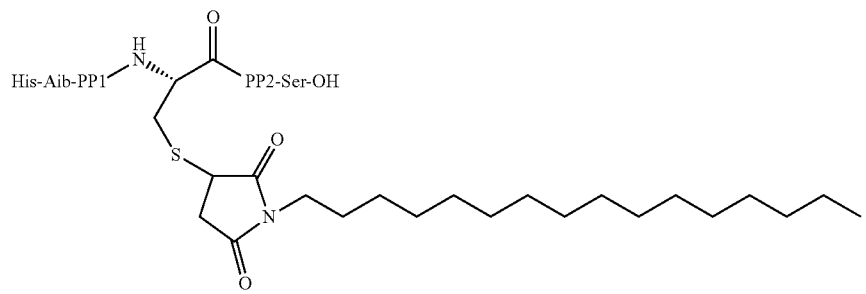

wherein PP1 is the polypeptide having the amino acid sequence shown as SEQ ID NO.:05 and PP2 is the polypeptide having the amino acid sequence shown as SEQ ID NO.:03, compound 55:

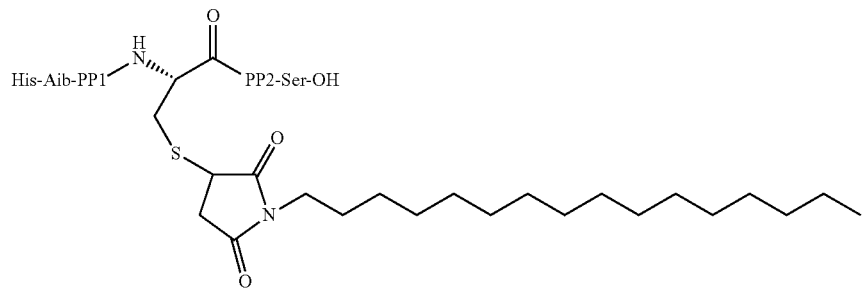

wherein PP1 is the polypeptide having the amino acid sequence shown as SEQ ID NO.:05 and PP2 is the polypeptide having the amino acid sequence shown as SEQ ID NO.:08, compound 56:
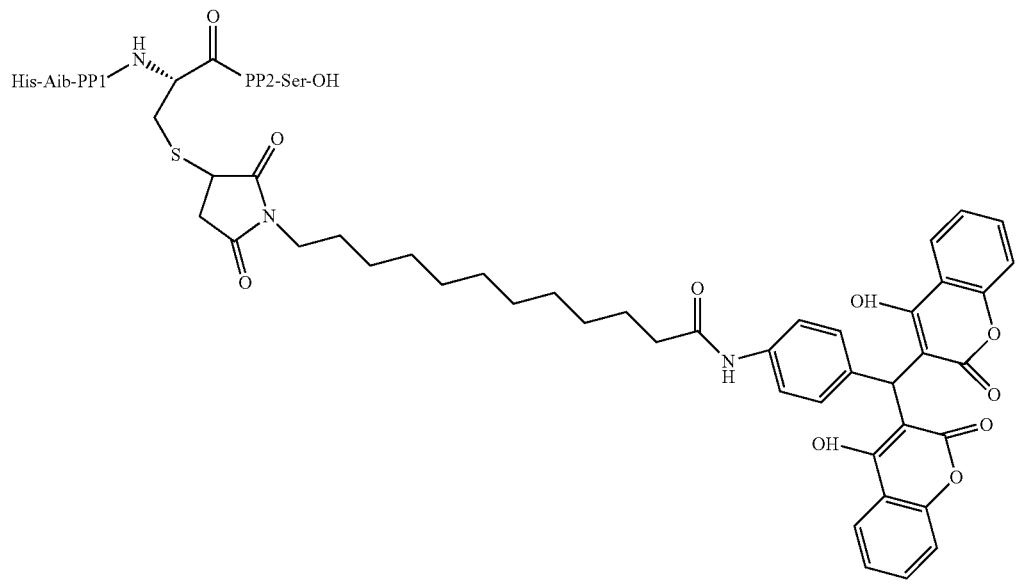
wherein PP1 is the polypeptide having the amino acid sequence shown as SEQ ID NO.:05 and PP2 is the polypeptide having the amino acid sequence shown as SEQ ID NO.:03,
compound 57:
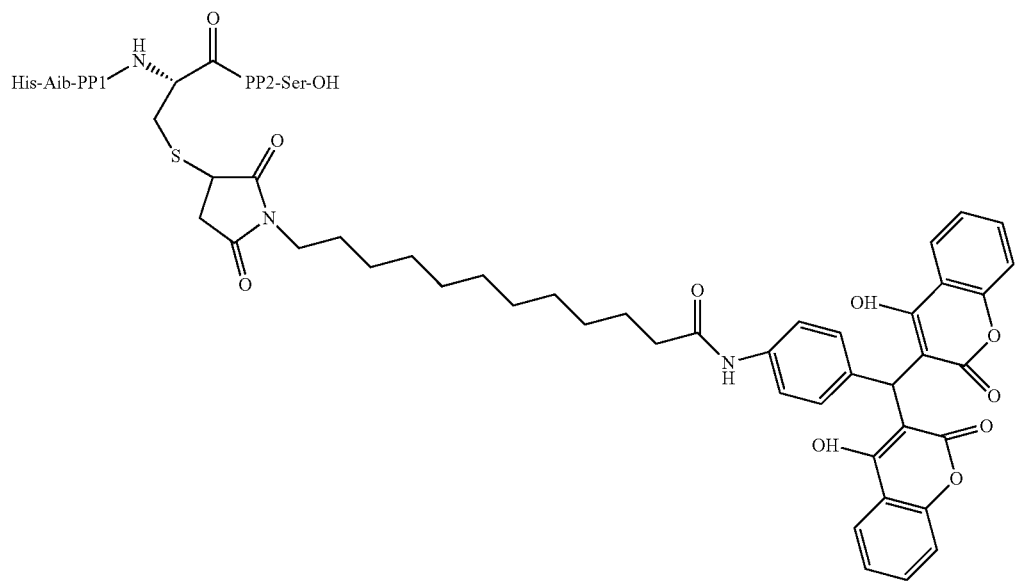
wherein PP1 is the polypeptide having the amino acid sequence shown as SEQ ID NO.:05 and PP2 is the polypeptide having the amino acid sequence shown as SEQ ID NO.:08, compound 58:

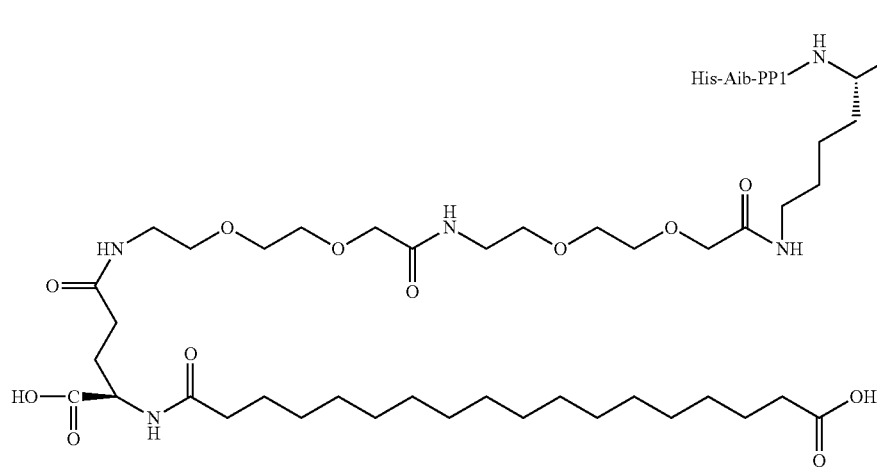

wherein PP1 is the polypeptide having the amino acid sequence shown as SEQ ID NO.:05 and PP2 is the polypeptide having the amino acid sequence shown as SEQ ID NO.:03, and compound 59:

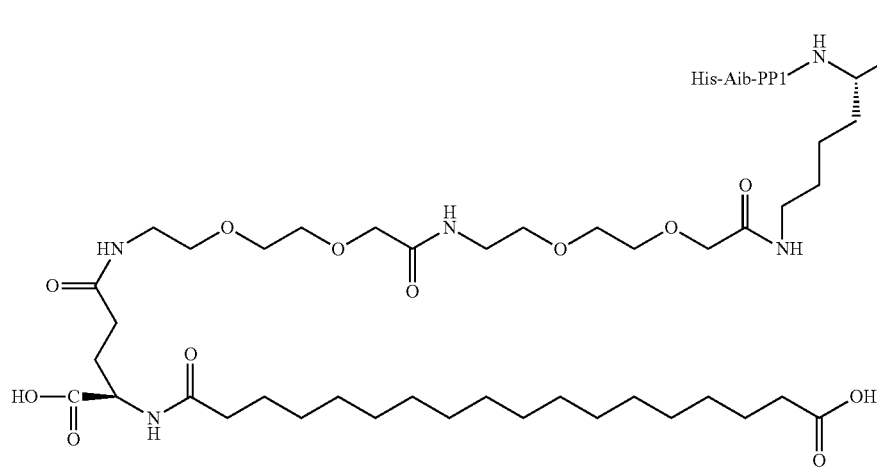

wherein PP1 is the polypeptide having the amino acid sequence shown as SEQ ID NO.:05 and PP2 is the polypeptide having the amino acid sequence shown as SEQ ID NO.:08.

4. The compound according to claim 1, wherein the compound is prepared by the following step:
step 1: taking and activating resin, and then gradually coupling amino acids, so as to obtain first peptide resin;
step 2: taking the first peptide resin, and performing lysis and purification to obtain a pure peptide chain; and
step 3: conjugating thiol of Cys in the pure peptide chain with a fatty acid chain or a coumarin small molecule linked with a maleimide linking arm to obtain the compound according to claim 1.

5. The compound according to claim 1, wherein the pharmaceutically acceptable salt is prepared by a chemical selected from the group consisting of hydrochloric acid, hydrobromic acid, hydroiodic acid, sulfuric acid, pyrosulfuric acid, phosphoric acid, nitric acid, methanesulfonic acid, ethanesulfonic acid, benzenesulfonic acid, P-toluenesulfonic acid, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl) benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid and thiocyanic acid.

6. A pharmaceutical composition comprising a therapeutically effective amount of the compound of claim 1 and a pharmaceutically acceptable carrier.

7. The pharmaceutical composition according to claim 6, wherein the pharmaceutical composition is made as a medicament selected from the group consisting of a tablet, a capsule, an elixir, a syrup, a lozenge, an inhalant, a spray, an injection, a film, a patch, powder, granula, a block, an emulsion and a suppository.

8. A method for treating a disease comprising a step of administering the compound of claim 1 on a subject in need thereof, wherein the disease is selected from the group consisting of diabetes, obesity, hyperlipidemia, and non-alcoholic fatty liver.

* * * * *